US006472140B1

(12) United States Patent
Tanzi et al.

(10) Patent No.: US 6,472,140 B1
(45) Date of Patent: Oct. 29, 2002

(54) α-2- MACROGLOBULIN THERAPIES AND DRUG SCREENING METHODS FOR ALZHEIMER'S DISEASE.

(75) Inventors: Rudolph E. Tanzi, Hull, MA (US); Dora Kovacs, Boston, MA (US); Aleister J. Saunders, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/241,606

(22) Filed: Feb. 2, 1999

Related U.S. Application Data

(63) Continuation-in-part of application No. 09/148,503, filed on Sep. 4, 1998, now Pat. No. 6,342,350.
(60) Provisional application No. 60/057,655, filed on Sep. 5, 1997, and provisional application No. 60/093,297, filed on Jul. 17, 1998.

(51) Int. Cl.⁷ .......................... C12Q 1/00; G01N 33/53
(52) U.S. Cl. ............................ 435/4; 435/7.1
(58) Field of Search .............................. 435/5, 7.1, 29, 435/4, 7.21; 514/44

(56) References Cited

FOREIGN PATENT DOCUMENTS

| WO | WO 91/03557 | 3/1991 |
|----|-------------|--------|
| WO | WO 92/03474 | 3/1992 |
| WO | WO 96/39834 | 12/1996 |
| WO | WO97/04794 | 2/1997 |
| WO | WO 99/11824 | 3/1999 |

OTHER PUBLICATIONS

B Fakler et at., Journal of Biological Chemistry, "Short Antisense Oligonucleotide–mediated Inhibition Is Strongly Dependent on Oligo Length and Concentration but Almost Independent of Location of the Target Sequence,"1994, vol. 269, No. 23, pp. 16187–16194.*
Shibata et al., Neuroscience Letters, vol. 271 (2): 132–4, Aug. 1999.*
Hu et al., Neurology, vol. 53 (3): 642–3, Aug. 1999.*
Korovaitseva et al., Neuroscience Letters, vol. 271 (2): 129–31, Aug. 1999.*
Liao, A. et al., "Genetic association of an α2–macroglobulin (VAl1000Ile) polymorphism and Alzheimer's disease," Hum. Mol. Gen. 7:1953–1956 (Nov. 1998).
Stratagene, 1998 Catalog, "Gene Characterization Kits", La Jolla, CA (Feb. 1997).
Wavrant–DeVrièze, F. et al., "No association between the alpha–2 macroglobulin I1000V polymorphism and Alzheimer's disease," Neur. Letts. 262:137–139 (Mar. 1999).
Poller, W., et al., "Sequence Polymorphism in the Human α–2–macroglobulin (A2M) Gene," Nucl. Acids Res. 19:198 (1991).

International Search Report for International Application No. PCT/US00/02412, mailed Jul. 6, 2000.
Andersen, G.R. et al., "Low Resolution X–Ray Structure of Human Methylamine–treated $\alpha_2$–Macroglobulin,". J. Biol. Chem. 270:25133–25151 (1995).
Barrett, A.J., et al.,"The Electrophoretically 'Slow' and 'Fast' Forms of the $\alpha_2$–Macroglobulin Molecule," Biochem. J. 181:401–418 (1979).
Blacker, D., et al.,"Alpha–2 macroglobulin is genetically associated with Alzheimer disease," Nat. Genet. 19:357–360 (1998).
Bauer, J., et al., "Interleukin–6 and α–2–macroglobulin indicate an acute–phase state in Alzheimer's disease cortices," FEBS Lett. 285:111–114 (1991).
Boado, R., "Antisense drug delivery through the blood–brain barrier," Adv. Drug Delivery Rev., 15:73–107 (1995).
Boado, R., et al., "Drug delivery of Antisense Molecules to the Brain for Treatment of Alzheimer's Disease and Cerebral AIDS," J. Pharm. Sci. 87:1308–1315 (1998).
Borth, W., "$\alpha_2$ Macroglobulin a multifunctional binding protein with targeting characteristics," FASEB J. 6:3345–3353 (1992).
Bowen, M.E., and Gettins, P.W., "Bait Region Involvement in the Dimer—Dimer Interface of Human $\alpha_2$ Macroglobulin and in Mediating Gross Conformational Change," J. Biol. Chem. 273:1825–1831 (1998).
Bretaudiere, J.–P., et al., "Structure of native $\alpha_2$–macroglobulin and its transformation to the protease bound form," Proc. Natl. Acad. Sci. USA 85:1437–1441 (1988).
Businaro, R., et al., "Synthesis and secretion of $\alpha_2$–macroglobulin by human glioma established cell lines," Exp. Brain. Res. 88:213–218 (1992).
Cavus, I. et al., "Inhibition of Long–term Potentiation Development in rate Hippocampal Slice by $\alpha_2$ Macroglobulin, an Acute–Phase Protein in the Brain," J. Neurosci. Res. 43:282–288 (1996).
Du, Y., et al., "$\alpha_2$ Macroglobulin as a β–Amyloid Peptide–Binding Plasma Protein," J. Neurochem. 69:299–305 (1997).

(List continued on next page.)

Primary Examiner—Deborah Crouch
Assistant Examiner—Joseph Woitach
(74) Attorney, Agent, or Firm—Sterne, Kessler, Goldstein & Fox P.L.L.C.

(57) ABSTRACT

The disclosed invention relates to the finding that the A2M-2 deletion mutation, which is a predisposing factor for Alzheimer's Disease, leads to the production of altered $\alpha_2$M RNA transcripts and proteins. Based on this finding, the invention provides for new therapeutic agents for AD, including molecules having Aβ and low density lipoprotein receptor-related protein (LRP) binding domains, peptides, nucleic acid molecules, antisense oligonucleotides, and viral vectors for gene therapy. In addition, the invention relates to pharmaceutical compositions containing these therapeutic agents, methods of using these therapeutic agents to combat Alzheimer's Disease, and methods of screening for therapeutic agents that can combat Alzheimer's Disease.

24 Claims, 7 Drawing Sheets

OTHER PUBLICATIONS

Du, Y., et al., "$\alpha_2$ Macroglobulin Attenuates β–Amyloid Peptide 1–40 Fibril Formation and Associated Neurotoxicity of Cultured Fetal Rat Cortical Neurons," *J. Neurochem.* 70:1182–1188 (1998).

Feldman. S., et al., "Model of $\alpha_2$ Macroglobulin structure and function," *Proc. Natl. Acad. Sci. USA* 82:5700–5704 (1985).

Gliemann, J., "Receptors of the Low Density Lipoprotein (LDL) Receptor Family in Man. Multiple Functions of the Large Family Members via Interaction with Complex Ligands," *Biol. Chem.* 379:951–964 (1998).

Hollenbach, E. et al. "Confirmation of an association between a polymorphism in the exon 3 of the low–density lipoprotein receptor–related protein gene and Alzheimer's disease," *Neurology* 50:1905–1907 (1998).

Hughs, S.R., et al., "$\alpha_2$ macroglobulin associates with β–Amyloid peptide and prevents fibril formation," *Proc. Natl. Acad. Science. USA* 95:3275–3280 (1998).

Jinnah, H.A. and Friedmann, T., "Gene Therapy and the Brain," *British Med. Bull.* 51:138–148 (1995).

Justus, C.W.E., et, al.,"Quantification of free $\alpha_2$ macroglobulin and $\alpha_2$ macroglobulin–protease complexes by a novel ELISA system based on streptococcal $\alpha_2$ macroglobulin receptors," *J. Immunol. Methods* 126:103–108 (1990).

Kan, C., et al., "Nucleotide sequence of cDNA encoding human $\alpha_2$ macroglobulin and assignment of the chromosomal locus," *Biochemistry* 82:2282–2286 (1985).

Kang, D.E., et al., "Genetic association of the low–density lipoprotein receptor–related protein gene (LRP), an apolipoprotein E receptor, with late–onset Alzheimer's disease," *Neurology* 49:56–61 (1997).

Kolodziej, S.J., et al., "Three–Dimensional Structure of the Human Plasmin $\alpha_2$ Macroglobulin Complex," *J. Structural Biol.* 123:124–133 (1998).

Kovacs, D.M., et al., "Alpha–2–Macroglobulin–2 Allele Associated with Alzheimer's Disease: RNA and Protein Products," *A Keystone Symposium on Aging: Genetic and Environmental Influences on Lifes Spans,* Tamarron, Colorado (Feb. 1999).

Kounnas, M.Z., et al., "LDL Receptor–Related Protein, a Multifunctional ApoE Receptor, Binds Secreted β–Amyloid Precursor Protein and Mediates Its Degradation," *Cell* 82:331–340 (1995).

Kounnas, M.Z., et al.,"The Cellular Internalization and Degradation of Hepatic Lipase Is Mediated by Low Density Lipoprotein Receptor–related Protein and Requires Cell Surface Proteoglycans," *J. Biol. Chem.* 270:9307–9312 (1995).

Kounnas, M.Z. et al., "LDL Receptor–Related Protein (LPR) Binds Secreted β–Amyloid Precursor Protein and Mediates Its Degradation," *Mol. Biol. Cell* 6(*Suppl*):327A (1995).

Le Corre, S., et al., "Critical Issues in the Antisense Inhibition of Brain Gene Expression In Vivo: Experiences Targeting the 5–HT$_{1A}$ Receptor," *Neurochem. Int.* 31:349–362 (1997).

Lopes, M.B., et al., "Expression of $\alpha_2$ macroglobulin receptor/low density lipoprotein receptor–related protein is increased in reactive and neoplastic glial cells," *FEBS Lett.* 338:301–305 (1994).

Lorent, K., et al., "Expression in Mouse Embryos and in Adult Mouse Brain of the Three Members of the Amyloid Precursor Protein Family, of the Alpha–2–Macroglobulin Receptor/Low Density Lipoprotein and of its Ligands Apolipoprotein E, Lipoprotein Lipase, Alpha–2–Macroglobulin and the 40,000 Molecular Weight Receptor–Associated Protein," *Neuroscience* 65:1009–1025 (1995).

Marynen, P., et al., "A Monoclonal Antibody to a Neo–Antigen on $\alpha_2$ Macroglobulin Complexes Inhibits Receptor –mediated Endocytosis," *J. Immunol.* 127:1782–1786 (1981).

Marynen, P., et al., "A genetic polymorphism in a functional domain of human pregnancy zone protein: the bait region," *FEBS Lett.* 262:349–352 (1990).

Mattijs, G., et al., "A deletion polymorphism in the human alpha–2–macroglobulin (A2M) gene," *Nucleic Acids Res.* 19:5102 (1991).

Misra, U.K. and Pizzo, S.V., "Binding of Receptor–recognized Forms of $\alpha_2$ macroglobulin Signaling Receptor Activates Phosphatidylinositol 3–Kinase," *J. Biol. Chem.* 273:13399–13402 (1998).

Mori, T., et al., "$\alpha_2$ Macroglobulin is an astroglia–derived neurite–promoting factor for cultured neurons from rat central nervous system," *Brain Res.* 527:55–61 (1990).

Narita, M., et al., "$\alpha_2$ Macroglobulin Complexes with and Mediates the Endocytosis of β–Amyloid Peptide Via Cell Surface Low–Density Lipoportein Receptor–Related Protein," *J. Neurochem.* 69:1904–1911 (1997).

Neilsen, K.L., et al., "Identification of Residues in $\alpha_2$ Macroglobulins Important for Binding to the $\alpha_2$ Macroglobulin Receptor/Low Density Lipoprotein Receptor–related Protein," *J. Biol. Chem.* 271:12909–12912 (1996).

Poller, W., et al., "Cloning of the human $\alpha_2$ macroglobulin gene and detection of mutations in two functional domains: the bait region and the thiolester site," *Hum. Genet.* 88:313–319 (1992).

Qui, W.Q., et al., "Degradation of Amyloid β–Protein by a Serine Protease–$\alpha_2$ Macroglobulin Complex," *J. Biol. Chem.* 271:8443–8451 (1996).

Rebeck, G.W., et al., "Multiple, Diverse Senile Plaque–associated Proteins Are Ligands of an Apolipoprotein E Receptor, the $\alpha_2$ Macroglobulin Receptor/Low–Density–Lipoprotein Receptor–related Protein," *Ann. Neurol.* 37:211–217 (1995).

Selkoe, D., "Cell biology of the amyloid β–protein precursors and the mechanism of Alzheimer's disease," *Annu. Rev. Cell Biol.* 10:373–403 (1994).

Soto, C., et al., "β–Sheet breaker peptides inhibit fibrillogenesis in a rat brain model of amyloidosis: Implications for Alzheimer's therapy," *Nat. Med.* 4:822–826 (1998).

Soto, C., et al., "Inhibition of Alzheimer's Amyloidosis by Peptides That Prevent β–Sheet Conformation," *Biochem. Biophys. Res. Commun.* 226:672–680 (1996).

Sottrup–Jensen, L., et al., "Primary Structure of Human $\alpha_2$ Macroglobulin," *J. Biol. Chem.* 259:8318–8327 (1984).

Strauss, S., et al., "Detection of interleukin–6 and $\alpha_2$ Macroglobulin Immunoreactivity in Cortex and Hippocampus of Alzheimer's Disease Patients," *Lab. Invest.* 66:223–230 (1992).

Strickland, D., et al., "Sequence Identity between the $\alpha_2$-Macroglobulin Receptor and Low Density Lipoprotein Receptor–related Protein Suggests That This Molecule Is a Multifunctional Receptor," *J. Biol. Chem.* 265:17401–17404 (1990).

Strickland, D., et al., "Primary Structure of $\alpha_2$-Macroglobulin Receptor–associated Protein," *J. Biol. Chem.* 266:13364–13369 (1991).

Tanzi, R., et al., "Amyloid β Protein Gene: cDNA, mRNA, Distribution, and Genetic Linkage Near the Alzheimer Locus," *Science* 235:880–884 (1987).

Tirode, F., et al., "A Conditionally Expressed Third Partner Stabilizes or Prevents the Formation of a Transcriptional Activator in a Three–hybrid System," *J. Biol. Chem.* 272:22995–22999 (1997).

Tooyama, T., et al., "Immunohistochemical Study of $\alpha_2$-Macroglobulin Receptor in Alzheimer and Control Postmortem Human Brain," *Mol. Chem. Neuropath.* 18:153–160 (1993).

Van Gool, D., et al., "$\alpha_2$-Macroglobulin Expression in Neuritic–Type Plaques in Patients With Alzheimer's Disease," *Neurobiol. Aging* 14:233–237 (1993).

Van Leuven, F., et al., "The Receptor–binding Domain of Human $\alpha_2$-Macroglobulin," *J. Biol. Chem.* 261:11369–11373 (1986).

Wavrant–DeVrieze, F., et al., "Association between the low density lipoprotein receptor–related protein (LRP) and Alzheimer's disease," *Neurosci. Lett.* 227:68–70 (1997).

Zhang, Z., et al., Inhibition of $\alpha_2$–macroglobulin/proteinase–mediated degradation of amyloid δ peptide by apolipoprotein E and $\alpha_1$–antichymotrypsin, *Int. J. Exp. Clin. Invest.* 3:156–161 (1996).

\* cited by examiner

α-2- MACROGLOBULIN THERAPIES AND DRUG SCREENING METHODS FOR ALZHEIMER'S DISEASE.

This application is continuation in part of application Ser. No. 09/148,503, filed Sep. 4, 1998, now U.S. Pat. No. 6,342,350, which claims priority to provisional applications No. 60/057,655, filed Sep. 5, 1997, and No. 60/093,297, filed Jul. 17, 1998, all which are herein incorporated by reference.

BACKGROUND OF THE INVENTION

1. Field of the Invention

This invention relates to the field of medical genetics. More specifically, the invention provides for therapeutic agents for Alzheimer's Disease and methods of screening for therapeutic agents for Alzheimer's disease that are based on affecting alpha-2-macroglobulin function and expression.

2. Related Art

Alzheimer's disease (AD) is a devastating neurodegenerative disorder that affects more than 4 million people per year in the US (Döbeli, H., *Nat. Biotech.* 15:223–24 (1997)). It is the major form of dementia occurring in mid to late life: approximately 10% of individuals over 65 years of age, and approximately 40% of individuals over 80 years of age, are symptomatic of AD (Price, D. L., and Sisodia, S. S., *Ann. Rev. Neurosci.* 21:479–505 (1998)).

The first recognized clinical symptom of AD is usually the loss of short-term memory (Schellenberg, G. D., *Proc. Nati. Acad Sci. USA* 92:8552–559 (1995)). Other common symptoms include abnormal judgement and behavior, and difficulty with language, orientation, problem solving, calculations, and visuospacial perception (Price, D. L., and Sisodia, S. S., *Ann. Rev. Neurosci.* 21:479–505 (1998); Schellenberg, G. D., *Proc. Natl. Acad. Sci. USA* 92:8552–559 (1995)). These symptoms often worsen until cognitive function is almost entirely lost, and the patient cannot function independently (Schellenberg, G. D., *Proc. Natl. Acad. Sci. USA* 92:8552–559 (1995); Price, D. L., and Sisodia, S. S., *Ann. Rev. Neurosci.* 21:479–505 (1998)). By late stages of the disease patients typically lack verbal ability, cannot recognize people, and are incontinent and bed-ridden (Price, D. L., and Sisodia, S. S., *Ann. Rev. Neurosci.* 21:479–505 (1998); Sloane, P. D., *Am. Family Phys.* 58: 1577–86 (1998)).

Known risk factors for AD include age, genetic predisposition, abnormal protein (β-amyloid) deposition in the brain, and certain environmental factors such as head injury, hypothyroidism, and a history of depression. The majority of AD patients do not exhibit symptoms until their seventies (Price, D. L., and Sisodia, S. S., *Ann. Rev. Neurosci.* 21:479–505 (1998)). However, individuals who have inherited particular genetic defects often exhibit symptoms in midlife (Price, D. L., and Sisodia, S. S., *Ann. Rev. Neurosci.* 21:479–505 (1998)). This latter type of AD, called early-onset familial AD (FAD), accounts for 5–10% of AD cases, and has been linked to defects in three different genes, APP, PSEN1, PSEN2 (Blacker, D. and Tanzi, R. E., *Archives of Neurology* 55:294–296 (1998)). Mutations in these genes lead to increased production of the amyloidogenic β-amyloid peptide (Aβ) (Citron, M., et al, *Nature Medicine* 3:67–72 (1997); Suzuki, N., et al., *Science* 264:1336–1340 (1994)).

The most prevalent form of AD, called late-onset AD (LOAD), accounts for approximately 90% of AD cases, and has been genetically linked to APOE and LRP (Kang, D. E., et al., *Neurology* 49:56–61 (1997); Kounnas, M. Z., el al., *Cell* 82:331–340 (1995)). Recently, another gene, the alpha-2-macroglobulin gene (A2M), was found to be linked to LOAD (Blacker, D., et al., *Nature Genetics* 19:357–360 (1998)). Carriers of a particular mutation in A2M were discovered to be at increased risk of AD. This mutation is a pentanucleotide deletion at the 5' splice site of the second exon encoding the bait region of alpha-2-macroglobulin ($\alpha_2$M), and is referred to as the A2M-2 genotype. The A2M-2 genotype is present in 30% of the population (Blacker, D., et al., *Nature Genetics* 19:357–360 (1998)). The A2M-2 pentanucleotide deletion is a predisposing factor for AD.

Presently, there is no cure for AD on the horizon and its incidence is increasing as the population ages (Price, D. L., and Sisodia, S. S., *Ann. Rev. Neurosci.* 21:479–505 (1998)). Due to the lateness in life of the onset of AD symptoms, the ability to delay onset by as little as 5 years could decrease the number of AD patients by as much as 50% (Marx, J., *Science* 273:50–53 (1996)). With the large number of people already affected, and projected to be affected by AD, a drug that could merely delay the onset of AD would be very valuable.

Therapeutic agents based on predisposing factors of AD might be able to prevent, delay or slow progression of the disease. However, presently, available treatments are primarily aimed at treatment of the symptoms of the disease (Enz, A., "Classes of drugs," in: Pharmacotherapy of Alzheimer's Disease, Gauthier, S., ed., Martin Dunitz, publ., Malden, Mass. (1998)). These AD drugs offer only modest success, and at most, merely slow the progression of the disease (Delagarza, V. W., *Am. Family Phys.* 58:1175–1182 (1998); Enz, A., "Classes of drugs," in: Pharmacotherapy of Alzheimer's Disease, Gauthier, S., ed., Martin Dunitz, publ., Malden, Mass. (1998)). Presently approved and investigational drugs for treating AD can be characterized as those whose actions enhance neurotransmitter effect, or those believed to protect neurons (Delagarza, V., *Am. Family Phys.* 58:1175–1182 (1998)). The most well known drugs in the first category are the cholinesterase inhibitors, such as tacrine (Cognex™) and donepezil (Aricept™), both of which have been approved by the FDA (Delagarza, V., *Am. Family Phys.* 58:1175–1182 (1998); Sloan, P., *Am. Family Phys.* 58:1577–1586 (1998)). Tacrine and donepezil are only modestly effective (Sloan, P., *Am. Family Phys.* 58:1577–1586 (1998)), and are associated with unpleasant side effects including nausea and vomiting (Delagarza, V., *Am. Family Phys.* 58:1175–1182 (1998)). Several neuroprotective drugs are under investigation for the treatment of AD, including estrogen, vitamin E, selegiline and non-steroidal anti-inflammatory drugs (NSAIDs) (Sloan, P., *Am. Family Phys.* 58:1577–1586 (1998); Delagarza, V., *Am. Family Phys.* 58:1175–1182 (1998)). None of these drugs have been approved yet for the treatment of AD, and each has significant drawbacks, including negative side-effects, or association with increased risk of other diseases. (Sloan, P., *Am. Family Phys.* 58:1577–1586 (1998); Delagarza, V., *Am. Family Phys.* 58:1175–1182 (1998); Enz, A., "Classes of drugs," in: Pharmacotherapy of Alzheimer's Disease, Gauthier, S., ed., Martin Dunitz, publ., Malden, Mass. (1998)).

Thus, there is a need for new AD therapeutic agents, especially those based on predisposing factors of AD. In addition, there is a need for drug screening systems to aid in developing these therapeutic agents.

SUMMARY OF THE INVENTION

Based on the finding, described herein, that the A2M-2 deletion leads to the production of altered $\alpha_2$M RNA transcripts and proteins, strategies aimed at replacing or supplementing normal $\alpha_2M$ function and activities, and/or at suppressing defective $\alpha_2M$ function in the brain may serve as a means for therapeutically preventing, treating, or even reversing AD neuropathogenesis. In addition, these strategies may be useful for treating other pathologies associated with defective $\alpha_2M$ function. Moreover, methods described herein may be used to screen for these therapeutic agents. Thus, the invention provides for new therapeutic agents for AD, for pharmaceutical compositions containing these therapeutic agents, for methods of using these therapeutic agents, and for methods of screening for these therapeutic agents.

The first aspect of the invention is to provide for a therapeutic agent for Alzheimer's Disease, where the agent can replace or supplement α2M function, or can suppress the expression of A2M-2. A molecule that can bind to Aβ and to LRP may be able to promote clearance of Aβ through LRP mediated endocytosis. Thus, one embodiment of the invention is an anti-LRP-Aβ molecule having an Aβ binding domain, and an LRP binding domain. In a preferred embodiment of the invention, this molecule is a peptide.

In one embodiment of the invention the peptide is an anti-LRP-Aβ peptide having an Aβ binding domain composed of 10–50 contiguous residues of SEQ ID NO:6, and an LRP binding domain comprising 10–50 contiguous residues of SEQ ID NO:8, which encompass residues 1366–1392 of SEQ ID NO:8. In another embodiment of the invention, the anti-LRP-Aβ peptide has an Aβ binding domain with an amino acid sequence selected from the group consisting of SEQ ID NO:6, SEQ ID NO:12, SEQ ID NO:16, SEQ ID NO:18, SEQ ID NO:20, SEQ ID NO:22, SEQ ID NO:24, and SEQ ID NO:26; and an LRP binding domain composed of the amino acid sequence of SEQ ID NO:10. In yet another embodiment of the invention, the anti-LRP-Aβ peptide has an Aβ binding domain with an amino acid sequence selected from the group consisting of SEQ ID NO:12, SEQ ID NO:16, SEQ ID NO:18, SEQ ID NO:20, SEQ ID NO:22, SEQ ID NO:24, and SEQ ID NO:26; and an LRP binding domain composed of 10–50 contiguous residues of SEQ ID NO:8.

The Aβ binding domain may be connected to the LRP binding domain of the anti-LRP-Aβ molecule by a covalent bond, linker molecule, or linkerless polyethylene glycol. In a preferred embodiment, the Aβ and LRP binding domains are connected by a peptide bond. In another preferred embodiment of the invention, the Aβ and LRP binding domains are connected by a peptide composed of 1–20 glycine residues.

In another embodiment, the anti-LRP-Aβ peptide has the amino acid sequence of SEQ ID NO:14. Alternatively, the anti-LRP-Aβ peptide has an Aβ binding domain having an amino acid sequence selected from the group consisting of SEQ ID NO:6, SEQ ID NO:12, SEQ ID NO:16, SEQ ID NO:18, SEQ ID NO:20, SEQ ID NO:22, SEQ ID NO:24, and SEQ ID NO:26; an LRP binding domain having the amino acid sequence of SEQ ID NO:10; and a linker connecting the Aβ binding domain to the LRP binding domain.

In addition, the invention provides for pharmaceutically acceptable salts of the anti-LRP-Aβ peptide and for nucleic acid molecules encoding the anti-LRP-Aβ peptide.

Another embodiment of the invention relates to a nucleic acid molecule encoding an anti-LRP-β peptide, where the Aβ binding domain is encoded by 30–150 contiguous nucleotides of SEQ ID NO:5, and the LRP binding domain is encoded by 30–150 contiguous nucleotides of SEQ ID NO:7. In another embodiment of the invention, the region of the nucleic acid molecule encoding the Aβ binding domain has a nucleotide sequence selected from the group consisting of SEQ ID NO:5, SEQ ID NO:11, SEQ ID NO:15, SEQ ID NO:17, SEQ ID NO:19, SEQ ID NO:21, SEQ ID NO:23, and SEQ ID NO:25; and the region encoding the LRP binding domain has the nucleotide sequence of SEQ ID NO:9. In yet another embodiment of the invention, the region of the nucleic acid molecule encoding the Aβ binding domain has a nucleotide sequence selected from the group consisting of SEQ ID NO:11, SEQ ID NO:15, SEQ ID NO:17, SEQ ID NO:19, SEQ ID NO:21, SEQ ID NO:23, and SEQ ID NO:25; and the region encoding the LRP binding domain is encoded by 30–150 contiguous nucleotides of SEQ ID NO:7. In another embodiment of the invention, the nucleic acid molecule has the nucleotide sequence of SEQ ID NO:13.

The region encoding the Aβ binding domain may be connected to the region encoding the LRP binding domain of the nucleic acid molecule by a phosphodiester bond. Alternatively, these regions may be connected by a nucleotide encoding a linker peptide. In a preferred embodiment of the invention, the connecting nucleotide encodes 1–20 glycine residues.

In addition, the invention relates to nucleic acid molecules having at least 95% homology to these nucleic acid molecules.

Another embodiment of the invention relates to a nucleic acid molecule that is a first polynucleotide that hybridizes to a second polynucleotide that is complementary to the nucleic acid molecules described above. In another embodiment of the invention, the nucleic acid molecule is a first polynucleotide that hybridizes to a second polynucleotide that is complementary to the nucleotide sequence of SEQ ID NO:13. In yet another embodiment of the invention, the hybridizing conditions for the hybridization of the first and second polynucleotides are as follows: (a) incubate overnight at 42° C. in a solution consisting of 50% formamide, 5×SSC, 50 mM sodium phosphate (pH 7.6), 5×Denhardt's solution, 10% dextran sulfate, and a 20 μg/ml denatured, sheared salmon sperm DNA; and (b) wash at 65° C. in a solution consisting of 0.1×SSC.

A related embodiment of the invention is a pharmaceutical composition containing an anti-LRP-Aβ molecule, and one or more pharmaceutically acceptable carriers. In addition, the invention provides for a pharmaceutical composition containing an anti-LRP-Aβ peptide, or a pharmaceutically acceptable salt thereof. In a preferred embodiment, the pharmaceutical composition contains an anti-LRP-Aβ peptide having an amino acid sequence selected from the group consisting of SEQ ID NO:4 or SEQ ID NO:14, or a pharmaceutically acceptable salt thereof, and one or more pharmaceutically acceptable carriers. The invention also relates to a method of combating Alzheimer's Disease in a subject by administering an anti-LRP-Aβ molecule, or a pharmaceutically acceptable salt thereof. In a preferred embodiment, the anti-LRP-Aβ molecule is a peptide. In another preferred embodiment, the anti-LRP-Aβ peptide is a polypeptide having an amino acid sequence selected from the group consisting of SEQ ID NO:4 or SEQ ID NO:14, or a pharmaceutically acceptable salt thereof.

The invention also relates to an A2M-2 antisense oligonucleotide designed to target A2M-2 RNA. In one preferred embodiment of the invention, the A2M-2 antisense oligonucleotide is designed to target A2M-2 heteronuclear RNA.

In another preferred embodiment, the A2M-2 antisense oligonucleotide is designed to target A2M-2 mRNA. In one embodiment of the invention, the A2M-2 antisense oligonucleotide designed to target A2M hnRNA has the nucleotide sequence of SEQ ID NO:27. The A2M-2 antisense oligonucleotide is preferably from 8–50 nucleotides in length, and more preferably is 15–30 nucleotides in length, and is most preferably 15 nucleotides in length. Thus, in another preferred embodiment of the invention an A2M-2 antisense oligonucleotide designed to target A2M-2 hnRNA has the nucleotide sequence of the last 15–30 contiguous nucleotides of SEQ ID NO:27. In another embodiment of the invention the A2M-2 antisense oligonucleotide designed to target A2M-2 has the sequence of nucleotides 36–50 of SEQ ID NO:27 or of nucleotides 20–50 of SEQ ID NO:27. The invention also relates to a pharmaceutical composition containing an A2M-2 antisense oligonucleotide, and one or more pharmaceutically acceptable carriers. In addition, the invention relates to a method of combating Alzheimer's Disease in a subject by administering the A2M-2 antisense oligonucleotide.

The invention also provides for a viral vector carrying a transgene encoding $\alpha_2M$, or an anti-LRP-A$\beta$ peptide. in a preferred embodiment of the invention, the viral vector carries a gene encoding $\alpha_2M$. In another preferred embodiment of the invention, the gene encoding $\alpha_2M$ has the nucleotide sequence of nucleotides 44–4465 of SEQ ID NO:1. The invention also relates to a viral vector carrying a gene encoding an anti-LRP-A$\beta$ peptide. In another preferred embodiment of the invention, the viral vector is an adeno-associated virus. In addition, the invention provides for a pharmaceutical composition containing the viral vector, and one or more pharmaceutically acceptable carriers, and for a method of combating Alzheimer's Disease in a subject by administering the viral vector.

The second aspect of the invention is to provide for a method of screening for therapeutic agents for Alzheimer's Disease that can replace or supplement $\alpha 2M$ function, or can suppress the expression of A2M-2. One embodiment of the invention is a method of screening for a therapeutic agent for AD by incubating a cell that is heterozygous or homozygous for the A2M-2 allele in the presence of a test agent, and then determining whether the ratio of normal to aberrant A2M mRNA has increased relative to the ratio of normal to aberrant A2M mRNA found in cells untreated with the test agent. In one preferred embodiment of this method, the cells are glioma cells. In another preferred embodiment, the cells are hepatoma cells. In yet another preferred embodiment of the invention, the cells are heterozygous for the A2M-2 allele.

In a related embodiment of this method, S1 nuclease is used to determine the ratio of normal to aberrant A2M mRNA, and the probe used is complementary to a nucleotide encoding A2M (SEQ ID NO:1). Thus, in one embodiment of the invention, S1 nuclease analysis using a probe complementary to SEQ ID NO:1, where the probe encompasses nucleotides 2057–2284 of SEQ ID NO:1, is used to determine whether the ratio of normal to aberrant A2M mRNA has increased. In a preferred method of the invention, the probe used in the S1 nuclease analysis is 300 bp long. In another embodiment of the invention, the probe used in the S1 nuclease analysis is complementary to nucleotides 2024–2323 of SEQ ID NO:1.

Alternatively, RT PCR analysis is used to determine whether the ratio of normal to aberrant A2M mRNA has increased. In a preferred method of RT PCR analysis, the primers are designed to amplify a region of A2M encompassing exons 17–18. In a more preferred method of RT PCR analysis, the amplified region of A2M encompassing exons 17–18 is 300 bp long. In another embodiment of the invention, the primers used for the RT PCR analysis are designed to amplify nucleotides 2052–2289 of SEQ ID NO:1. Another embodiment of the invention relates to the use of a first primer having a nucleotide sequence complementary to nucleotides 2024–2038 of SEQ ID NO:1, and a second primer having the nucleotide sequence of nucleotides 2309–2323 of SEQ ID NO:1 for the RT PCR analysis.

The invention also provides for a method of screening for a therapeutic agent for Alzheimer's disease by incubating $\alpha_2M$ with a test agent, and then determining whether the treated $\alpha_2M$ has undergone a conformational change, or determining whether the treated $\alpha_2M$ can bind to LRP. In a preferred embodiment of the invention, the $\alpha_2M$ treated with a test agent is tetrameric $\alpha_2M$. In another preferred embodiment of the invention, an $\alpha_2M$ electrophoretic mobility assay is ued to determine whether the treated $\alpha_2M$ has undergone a conformational change. In another embodiment of the invention, an ELISA is used to determine whether the treated $\alpha_2M$ can bind to LRP. In a related embodiment of the invention, the ELISA includes the following steps in sequential order: incubating LRP in a well coated with anti-LRP IgG, incubating the well with treated $\alpha_2M$, incubating the well with anti-$\alpha_2M$ IgG conjugated to an enzyme, and incubating the well with a substrate for the enzyme. In an alternative embodiment, the ELISA includes the following steps in sequential order: incubating a well coated with LRP with treated $\alpha_2M$, incubating the well with anti-$\alpha_2M$ IgG conjugated to an enzyme, and incubating the well with the substrate for the enzyme. In another embodiment, the ELISA includes the following steps in sequential order: incubating treated $\alpha_2M$ in a well coated with an anti-$\alpha_2M$ IgG specific for activated $\alpha_2M$, incubating the well with an anti-$\alpha_2M$ IgG conjugated to an enzyme, and incubating the well with a substrate for the enzyme. In another embodiment of the invention, immunoblotting with anti-LRP IgG and anti-$\alpha_2M$ IgG is used to determine whether the treated $\alpha_2M$ can bind to LRP. In yet another embodiment of the invention, a test for the ability of the treated $\alpha_2M$ to undergo LRP mediated endocytosis is used to determine whether the treated $\alpha_2M$ can bind to LRP. In another embodiment of the invention, a test for the ability of the treated $\alpha_2M$ to undergo LRP mediated degradation is used to determine whether the treated $\alpha_2M$ can bind to LRP.

BRIEF DESCRIPTION OF THE FIGURES

FIG. 1 is an autoradiograph depicting the results of $^{33}$P-labeled $\alpha_2M$ mRNA transcripts from A2M from human glioma cell lines that express either wild-type A2M ((Blacker, D., et al., *Nat. Genet.* 19:357–360 (1998)) or are heterozygous for the A2M-2 deletion allele obtained by RT-PCR, and separated on a polyacrylamide gel. A2M-1/2 lines are indicated as lanes marked "2", A2M-1/1 lines are indicated as lanes marked "1."

FIG. 2 is a schematic representation of four of the altered A2M transcripts produced by human glioma cell lines expressing the A2M-2 allele.

FIG. 3 is a photograph of immunoblots of media and extracts from CHO cells transfected with $\alpha_2M$ truncated after exon 18 that were probed with an anti-$\alpha_2M$ antibody. The anti-$\alpha_2M$ antibody detected truncated $\alpha_2M$ in transfected CHO cells. Panel A: cell lysate; Panel B: media; (−) indicates samples from untransfected cells; (wt) indicates samples from cells transfected with full-length $\alpha_2M$ construct; (Δ) indicates samples from cells transfected with the α$_2$M construct truncated after exon 18; m, d and t indicate monomer, dimer and trimer forms of the truncated protein, respectively. These forms of wild type α$_2$M are also visible but not marked.

FIG. 4 is a photograph of an immunoblot from cell lysates from wild-type cells (A2M-1) (lane labeled 1/1) and cells heterozygous for the A2M-2 deletion (lanes labeled 1/2) probed with an anti-α$_2$M antibody. The lane labeled (+) indicates lysate from CHO cells transfected with full length α$_2$M, and probed with an anti-α$_2$M antibody. The media (data not shown) from A2M-1 and A2M-2 cells contained primarily full-length α$_2$M monomers, but in the media from the A2M-2 cells, small amounts of truncated species could also be observed (data not shown).

FIG. 5 depicts the α$_2$M conformational change induced by protease (represented by the letter P in a circle) cleavage. Note the exposure of the LRP binding domain (represented by □) after the conformational change.

FIG. 6 depicts one possible amino acid sequence (SEQ ID NO: 14 for the anti-LRP-Aβ polypeptide.

FIG. 7 is a schematic of the yeast three-hybrid system for detecting the anti-LRP-Aβ peptide binding to Aβ and LRP.

DETAILED DESCRIPTION OF THE PREFERRED EMBODIMENTS

Definitions

Figure 1:
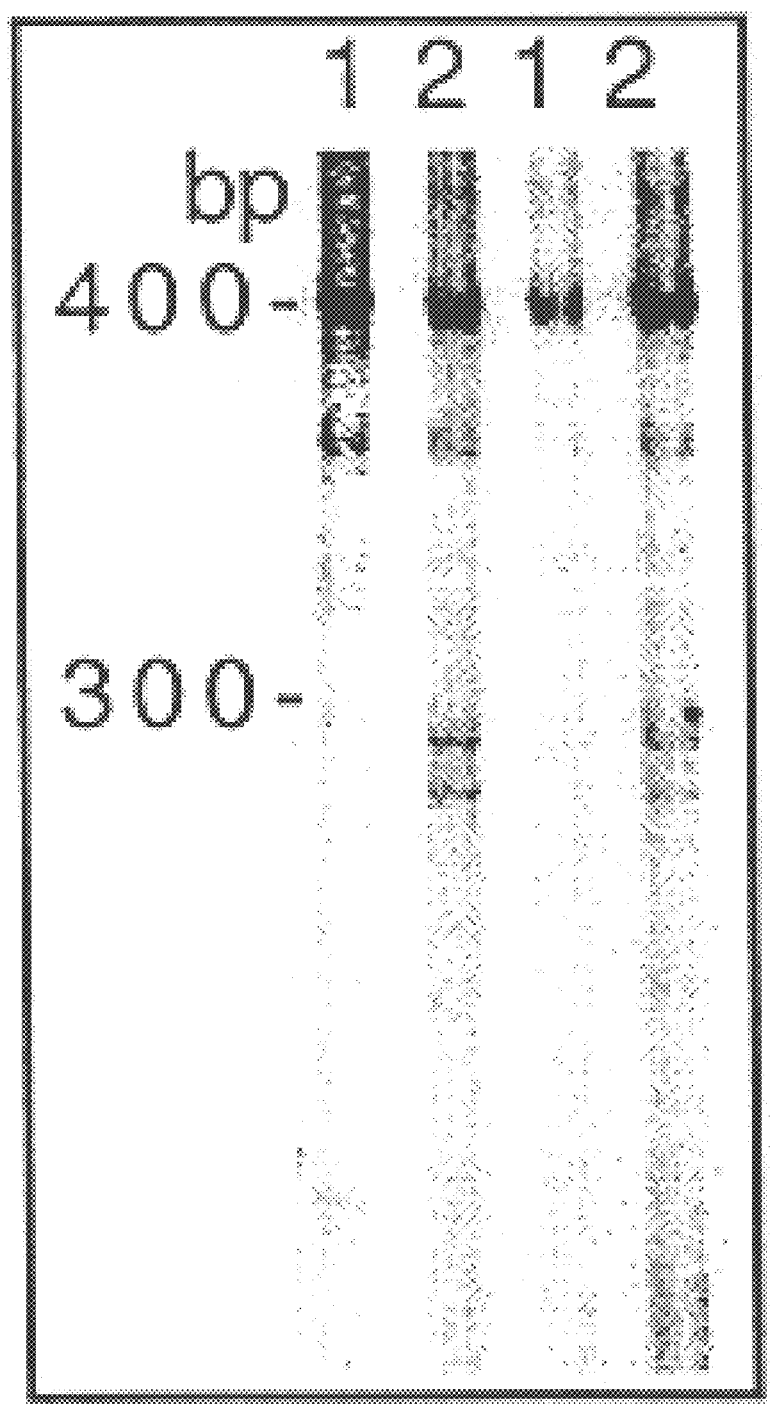
FIG. 1.

In the description that follows, a number of terms used in recombinant DNA technology, molecular and cell biology, and pharmacology are extensively used. To provide a clearer and consistent understanding of the specification and claims, including the scope to be given such terms, the following definitions are provided.

Nucleotide: "Nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Polynucleotide: A "polynucleotide" is a linear polymer of nucleotides linked by phosphodiester bonds between the 3' position of one nucleotide and the 5' position of the adjacent nucleotide.

Oligonucleotide: "Oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms in that they may exhibit enhanced cellular uptake, increased stability in the presence of nucleases, and other features which render them more acceptable as therapeutic or diagnostic reagents.

Nucleic acid molecule: By "nucleic acid molecule" is meant a polymeric molecule composed of nucleotides.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Complementary: As used herein, "complementary" refers to the subunit sequence complementarity between two nucleic acids, for example, two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 60%) of corresponding positions in each of the molecules are occupied by nucleotides which normally base pair with each other (for example, A:T and G:C nucleotide pairs).

Hybridization: The terms "hybridization" and "specifically hybridizes to" refer to the pairing of two complementary single-stranded nucleic acid molecules (RNA and/or DNA) to give a double-stranded molecule. These terms are used to indicate that the nucleotides are sufficiently complementary such that stable and specific binding occurs between the DNA or RNA target and the oligonucleotide. It is understood that an oligonucleotide need not be 100% complementary to its target nucleic acid sequence to be specifically hybridizable. An oligonucleotide specifically hybridizes to another when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i. e., under physiological conditions in the case of in vivo assays or therapeutic treatment, or, in the case of in vitro assays, under conditions in which the assays are conducted.

Primer: As used herein "primer" refers to a single-stranded oligonucleotide that is extended by covalent bonding of nucleotide monomers during amplification or polymerization of a DNA molecule. Minisatellite primers used for the amplification of minisatellite dimer, trimer, tetramer, etc., sequences are well-known in the art.

Template: The term "template" as used herein refers to a double-stranded or single-stranded nucleic acid molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to the template or a portion thereof. The newly synthesized DNA molecule, according to the invention, may be equal or shorter in length than the original DNA template. Mismatch incorporation or strand slippage during the synthesis or extension of the newly synthesized DNA molecule may result in one or a number of mismatched base pairs. Thus, the synthesized DNA molecule need not be exactly complementary to the DNA template.

Amplification: As used herein "amplification" refers to any in vitro method for increasing the number of copies of a nucleotide sequence with the use of a DNA polymerase. Nucleic acid amplification results in the incorporation of nucleotides into a DNA or molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5 to 100 "cycles" of denaturation and synthesis of a DNA molecule.

95%, 96%, 97%, 98% or 99% Homology: By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Polypeptide: A polypeptide is a polymer composed of amino acid monomers joined by peptide bonds.

Peptide Bond: A peptide bond is a covalent bond between two amino acids in which the alpha-amino group of one amino acid is bonded to the alpha-carboxyl group of the other amino acid.

Isolated nucleic acid molecule or polypeptide: a nucleic acid molecule, DNA or RNA, or a polypeptide, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules or polypeptides according to the present invention further include such molecules produced synthetically.

Linker: By "linker" is intended a molecule that connects the LRP binding domain to the Aβ binding domain of the anti-LRP-Aβ molecule. When referring to a linker composed of amino acid residues, linker is used to refer to the amino acid residues connecting the two domains. When referring to a nucleic acid encoding a linker, linker refers to the nucleotide sequence encoding the linking amino acid residues. Where the linker is composed of amino acid residues, it will typically consist of one or more glycine residues, or the nucleotide sequence encoding these residues, however, proline may also be used.

Combating Alzheimer's Disease: The term "combating Alzheimer's Disease" is intended to mean a slowing, delaying, or even reversing the AD process. Thus, for example, the therapeutic agents of the invention may be administered either therapeutically in a patient where symptoms of AD are present, or prophylactically, in a subject at risk of developing AD.

Pharmaceutically acceptable carrier: By pharmaceutically acceptable carrier is meant a non-toxic solid, semisolid or liquid filler, diluent, encapsulating material, or formulation auxiliary of any type.

Performed in sequential order: By "performed in sequential order" is intended that the steps described by this term are performed in the order that the steps are recited, but that other unrecited steps may be performed in between the recited steps.

Test agent: By "test agent" is meant any molecule that is of interest for the treatment or prevention of AD, and is to be tested using the screening methods of the invention.

Ranges: various ranges of numbers are described herein. When a range is used, the range of numbers is meant to be inclusive of the boundary numbers. For example, an oligonucleotide composed of nucleotides 20–50 of SEQ ID NO:27, is meant to include nucleotides 20, and 50 and every nucleotide in between.

Other terms used in the fields of recombinant DNA technology, molecular and cell biology, and pharmacology as used herein will be generally understood by one of ordinary skill in the applicable arts.

Alpha-2-macroglobulin

Alpha-2-Macroglobulin ($\alpha_2$M) is a 718 kD glycoprotein found at high concentrations in the serum (Borth, W., *FASEB J.* 6:3345–3353 (1992)). The structure of $\alpha_2$M consists of four identical 180 kD monomeric units, of 1451 amino acids each (Sottrup-Jensen, L., et al., *J. Biol. Chem.* 259:8318–8327 (1984)). Disulfide bonds link these monomers into dimers, and noncovalent interactions between dimers lead to formation of the functional homotetramer (Harpel, P. C., *J. Exp. Med.* 138:508–521 (1973); Swenson, R. P. and Howard, J. B., *J. Biol. Chem.* 254:4452–4456 (1979)). In addition to the ability to bind Aβ, $\alpha_2$M binds a variety of polypeptides (proteases, growth factors, and cytokines) and ions (Zn, Cu, Fe)(Borth, W., *FASEB J.* 6:3345–3353 (1992); James, K., *Immunol. Today* 11:163–166 (1990); Parisi, A. F. and Vallee, B. L., *Biochem.* 9:2421–2426 (1970)).

Figure 5:
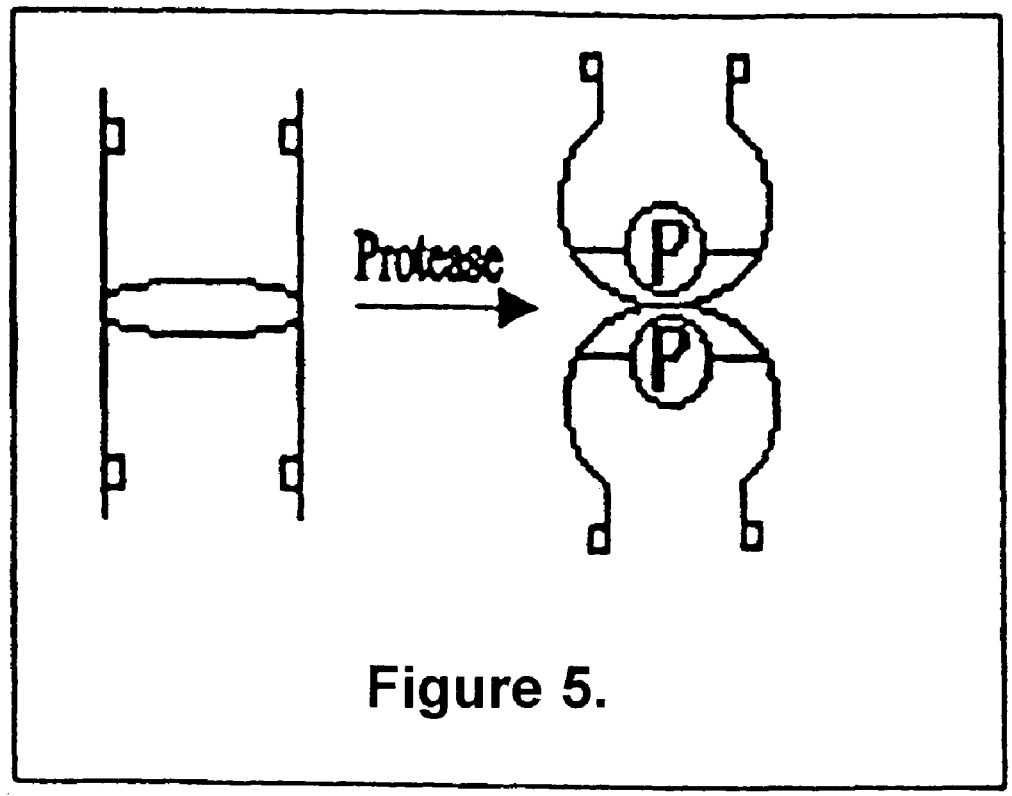
FIG. 5.

The best studied function of $\alpha_2$M is its pan-protease inhibitory activity (Barret, A. J. and Starkey, P. M., *Biochem. J.* 133:709–724 (1973)). A protease molecule binds the bait region of a $\alpha_2$M tetramer, amino acids 666–706, and cleaves any of a number of susceptible peptide bonds in this region ((Harpel, P. C., *J. Exp. Med.* 138:508–521 (1973); Barret, A. J. and Starkey, P. M., *Biochem. J.* 133:709–724 (1973); Sottrup-Jensen, L., et al, *J. Biol. Chem.* 264:15781–15789 (1989)). Protease binding and cleavage triggers a large conformational change in the $\alpha_2$M/protease complex, referred to as activation, that ultimately results in entrapment of the protease within the tetramer (FIG. 5) (Borth, W., *FASEB J.* 6:3345–3353 (1992)). In each monomer a unique P-Cys-γ-Glu thiol ester bond exists between Cys-949 and Glu-952(Borth, W., *FASEB J.* 6:3345–3353(1992)). Upon activation this thiol ester bond emerges from a hydrophobic environment and can undergo nucleophilic attack, for example, by lysine residues from the reacting proteases. The result of this nucleophilic attack is a covalent bond between Glu-952 of $\alpha_2$M and surface lysine residues of the protease (FIG. 5). The protease is effectively trapped, unable to dissociate from $\alpha_2$M but still able to cleave small peptide substrates (Qui, W. Q., et al., *J. Biol. Chem.* 271:8443–8451 (1996)). Protease-mediated activation results in exposure of the $\alpha_2$M receptor/low density lipoprotein receptor-related protein binding domain (FIG. 5) (Strickland, D., et al., *J. Biol. Chem.* 265:17401–17404 (1990)). Low density lipoprotein receptor-related protein (LRP) is a 600 kD endocytic membrane-bound receptor belonging to the low-density lipoprotein receptor family (Borth, W., *FASEB J.* 6:3345–3353 (1992)). LRP is a multifunctional receptor, because it binds ligands from different classes (Kounnas, M. Z., et al., *Cell* 82:331–340 (1995)). Exposure of this LRP binding domain is a prerequisite for LRP mediated endocytosis of $\alpha_2$M/ligand complexes and targeted degradation (Borth, W., *FASEB J.* 6:3345–3353 (1992)). In summary, $\alpha_2$M serves to bind a number of protein substrates, including Aβ, and target them for internalization and degradation.

$\alpha_2$M binds Aβ specifically and tightly. The AD binding region of α2M is located between residues 1202–1312, approximately 600 residues C-terminal to the bait region (Hughes, S. R., et al., *Proc. Natl. Acad. Sci. USA* 95:3275–3280 (1998)). Binding does not require $\alpha_2$M activation and binding stoichometry is approximately 1.1 Aβ/mol of $\alpha_2$M (Du, Y. et al., *J. Neurochem.* 69:299–305 (1997)). The apparent dissociation constant ($K_D$) for the Aβ/$\alpha_2$M complex has been reported as $3.8*10^{-10}$ M for $\alpha_2$M/$^{125}$I-Aβ (Du, Y., et al., *J. Neurochem.* 69:299–305 (1997)) and $3.5*10^{-7}$ M for biotinAβ/(ruthenium (II) tris-bipyridine-n-hydroxysuccinimide ester) modified-$\alpha_2$M (Hughes, S. R., et al., *Proc. Natl. Acad. Sci. USA* 95:3275–3280 (1998)). Despite this discrepancy in $K_D$ values (which are most likely due to methodological differences), a strong interaction between Aβ and $\alpha_2$M exists. This interaction prevents Aβ fibril formation and fibril associated neurotoxicity ((Hughes, S. R., et al., *Proc. Natl. Acad. Sci. USA* 95:3275–3280 (1998); Du, Y., et al., *J. Neurochem.* 70:1182–1188 (1998)). Recently, it has been demonstrated that a region of $\alpha_2$M encompassing only the Aβ and LRP binding domains is sufficient for Aβ binding in vivo ((Hughes, S. R., et al., *Proc. Natl. Acad. Sci. USA* 95:3275–3280 (1998)). These data suggest that the Aβ binding domain is an independent structural unit and successful $\alpha_2$M/Aβ interaction may only rely on a few key interactions. Recent work by Soto and colleagues show that an eleven residue peptide is capable of binding Aβ and inhibiting Aβ fibril formation (Soto, C., et al., *Nature Medicine* 4:822–826 (1998)), supporting the idea that only a few key interactions are needed to bind Aβ. In summary, $\alpha_2$M can mediate the catabolism of Aβ in a LRP dependent process.

A2M-2 Genotype

The A2M-2 genotype, which is linked to late-onset AD, is present in 30% of the population (Blacker, D., et al., *Nature Genetics* 19:357–360 (1998)). This genotype has a pentanucleotide deletion at the 5' splice site of the second exon encoding the bait region of $\alpha_2$M (exon 18) (Blacker, D., et al., *Nature Genetics* 19:357–360 (1998)).

Low resolution X-ray data and biochemical data suggest that the bait regions are located at the dimer interface and are crucial for the formation of functional tetramers, and the mediation of the conformational change that accompanies activation (Andersen, G. R., et al., *J. Biol. Chem.* 270:25133–25141 (1995); Bowen, M. E. and Gettins, P. G. W., *J. Biol. Chem.* 273:1825–1831 (1998)). The A2M-2 deletion in the bait region could prevent Aβ clearance and degradation if (i) proteases can not cleave the altered bait region, (ii) protease-induced activation cannot occur, (iii) LRP binding is disrupted, and/or (iv) Aβ binding is disrupted.

Low Density Lipoprotein Receptor-Related Protein

LRP is a 600 kD endocytic membrane-bound receptor belonging to the low-density lipoprotein receptor family (Borth, W., *FASEB J.* 6:3345–3353 (1992)). LRP is expressed in a variety of cell types including: adipocytes, astrocytes, fibroblasts, hepatocytes, macrophages, monocytes, and syncytiotrophoblasts. LRP is translated as a 4525 residue single chain precursor (Nielsen, K. L., et al., *J. Biol. Chem.* 271:12909–12912 (1996)). It is then processed into a 515 kD A chain and an 85 kD β chain. The β chain possesses a single transmembrane segment and a cytoplasmic tail containing two copies of the NPXY endocytosis signal sequence (Nielsen, K. L., et al., *J. Biol. Chem.* 271:12909–12912 (1996)). The extracellularly located α chain contains four cysteine-rich LDL receptor ligand-binding repeats flanked by epidermal growth factor (EGF) repeats (Nielsen, K. L., et al., *J. Biol. Chem.* 271:12909–12912 (1996)). The noncovalent association of the a chain with the extracellular portion of the β chain forms a functional LRP (Borth, W., *FASEB J.* 6:3345–3353 (1992)). LRP is a multifunction receptor because it binds ligands from different classes (Kounnas, M. Z., et al., *Cell* 82:331–340 (1995)). These include $\alpha_2$M-protease complexes, plasminogen activator inhibitor-plasminogen activator complexes, lipoprotein lipase, apoe, bovine pancreatic trypsin inhibitor, lactoferrin, Pseudomonas, exotoxin A, nexin-1 complexes, and receptor associated protein (RAP) (Kounnas, M. Z., et al., *Cell* 82:331–340 (1995)). Most of these ligands do not compete for the same binding site. RAP, however, inhibits the binding of all these ligands.

$\alpha_2$M/LRP Association

The association of activated $\alpha_2$M and LRP is highly pH dependent, acidification to pH 6.8 or below abolishes binding (Borth, W., *FASEB. J.* 6:3345–3353 (1992)). This suggests that upon endocytosis $\alpha_2$M dissociates from LRP. After endocytosis $\alpha_2$M and its associated ligands are degraded in the lysosome and LRP is recycled to the membrane (Borth, W., *FASEB J.* 6:3345–3353 (1992)). The half-life for internalization and degradation varies between 15 and 60 minutes (Borth, W., *FASEB J.* 6:3345–3353 (1992)).

The $\alpha_2$M-protease binding site of LRP has been mapped to residues 776–1399 of the β chain (Nielsen, K. L., et al., *J. Biol. Chem.* 271:12909–12912 (1996)). This region includes EGF repeats 4–6 and LDL receptor ligand binding repeats 3–10. The LRP binding domain of $\alpha_2$M is located between residues 1312 and 1451, directly C-terminal to the Aβ binding domain (Hughes, S. R., et al., *Proc. Natl. Acad. Sci. USA* 95:3275–3280 (1998)). This domain is very flexible relative to the core of $\alpha_2$M (Andersen, G. R., et al, *J. Biol. Chem.* 270:25133–25141 (1995)). Low resolution crystal structures (10 Å) indicate that activated $\alpha_2$M is roughly the shape of an H and the LRP binding domains are located at the tips of the H (FIG. 5) (Andersen, G. R., et al., *J. Biol. Chem.* 270:25133–25141 (1995)). A LRP consensus binding sequence has been proposed based on 31 LRP ligands from 7 different protein families (Nielsen, K. L., et al., *J. Biol. Chem.* 271:12909–12912 (1996)). This 27 residue consensus sequence is located between residues 1365 and 1393 of human $\alpha_2M$. Once again, experimental evidence suggests that a few key interactions may be important in LRP/$\alpha_2M$ binding. Mutations at positions 5 and 10 of the consensus sequence, corresponding to Lys-1370 and Lys-1374 in the human $\alpha_2M$, abolish binding unlike mutations at other highly conserved residues.

Implication of $\alpha_2$ in Alzheimer's Disease

Cerebral deposition of amyloid is a central event in AD (Soto, C., et al., *Nat. Med.* 4:822–826 (1998)). Genetic, neuropathological, and biochemical evidence indicate that inappropriate deposition of amyloid plays a fundamental role in the pathogenesis of AD. The major component of AD amyloid plaques is A$\beta$, a 39–43 amino acid peptide. A$\beta$ polymerizes as dense (amyloid plaque) and diffuse extracellular deposits in the neuropil (Masters, C. L., et al., *Proc. Natl. Acad. Sci. USA* 82:4245–4249 (1985)), and in cerebral blood vessels (congophilic angiopathy) (Glenner, G. G. and Wong, C. W., *Biochem. Biophys. Res. Comm.* 120:885–890 (1984)) of both AD and Down syndrome (DS) patients. Soluble A$\beta$ is found in the cerebrospinal fluid (CSF) and is produced (Haass, C., et al., *Nature* 359:322–325 (1992); Seubert, P., et al., *Nature* 359:325–327 (1992); Shoji, M., et al., *Science* 258:126–129 (1992)) by constitutive cleavage of its transmembrane parent molecule, the amyloid protein precursor (APP) (Kang, J., et al., *Nature* 325:733–736 (1987); Goldbarger, D., et al., *Science* 235:877–880 (1987); Robakis, N. K., et al., *Proc. Natl. Acad. Sci. USA* 84:4190–4194 (1987); Tanzi, R. E., et al., *Science* 235:880–884 (1987)). APP is a family of alternatively-spliced proteins, of unknown function, that are ubiquitously expressed (Tanzi, R. E., et al., *Nature* 331:528–530 (1988)). Unknown proteases cleave APP to produce a mixture of A$\beta$ peptides with carboxyl-terminal heterogeneity. A$\beta$1–40, the major soluble A$\beta$ species, is found in the CSF at low nanomolar concentrations (Vigo-Pelfrey, C., et al., *J. Neurochem.* 61:1965–1968 (1993)). A$\beta$1-42 is a minor soluble A$\beta$ species, but is heavily enriched in amyloid plaques (Masters, C. L., et al., *Proc. Natl. Acad. Sci. USA* 82:4245–4249 (1985); Kang, J., et al., *Nature* 325:733–736 (1987); Roher, A. F., et al., *J. Biol. Chem.* 268:3072–3083 (1993)).

The mechanism by which these amyloid deposits result in dementia is unclear, but may be related to the neurotoxic effects of A$\beta$ at micromolar concentrations (Pike, C. J., et al., *Brain Res.* 563:311–314 (1991)). Insight into the mechanism of amyloid deposit formation began with the discovery of pathogenic mutations of APP close to, or within, the AB domain (van Broeckhoven, C., et al., *Science* 248:1120–1122 (1990); Levy, E., et al., *Science* 248:1124–1126 (1990); Goate, A., et al., *Nature* 349:704–706 (1991); Murrell, J., et al., *Science* 254:97–99 (1991); Mullan, M., et al., *Nat. Genet.* 1:345–347 (1992)). These studies indicated that the metabolism of A$\beta$, and APP, is intimately involved with the pathophysiology of AD. Increasing evidence suggests that increased levels of A$\beta$1-42 accelerates amyloid deposition in early-onset familial AD (FAD). The FAD-linked APP670/671 mutation has been shown to increase the secretion of A$\beta$ species several-fold (Citron, M., et al, *Nature* 360:672–674 (1992)). While the APP717 mutation does not affect the quantity of A$\beta$ production (Cai, X-D., et al., *Science* 259:514–516 (1993)), this mutation increases the proportion of A$\beta$1-42 produced (Suzuki, N., et al., *Science* 264:1336–1340 (1994)).

Increased soluble A$\beta$1-42 has also been found in the brains of individuals affected by Down syndrome, a condition complicated by premature AD (Teller, J. K., et al., *Nat. Med.* 2:93–95 (1996)). Inheritance of the other FAD-linked mutations of Presenilin-1 (PSEN1) or Presenilin-2 (PSEN2) (Sherrington, R., et al. *Nature* 375:754–760 (1995); Levy-Lahad, E., et al., *Science* 269:973–977 (1995)) correlates with increased cortical amyloid burden. The emerging consensus is that the common effect of FAD-linked presenilin mutations is to increase A$\beta$1-42 production (Citron, M., et al., *Nat. Med.* 3:67–72 (1997); Xia, W., et al., *J. Biol. Chem.* 272:7977–7982 (1997)). Taken together these studies suggest that mutations in the genes linked to FAD (APP, PSEN1, PSEN2) can result in increased A$\beta$1-42 production and that this increase could cause FAD. In the vast majority of AD patients, however, overproduction does not occur (Van Gool, W. A., et al., *Ann. Neurol.* 37:277–279 (1995)).

Ninety percent of AD patients suffer from late-onset AD (LOAD). Three genes have been linked to this form of AD:APOE, LRP, and A2M. Inheritance of the APOE-$\epsilon$4 allele on chromosome 19 correlates with increased cortical amyloid burden (Rebeck, G. W., et al., *Neuron.* 11:575–580 (1993)). APOE promoter polymorphisms, which upregulate transcription of APOE, have recently been shown to be associated with AD (Bullido, M. J., et al., *Nat. Genet.* 18:69–71 (1998); Lambert, J. C., et al., *Human Mol. Gen.* 6:533–540 (1998)). Higher expression of the APOE-$\epsilon$4 allele, relative to APOE-$\epsilon$3, has been found in brains of APOE-$\epsilon$4 positive AD patients, but not in age- and genotype-matched controls (Lambert, J. C., et al., *Human Mol. Gen.* 6:2151–2154 (1997)). The absence of apoE in transgenic mice expressing FAD mutant APP attenuates A$\beta$ deposition (Bales, K. R., et al., *Nature Genetics* 17:264 (1997)). The second gene linked to LOAD, the LRP gene, encodes the low density lipoprotein receptor-related protein. APP, apoE, and $\alpha_2M$ are all ligands for this cell-surface receptor (Blacker, D. and Tanzi, R. E., *Archives of Neurology* 55:294–296 (1998); Kang, D. E., et al., *Neurology* 49:56–61 (1997); Blacker, D., et al., *Neurology* 48:139–147 (1997); Farrer, L. A., et al., *JAMA* 278:1349–1356 (1997); Strittmatter, W. J., et al., *Proc. Natl. Acad. Sci. USA* 90:1977–1981 (1993)). LRP internalizes ligands via endocytosis, and targets them for lysosomal degradation (Borth, W., *FASEB J.* 6:3345–3353 (1992)). Inheritance of a pentanucleotide deletion in the third gene associated with LOAD, A2M (i.e, inheritance of A2M-2), confers increased risk for AD and is present in ~30% of the population (Blacker, D., et al., *Nat. Genet.* 19:357–360 (1998)). The protein product of A2M, $\alpha_2M$, is an abundant pan-protease inhibitor found primarily in serum, but is also present in brain and other organs (for example, liver). $\alpha_2M$ binds A$\beta$ and can mediate its internalization and degradation (Borth, W., *FASEB J.* 6:3345–3353 (1992); Narita, M., et al., *J. Neurochem.* 69:1904–1911 (1997)).

$\alpha_2M$ has been implicated in the pathogenesis of AD by both biological and genetic findings. $\alpha_2M$-like immunoreactivity was observed in AD cortical senile plaques (Bauer, J., et al., *FEBS Lett.* 285:111–114 (1991)) and it was shown that $\alpha_2M$ is upregulated in the AD brain where it localizes to neuritic but not diffuse amyloid plaques (Strauss, S., et al., *Lab. Invest* 66:223–230 (1992); Van Gool, D., et al., *Neurobiol. Aging* 14:233–237(1993)). In addition, A$\beta$ was found to bind to $\alpha_2M$ with high affinity (Du, Y., et al., *J. Neurochem.* 69:299–305 (1997)), and binding prevented amyloid fibril formation as well as neurotoxicity associated with aggregated A$\beta$ (Du, Y., et al., *J. Neurochem.* 70:1182–1188 (1998); Hughes, S. R., et al., *Proc. Natl. Acad Sci. USA*

95:3275–3280 (1998)). Activated $\alpha_2$M-A$\beta$ complexes were recently shown to be internalized and targeted for degradation by glioblastoma cells via binding to LRP (Narita, M., et al., *J. Neurochem.* 69:1904–1911 (1997)). Moreover, LRP is especially abundant in brain regions affected by AD such as the hippocampus (Rebeck, G. W., et al., *Neuron* 11:575–580 (1993); Tooyama, I., et al., *Mol. Chem. Neuropathol.* 18:153–160 (1993)), and serves as a receptor for ApoE (Rebeck, G. W., et al., *Neuron* 11:575–580 (1993)), a well established genetic risk factor (Blacker, D., et al., *Nature Gen.* 19:357–360 (1998)).

The genetic linkage of APP, APOE, A2M, and their receptor LRP to AD suggests that these proteins may participate in a common neuropathogenic pathway leading to AD (Blacker, D., et al., *Nat. Genet.* 19:357–360 (1998)). This pathway may be the $\alpha_2$M mediated clearance and degradation of A$\beta$ through $\alpha_2$M binding to LRP for endocytosis and lysosomal degradation, and by serving as a direct mediator for A$\beta$ degradation when $\alpha_2$M is complexed with an unidentified serine protease (Qiu, W. Q., et al., *J. Biol. Chem.* 271:8443–8451 (1996)). This hypothesis is supported, inter alia, by the fact that apoE and $\alpha_2$M are both ligands for LRP and, in addition, that apoE has previously been reported to inhibit $\alpha_2$M mediated degradation of A$\beta$ (Rebeck, G. W., et al., *Ann. Neurol.* 37:211–217 (1995); Zhang, Z., et al., *Int. J. Exp. Clin. Invest.* 3:156–161 (1996)).

However, in its normal role, $\alpha_2$M also binds a host of cytokines, growth factors, and biologically active peptides (Borth, W., *FASEB J.* 6:3345–3353 (1992)). It has also recently been shown to activate the phosphatidylinositol 3-kinase suggesting a role in signaling (Misra, U. K. and Pizzo, S. V., *J. Biol. Chem.* 273:13399–13402 (1998)). Thus, defective activity of $\alpha_2$M may lead to AD-related neurodegeneration by a variety of mechanisms beyond possible effects on A$\beta$ accumulation and deposition.

A reduced steady-state level of secreted $\alpha_2$M or the presence of defective tetramers due to dominant negative effects of A2M-2 could result in impaired $\alpha_2$M function. Partial or total deletion of the sequences coding for the bait region in exons 17 and 18 are likely to modify protease binding, activation, and internalization of potentially defective tetramers containing mutant monomer(s). Therefore, the generation of very low levels of mutant monomers may have an amplified effect as one mutant monomer may potentially inhibit the function of three wild-type monomers in the tetramer (dominant negative effect). Thus a critical role for $\alpha_2$M is indicated in AD neuropathogenesis. The data described in Example 1 show that the A2M-2 deletion leads to deleted/truncated forms of $\alpha_2$M RNA and protein that may have a dominant negative effect on normal $\alpha_2$M. Based on the finding, described herein, that the A2M-2 deletion leads to the production of altered $\alpha_2$M transcripts and proteins, strategies aimed at replacing or supplementing normal $\alpha_2$M function and activities, and/or at suppressing defective $\alpha_2$M function in the brain may effectively serve as a means for therapeutically preventing, treating, or even reversing AD neuropathogenesis. In addition, these strategies may be useful for treating other pathologies associated with defective $\alpha_2$M function. Moreover, methods based on the results and experiments described herein may be used to screen for these therapeutic agents.

The first aspect of present invention relates to therapeutic agents for AD that can replace or supplement normal $\alpha_2$M function, and/or suppress expression of A2M-2.

In one embodiment of the invention, the therapeutic agent is an anti-LRP-A$\beta$ molecule, which is a molecule containing LRP and A$\beta$ binding domains. This molecule may be a peptide, or other molecule, that is capable of binding to both A$\beta$ and LRP. This anti-LRP-A$\beta$ molecule may also contain other domains. An anti-LRP-A$\beta$ molecule having A$\beta$ and LRP binding domains could bind A$\beta$ and target it for LRP mediated endocytosis followed by lysosomal degradation, and thus would be useful, inter alia, as a therapeutic agent.

In one embodiment of the invention, the anti-LRP-A$\beta$ molecule is a peptide, referred to herein as the anti-LRP-A$\beta$ peptide. A 250-residue fragment of the $\alpha_2$M monomer contains both the A$\beta$ and LRP binding domains (Hughes, S. R., et al., *Proc. Natl. Acad. Sci. U.S.A.* 95:3275–3280 (1998)). Thus, in one embodiment of the invention, the anti-LRP-A$\beta$ peptide would be composed of the entire A$\beta$ and LRP binding domains of $\alpha_2$M (SEQ ID NO:4). Alternatively, the A$\beta$ and LRP binding domains may be composed of portions of the A$\beta$ and LRP binding domains of $\alpha_2$M. The A$\beta$ binding domain of $\alpha_2$M is located between residues 1201 and 1313, approximately 600 residues C-terminal to the bait region (Hughes, S. R., et al., *Proc. Natl. Acad. Sci. USA* 95:3275–3280 (1998)). Thus, in another embodiment of the invention, the A$\beta$ binding domain of the anti-LRP-A$\beta$ peptide would consist of the full A$\beta$ binding domain of $\alpha_2$M (between residues 1201–1313, SEQ ID NO:6), but only a portion of the LRP binding domain. In another embodiment of the invention, the A$\beta$ binding domain would consist of at least 50 contiguous residues of the full A$\beta$ binding domain of $\alpha_2$M. In another embodiment of the invention, the A$\beta$ binding domain would consist of 10–50 contiguous residues of the full A$\beta$ binding domain of $\alpha_2$M.

In addition, peptides that can bind A$\beta$ in vivo and inhibit A$\beta$ fibril formation have been described by Soto et al. (Soto, C. et al., *Nat. Med.* 4:822–826 (1998); Soto, C., et al., *Biochem. Biophys. Res. Comm.* 226:672–680 (1996)). These peptides (SEQ ID NOs:12, 16, 18, 20, 22, 24 and 26) have homology to A$\beta$ and a similar degree of hydrophobicity, but have a low propensity to adopt a $\beta$-sheet conformation. In particular one 11 residue A$\beta$ binding peptide, having the amino acid sequence of SEQ ID NO:12, and encoded by the nucleic acid sequence of SEQ ID NO:11, was particularly effective. Therefore, in a preferred embodiment of the invention, the A$\beta$ domain of the anti-LRP-A$\beta$ peptide would have the sequence of this 11-residue peptide. Thus, in a preferred embodiment of the invention, the A$\beta$ domain of the anti-LRP-A$\beta$ peptide has the amino acid sequence of SEQ ID NO:12, and is encoded by the nucleic acid sequence of SEQ ID NO:11. Two shorter derivatives of this 11 residue A$\beta$ binding peptide, composed of a 5 residue peptide (SEQ ID NO:22) and a 7 residue peptide (SEQ ID NO:18) also effectively bound A$\beta$ and inhibited fibril formation (Soto, C. et al., *Nat. Med.* 4:822–826 (1998); Soto, C., et al., *Biochem. Biophys. Res. Comm.* 226:672–680 (1996)). Thus, in another preferred embodiment of the invention, the A$\beta$ binding domain has the amino acid sequence of SEQ ID NO:22, and is encoded by the nucleic acid sequence of SEQ ID NO:21, or has the amino acid sequence of SEQ ID NO:18, and is encoded by the nucleic acid sequence of SEQ ID NO:17. Alternatively, the A$\beta$ binding domain may be composed of other derivatives of the 11 residue A$\beta$ binding peptide having 3, 4 or 6 residues (SEQ ID NO:24, 22 and 18 respectively). Thus in another embodiment of the invention, the A$\beta$ binding domain has the amino acid sequence of SEQ ID NO:24, 22 or 18, and is encoded by the nucleic acid sequence of SEQ ID NO:23, 21 or 17, respectively.

The LRP binding domain of $\alpha_2$M is located between residues 1312 and 1451 of $\alpha_2$M, directly C-terminal to the A$\beta$ binding domain (Hughes, S. R., et al., *Proc. Natl. Acad.*

Sci. USA 95:3275–3280 (1998)). Thus, in one embodiment of the invention, the LRP binding domain of the anti-LRP-Aβ peptide is composed of the full LRP binding domain of $\alpha_2$M (residues 1313–1451, SEQ ID NO:8). In another embodiment of the invention, the LRP binding domain is composed of at least at least 50 contiguous residues of the full LRP binding domain of $\alpha_2$M. In yet another embodiment of the invention, the LRP binding domain is composed of 10–50 contiguous residues of the full LRP binding domain of $\alpha_2$M. Within the LRP binding domain, a 27 residue LRP binding consensus sequence exists at residues 1366–1392 (Nielsen, K. L., et al., *J. Biol. Chem.* 271:12909–12912 (1996)). Thus, in a preferred embodiment of the invention, the LRP binding domain of the anti-LRP-Aβ peptide is composed of residues 1366–1392 (SEQ ID NO:10) of $\alpha_2$M. Alternatively, the LRP binding domain may be composed of a contiguous portion of residues 1313–1451 of $\alpha_2$M that includes residues 1366–1392. In another preferred embodiment, the anti-LRP-Aβ peptide is composed of the 11 residue Aβ binding domain and the 27 residue consensus sequence of the $\alpha_2$M LRP binding domain (SEQ ID NO:14).

The Aβ binding domain and the LRP binding domain of the anti-LRP-Aβ molecule may be connected to each other directly by a covalent bond, or indirectly by another molecule, such as a linker, or linkerless polyethylene glycol. Linker molecules include polymers such as polyethylene glycol (PEG) and peptides or amino acid residues. In addition, linkerless PEG modification (PEGylation) may be used (Francis, G. E., et al., *Int. J. Hematol.* 68:1–18 (1998)). Various methods of connecting molecules using linkers and other molecules are well known in the art, and may be used to connect the Aβ and LRP binding domains (See, for example, Francis, G. E., et al., *Int. J. Hematol.* 68:1–18 (1998); Raag, R. and Whitlow, M., *FASEB J.* 9:73–80 (1995); Deguchi, Y., et al., *Bioconjug. Chem.* 10:32–37 (1999); Luo, D., et al., *J. Biotechnol.* 65:225–228 (1998); Reiter, Y., and Pastan, I., *Clin Cancer Res.* 2:245–52 (1996); DeNardo, G. L., et al., *Clin. Canc. Res.* 4:2483–90 (1998); Taremi, S. S., *Protein Sci.* 7:2143–2149 (1998); Schaffer, D. V., and Lauffenburger, D. A., *J. Biol. Chem.* 273:28004–28009 (1998); Skordalakes, E., et al., *Biochem.* 37:14420–14427 (1998); Czerwinski, G. et al., *Proc. Natl. Acad. Sci. U.S.A.* 95:11520–11525 (1998); Daffix, I., et al., *J. Pept. Res.* 52:1–14 (1998); Liu, S. J., et al., *Blood* 92:2103–2112 (1998); Chandler, L. A., et al., *Int. J. Cancer* 78:106–111 (1998); Park, C. J., *Appl. Microbiol. Biotechnol.* 50:71–76 (1998); Suzuki, Y., et al., *J. Biomed. Mater. Res.* 42:112–116 (1998); Filikov, A. V., and James, T. L., *J. Comput. Aided Mol. Des.* 12:229–240 (1998); MacKenzie, R., and To, R., *J. Immunol. Methods* 220:39–49 (1998)).

In one preferred embodiment of the invention, the linker is composed of amino acid residues, for example, glycine residues or proline residues. Where the linker is composed of amino acid residues, it may be from 1–20 residues, but will preferably be 5–10 residues, and more preferably will be 5 residues.

Where the anti-LRP-Aβ molecule is a peptide, within the peptide, the Aβ binding domain may be C-terminal, or N-terminal to the LRP binding domain. However, preferably, the Aβ binding domain will be N-terminal to the LRP binding domain, which is the order of the Aβ and LRP binding domains in naturally occurring $\alpha_2$M.

In addition, the invention provides for nucleic acid molecules that encode an anti-LRP-Aβ peptide. Thus, in another embodiment of the invention, the nucleic acid molecules would encode an anti-LRP-Aβ peptide having the sequences described above. The invention also relates to nucleic acids having at least 95% homology to these nucleic acids. In addition, the invention relates to nucleic acids that hybridize to a nucleic acid that is complementary to a nucleic acid encoding the anti-LRP-Aβ peptide. The conditions under which the first and second polynucleotides hybridize are preferably as follows: (a) incubate overnight at 42° C. in a solution consisting of 50% formamide, 5×SSC, 50 mM sodium phosphate (pH 7.6), 5×Denhardt's solution, 10% dextran sulfate, and a 20 µg/ml denatured, sheared salmon sperm DNA; and (b) wash at 65° C. in a solution consisting of 0.1×SSC.

The anti-LRP-Aβ peptide may be produced using standard solid phase synthesis methods for protein synthesis, and purified by high performance liquid chromatography (HPLC) which are well known in the art (See "Preparation and Handling of Peptides," in: *Current Protocols in Protein Science*, Coligan, J. E., et al., eds., John Wiley and Sons, Inc., pub., Vol. 2., Chapter 18 (Suppl. 14 1998)). Alternatively, the anti-LRP-Aβ peptide may be produced using standard recombinant DNA methods. For example, The DNA coding for the desired sequence of the LRP binding domain (for example, the 27 residue consensus sequence) may be obtained by PCR amplification of the codons encoding the desired LRP binding domain using primers designed to flank the desired codons. This DNA may then be used as a template for PCR mediated integration of the sequence coding for the desired Aβ binding domain. For PCR mediated insertion of the Aβ domain, a nucleotide 5' PCR primer can be designed having (1) a region homologous to the end of the DNA sequence encoding the desired LRP binding domain that was amplified as described immediately above, and (2) immediately 5' to this region, a region encoding the desired Aβ binding domain, and (3) immediately 5' to this region a start codon. For the 3' primer, the 3' flanking primer used to amplify the LRP binding domain, which sequence is now being used as the template, may be used. Alternatively, to produce an anti-LRP-Aβ peptide having the entire Aβ and LRP binding domains of $\alpha_2$M (residues 1202–1451), primers may be designed to flank the coding sequence for these domains, to amplify this region (nucleotides 3713–4465). A start codon may be then added by PCR mediated insertion. To amplify a coding region that encodes less than the entire AB and LRP binding domains, the primers may instead be designed to flank this smaller region of $\alpha_2$M. The resulting nucleic acid molecule is DNA encoding a fusion protein having LRP and Aβ binding domains, and a start codon, such that this molecule may be inserted into an expression vector to produce the anti-LRP-Aβ peptide.

Once DNA encoding the desired fusion protein is obtained, PCR mediated insertion may be used to insert restriction enzyme sites at the 5' and 3' ends of the fusion gene so that the fusion protein gene may then be cleaved with these restriction enzymes for insertion into an expression vector, and a vector for use in the yeast three hybrid system (Tirode, F., et al., *J. Biol. Chem.* 272:22995–22999 (1997)). For example, an Xho I and Kpn I restriction sites can be inserted at the 5' and 3' ends of the fusion protein gene, respectively. Cleavage with these restriction enzymes will then facilitate cloning of the fusion protein gene into (i) the pBAD/His expression vector (Invitrogen), for arabinose dependent expression of anti-LRP-Aβ in *E. coli*, and (ii) the pLex9-3H vector for use in the yeast three hybrid system (Tirode, F., et al., *J. Biol. Chem.* 272:22995–22999 (1997)). The protein product, named anti-LRP-Aβ peptide, of the resulting gene should have both Aβ and LRP binding properties.

The ability of anti-LRP-Aβ molecule to bind Aβ and LRP and to undergo LRP mediated endocytosis and degradation may be tested using gel-filtration chromatography, immunoblotting and cell culture techniques. If the anti-LRP-Aβ molecule is a peptide, a yeast-three-hybrid system may also be used to evaluate the anti-LRP-Aβ peptide (Tirode, F., et al., *J. Biol. Chem.* 272:22995–22999 (1997)). If necessary, the binding properties of an anti-LRP-Aβ peptide may be reoptimized using in vivo evolution techniques (Buchholz, F., et al., *Nat. Biotechnol.* 16:657–662 (1998)).

Gel-filtration chromatograpy can be performed as described by Narita et al. (Narita, M., et al., *J. Neurochem.* 69:1904–1911 (1997)) to test the ability of an anti-LRP-Aβ molecule to bind Aβ. The anti-LRP-Aβ molecule is incubated with Aβ1-42 that is radiolabeled with $^3$H, $^{14}$C or $^{125}$I. In the following discussion, $^{125}$I-Aβ is used as an example of radiolabeled Aβ. Methylamine or trypsin activated $\alpha_2$M, and $\alpha_2$M, and unactivated $\alpha_2$M and $\alpha_2$M-2, may be used as controls. anti-LRP-Aβ/$^{125}$I-Aβ, $\alpha_2$M/$^{125}$I-Aβ and $\alpha_2$M-2/$^{125}$I-Aβ complexes are then separated from unbound $^{125}$I-Aβ using a Superose 6 gel-filtration column (0.7×20 cm) under the control of an FPLC (Pharmacia) that has been standardized with molecular weight markers from 1000 kD–4 kD. If anti-LRP-Aβ has bound $^{125}$I-Aβ, $^{125}$I-Aβ should be detected by gamma counter at two peaks, one corresponding to the molecular weight of the anti-LRP-Aβ/$^{125}$I-Aβ complex (about 8–9 kD for a complex containing an anti-LRP-Aβ of about 40 residues), and one corresponding to the molecular weight of $^{125}$I-Aβ (4.5 kD).

Alternatively, or in addition to gel-filtration chromatography, immunoblotting methods (Narita, M., et al., *J. Neurochem.* 69:1904–1911(1997)) may be used to determine whether an anti-LRP-Aβ molecule can bind Aβ. Unlabeled Aβ is incubated separately with anti-LRP-Aβ, unactivated $\alpha_2$M, unactivated $\alpha_2$M-2, $\alpha_2$M activated by methylamine or trypsin, or $\alpha_2$M-2 activated by methylamine or trypsin. Samples are then electrophoresed on a 5% SDS-PAGE, under non-reducing conditions, transferred to polyvinyl difluoride nitrocellulose membrane, and probed with anti-Aβ IgG, or an antibody specific for the anti-LRP-Aβ molecule. Where one or more domains of the anti-LRP-Aβ molecule are derived from $\alpha_2$M, an anti-$\alpha_2$M IgG that recognizes the domain derived from $\alpha_2$M may be used, such as anti-$\alpha_2$M IgG raised against the LRP binding domain of $\alpha_2$M (for example, Marynen, P., et al., *J. Immunol.* 127:1782–1787 (1981)). If the anti-LRP-Aβ/Aβ sample may be detected by both the antibody against anti-LRP-Aβ, and anti-Aβ IgG it can be concluded that the anti-LRP-Aβ molecule can bind Aβ. Where the Aβ binding domain of the anti-LRP-Aβ molecule is derived from Aβ, the anti-Aβ antibody should be tested to ensure that it does not recognize the anti-LRP-Aβ molecule. Several antibodies against Aβ are available, including 6310, WO2, 4G8, G210 and G211. Antibody 4G8 may recognize an anti-LRP-Aβ molecule for which Aβ binding domain is derived from Aβ. In addition, some anti-$\alpha_2$M antibodies may not recognize an anti-LRP-Aβ molecule derived from $\alpha_2$M, therefore, they should be tested for the ability to recognize the peptide prior to performing the immunoblotting, endocytosis, and degradation protocols described herein. Marynen et al., (Marynen, P., et al., *J. Immunol.* 127:1782–1787 (1981)) describe an anti-$\alpha_2$M antibody raised against the LRP binding domain that may be able to recognize an anti-LRP-Aβ peptide having an LRP binding domain derived from $\alpha_2$M. Other anti-$\alpha_2$M antibodies are available from Sigma and Cortex Biochem (San Leandro, Calif., U.S.A.). $\alpha_2$M can be obtained from Sigma, or purified from human plasma and activated as described in Warshawsky, I., et al., *J. Clin. Invest.* 92:937–944 (1993). Synthetic Aβ$_{1-42}$ can be purchased from Bachem (Torrance, Calif., U.S.A.).

Gel-filtration chromatography and immunoblotting as described above may also be used to determine the ability of anti-LRP-Aβ to bind LRP, by using labeled soluble LRP (for example, the extracellular region of LRP) in place of labeled Aβ for gel-filtration chromatography experiments, and anti-LRP IgG in place of anti-Aβ IgG for immunoblotting experiments. Alternatively, for the immunoblotting protocol, the anti-LRP-Aβ molecule may be labeled with fluorescent or radioactive label. For a labeled anti-LRP-Aβ molecule, it can be concluded that the anti-LRP-Aβ molecule can bind Aβ if the labeled band corresponds to a band recognized by anti-Aβ antibody.

The ability of Aβ/anti-LRP-Aβ complexes to undergo LRP mediated endocytosis and subsequent degradation can be determined using cell culture experiments using cells that express LRP as described by Kounnas et al. (Kounnas, M. Z., et al., *Cell* 82:331–340 (1995); Kounnas, M. Z., et al., *J. Biol. Chem.* 270:9307–9312 (1995)). The amount of radio-ligand that is internalized or degraded by cells has been described previously (Kounnas, M. Z., et al., *Cell* 82:331–340 (1995); Kounnas, M. Z., et al., *J. Biol. Chem.* 270:9307–9312 (1995)). Cells that express LRP include, but are not limited to, adipocytes, astrocytes, fibroblasts, hepatocytes, macrophages, monocytes, and syncytiotrophoblasts. In one preferred embodiment of the invention, mouse embryo fibroblasts are used for the cell culture experiment.

Cells expressing LRP are incubated for 18 hours with $^{125}$I-Aβ (alternatively, Aβ may be labeled with $^3$H or $^{14}$C) in the presence or absence of anti-LRP-Aβ, unactivated $\alpha_2$M, unactivated $\alpha_2$M-2, $\alpha_2$M activated by methylamine or trypsin, or $\alpha_2$M-2 activated by methylamine or trypsin; in the presence or absence of RAP (400 nM). RAP is an inhibitor of LRP ligand binding, and is added to determine if endocytosis is LRP mediated. RAP can be isolated and purified from a glutathione S-transferase fusion protein expressed in *E. coli* as described in Warshawsky, I., et al., *J. Clin. Invest.* 92:937–944 (1993b). To assess endocytosis rather than degradation, chloroquine (0.1 mM) is added at the same time as anti-LRP-Aβ/$^{125}$I-Aβ to inhibit lysosomal degradation of $^{125}$I-Aβ.

The amount of radioactive ligand released by treatment with trypsin-EDTA, proteinase K solution defines the surface-bound material, and the amount of radioactivity associated with the cell pellet defines the amount or internalized ligand. Activated $\alpha_2$M/$^{125}$I-Aβ will serve as positive control. Under the conditions described, more than 8 fmoles/$10^4$ cells of activated $\alpha_2$M/$^{125}$I-Aβ should be internalized after 18 hours of incubation (Kounnas, M. Z., et al., *Cell* 82:331–340 (1995)). Unactivated $\alpha_2$M/$^{125}$I-Aβ will serve as the negative control for endocytosis, because $\alpha_2$M must be activated by trypsin or methylamine to be recognized by LRP. If the amount of anti-LRP-Aβ/$^{125}$I-Aβ is greater than 4–8 fmoles/$10^4$ cells, it can be concluded that anti-LRP-Aβ/$^{125}$I-Aβ has the ability to undergo LRP mediated endocytosis. Unactivated $\alpha_2$M/$^{125}$I-Aβ, and activated $\alpha_2$M/$^{125}$I-Aβ in the presence of RAP should not be internalized, therefore no more than 2–4 fmoles/$10^4$ cells should be internalized (Kounnas, M. Z., et al., *Cell* 82:331–340(1995)). Internalization of the anti-LRP-Aβ/$^{125}$I-Aβ complex will be deemed abolished if anti-LRP-Aβ/$^{125}$I-Aβ, in the presence and absence of RAP, and unactivated $\alpha_2$M/$^{125}$I-Aβ show the same amount of radioactivity associated with the cell pellet.

To determine the ability of Aβ/anti-LRP-Aβ complexes to undergo degradation after endocytosis, this cell culture protocol is repeated without chloroquine. The radioactivity appearing in the cell culture medium that is soluble in 10% trichloroacetic acid is taken to represent degraded $^{125}$I-Aβ (Kounnas, M. Z., et al., *Cell* 82:331–340 (1995); Narita, M., et al., *J. Neurochem.* 69:1904–1911 (1997)). Total ligand degradation is corrected for the amount of degradation that occurs in control wells lacking cells. Because free $^{125}$I-Aβ can be degraded in an LRP independent manner, degradation is measured for anti-LRP-Aβ and α$_2$M complexes with $^{125}$I-Aβ, as well as for free $^{125}$I-Aβ, in the presence and absence of RAP. Using the same positive and negative controls as above, if RAP does not decrease the amount of TCA soluble radioactivity by at least 30% for the anti-LRP-Aβ/$^{125}$I-Aβ complex, it can be concluded that $^{125}$I-Aβ ligand of anti-LRP-Aβ is not degraded.

Figure 7:
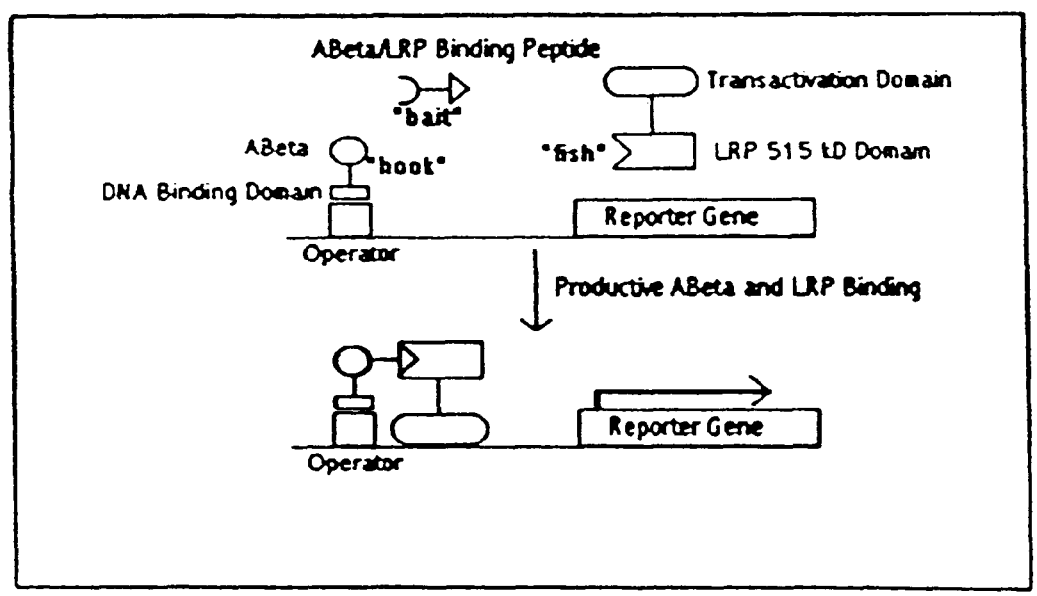
FIG. 7.

Another method of testing the ability of anti-LRP-Aβ molecule to bind Aβ and LRP is the yeast three-hybrid system described by Tirode et al. (Tirode, F., et al., *J. Biol. Chem.* 272:22995–22999(1997)). This method may be used where the anti-LRP-Aβ molecule is a peptide. In this system, yeast growth only occurs when the "bait" recognizes both the "hook" and the "fish" (FIG. 7). In this instance, the "hook" is constructed of the DNA coding for Aβ (Bales, K. R., et al., *Nat. Genet.* 17:264 (1997)), fused to the coding sequence of the LexA DNA binding protein in pLex9-3H, a TRP1 episomal vector (Tirode, F., et al., *J. Biol. Chem.* 272:22995–22999 (1997)). The "fish" is constructed of the coding sequence for the 515 kD extracellular domain of LRP, fused to the B42 activation domain in pVP 16, a LEU2 episomal vector (Tirode, F., et al., *J. Biol. Chem.* 272:22995–22999 (1997)). The "bait" is the DNA coding for anti-LRP-Aβ in the pLex9-3H vector, expression of anti-LRP-Aβ is repressed by methionine. After transformation of yeast with these vectors, transcription of the Leu 2 reporter gene will occur only when the Aβ fused DNA binding domain is brought into proximity to the transcriptional activation domain fused to LRP. The Aβ/LRP binding fusion peptide should promote reporter gene transcription. The interaction between anti-LRP-Aβ and Aβ and LRP (515 kD) will be considered positive only if reporter gene expression (yeast growth) occurs when Aβ-LexA, LRP(515 kD)-B42, and anti-LRP-Aβ are expressed.

The anti-LRP-Aβ molecule of the invention may be administered per se, or in the form of a pharmaceutically acceptable salt with any non-toxic, organic or inorganic acid. Illustrative inorganic acids which form suitable salts include hydrochloric, hydrobromic, sulfuric and phosphoric acid, and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

The amount of the anti-LRP-Aβ molecule administered to a subject will vary depending upon the age, weight, and condition of the subject. The course of treatment may last from several days to several months or until a cure is effected or a diminution of disease state is achieved, or alternatively may continue for a period of years, for example, when used prophylactically. Optimal dosing schedules can be calculated from measurements of drug accumulation in the body. Persons of ordinary skill can easily determine optimum dosages, dosing methodologies and repetition rates. However, the amount of anti-LRP-Aβ molecule administered to a subject is generally from 0.1 nanograms to 10 mg/kg/day, and is typically an amount ranging from 1 nanogram to 1 mg/kg/day.

The present invention also relates to antisense oligonucleotides targeted to A2M-2 RNA, and to their use as therapeutic agents for AD and for suppressing A2M-2 expression. Partial or total deletion of the sequences coding for the bait region in exons 17 and 18 of α$_2$M is likely to modify protease binding, interfering with α$_2$M activation. Incorporation of one or more mutant monomers into tetramers might thereby result in defective tetramers that could not be activated efficiently and, therefore, could not undergo subsequent endocytosis via LRP. Thus, the generation of very low levels of mutant monomers may have an amplified effect as one mutant monomer may potentially inhibit the function of three wild-type monomers in the tetramer (dominant negative effect). One way to counter this dominant negative effect is to decrease the level of abnormal α$_2$M by interfering with gene expression at the RNA level. For this purpose, an antisense oligonucleotide specific for A2M-2 RNA can be used. This oligonucleotide will be referred to herein as A2M-2 antisense oligonucleotide. The A2M-2 antisense oligonucleotide may be targeted to any A2M-2 RNA molecule, but in a preferred embodiment of the invention, it is targeted to heterologous nuclear (hnRNA).

The A2M-2 deletion is found in the splicing region of exon 18, therefore, in one embodiment of the invention, the A2M-2 antisense oligonucleotide is designed to target A2M-2 RNA transcripts before splicing occurs, referred to as hnRNA. In addition, in order to be specific for A2M-2 hnRNA the A2M-2 antisense oligonucleotide is designed to target the pentanucleotide deletion found in A2M-2. In another embodiment of the invention, the A2M-2 antisense oligonucleotide is designed to target A2M-2 mRNA. The A2M-2 deletion results in several variant mRNA transcripts with varying sequences. The A2M-2 antisense oligonucleotides of the invention can be designed to target individual variants, or to target more than one of these variants. In addition, A2M-2 antisense oligonucleotides targeting different A2M-2 mRNA variants, or targeting A2M-2 hnRNA, may be used either alone, or in conjunction with one another.

In addition, the A2M-2 antisense oligonucleotide must be long enough so that it targets only A2M-2, but short enough to optimize delivery. Thus, the antisense oligonucleotide of the invention is preferably 8–50 nucleotides in length, and more preferably 15–30 nucleotides in length. Therefore, in one embodiment of the invention, the A2M-2 antisense oligonucleotide is 8–50 nucleotides and is complementary to the coding strand of the region of A2M-2 containing the site of the pentanucleotide deletion. In a preferred embodiment of the invention, the A2M-2 antisense oligonucleotide is composed of 15–30 contiguous nucleotides of a region complementary to the site on the coding strand of A2M-2 that contains the pentanucleotide deletion. In another embodiment of the invention, the A2M-2 antisense oligonucleotide is composed of the last 8–50 contiguous nucleotides of SEQ ID NO:27. In a preferred embodiment of the invention, the A2M-2 antisense oligonucleotide is composed of the last 15–30 contiguous nucleotides of SEQ ID NO:27. In yet another preferred embodiment, the A2M-2 antisense oligonucleotide is composed of nucleotides 36–50 of SEQ ID NO:27. In another preferred embodiment of the invention, the A2M-2 antisense oligonucleotide is composed of nucleotides 20–50 of SEQ ID NO:27.

The A2M-2 antisense oligonucleotide may be DNA or RNA, i.e., it may be composed of deoxyribonucleic acids or ribonucleic acids, respectively. Alternatively, the oligonucleotide may be composed of nucleotides with a phosphorothioate backbone to render the oligonucleotide more resistant to enzymatic degradation (van der Krol, A. R., et al., *Biotechniques* 6:958–976 (1988); Cazenave, C. & & Hélène, C., "Antisense Oligonucleotides," in: *Antisense nucleic acids and proteins: Fundamental and applications,* Mol, J. N. M. & van der Krol, A. R., eds., M. Dekker, publ., New York, pp. 1–6 (1991); Milligan, J. F., et al., *J. Med. Chem.* 36:1923–1937 (1993)). In a preferred embodiment of the invention the A2M-2 antisense oligonucleotide is DNA.

Other modifications which may be used to protect the oligonucleotide include chemical changes to the 3' end of the oligonucleotide (van der Krol, A. R., et al., *Biotechniques* 6:958–976 (1988); Khan, I. M. & Coulson, J. M., *Nucleic Acids Res.* 21:2957–2958 (1993); Tang, J. Y., et al. *Nucleic Acids Re.* 21:2729–2735 (1993)) or biotynylation of the 3' end followed by conjugation with avidin (Boado, R. J. & Pardridge, W. M., *Bioconjugate Chem.* 3:519–523 (1992)). Alternatively, lipofection may be used to deliver the oligonucleotide, i.e., packaging the oligonucleotide in lipid (McCarthy, M. M., et al. *Endocrin.* 133:433–439 (1993b); Ogawa, S., et al., *J. Neurosci.* 14:1766–1774 (1994)). Lipofection protects the oligonucleotide from nucleases and may aid in delivery to the central nervous system.

The A2M-2 antisense oligonucleotide can be easily synthesized by means of commercially-available automatic DNA synthesizers such as a DNA synthesizer manufactured by Applied Biosystems, or MilliGen, etc. In addition, methods of synthesizing oligonucleotides are well known in the art and are described, for example, in *Oligonucleotides and Analogues a Practical Approach,* Eckstein, F., ed., Oxford University Press, publ. New York, (1991), and "Synthesis and Purification of Oligonucleotides" in: *Current Protocols in Molecular Biology,* Ausubel, F. M., et al., eds., John Wiley & Sons, Inc., publ., Vol. 1, §§2.11–2.12 (Suppl. 9 1993).

The invention also relates to pharmaceutical compositions containing the A2M-2 antisense oligonucleotide, and one or more pharmaceutically acceptable carriers. In addition, the invention provides a method of treating AD and/or of suppressing A2M-2 expression by administering the A2M-2 antisense oligonucleotide to a subject. Preferably, the A2M-2 antisense oligonucleotide is delivered to a subject who has been determined to be heterozygous or homozygous for the A2M-2 allele. Procedures for selecting and assessing subjects who are heterozygous or homozygous for A2M-2 are described in Tanzi et al., U.S. Ser. No. 09/148, 503, PCT Application No. PCT/US98/18535, and Blacker, D., et al., *Nat. Genet.* 19:357–360 (August 1998). In another preferred embodiment of the invention, treatment of a subject with the A2M-2 antisense oligonucleotide is done in conjunction with a therapy designed to replace or supplement $\alpha_2M$ function.

Antisense oligonucleotides have been safely administered to humans and several clinical trials are presently underway. Based on these clinical trials, oligonucleotides are understood to have toxicities within acceptable limits at dosages required for therapeutic efficacy. One such antisense oligonucleotide, identified as ISIS 2105, is presently in clinical trials, and is used as a therapeutic against papillomavirus. Another antisense oligonucleotide, ISIS 2922, has been shown to have clinical efficacy against cytomegalovirus-associated retinitis *Antiviral Agents Bulletin* 5: 161–163 (1992); *BioWorld Today,* Dec. 20, 1993. Therefore, it has been established that oligonucleotides are useful therapeutic agents and that they can be used for treatment of animals, especially humans.

The amount of the A2M-2 antisense oligonucleotide administered to a subject will vary depending upon the age, weight, and condition of the subject. The course of treatment may last from several days to several months or until a cure is effected or a diminution of disease state is achieved, or alternatively may continue for a period of years, for example, when used prophylactically. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be estimated based on $EC_{50}$'s in in vitro and in vivo animal studies. In general, dosage is from 0.01 mg to 100 g and may be given once daily, weekly, monthly or yearly.

Another therapeutic method of the invention is gene therapy to supplement $\alpha_2M$ function. Because the A2M-2 deletion may result in impaired $\alpha_2M$ function, a strategy aimed at supplementing normal $\alpha_2M$, such as gene therapy, could serve as a means for treating, preventing or reversing AD. One embodiment of the invention is a viral vector carrying a transgene encoding wild type $\alpha_2M$, or an anti-LRP-A$\beta$ peptide. Viral vectors suitable for use in the invention are those that are capable of transfecting nondividing, post-mitotic cells, and have low cytotoxicity. These vectors include, but are not limited to adenovirus, lentivirus, and HSV-1, but are preferably adeno-associated virus vector (AAV). AAV is a DNA virus that is not directly associated with any human disease, and therefore should present a lower risk of cytotoxicity (Freese, A. et al., *Epilesia* 38:759–766 (1997)). It can transfect nondividing, post-mitotic cells, such as neurons and dormant glial cells. In addition, there is some evidence that AAV may stably integrate into the host chromosome (Freese, Z. et al, *Mov. Disord.* 11:469–488 (1996); Kaplitt, M. G. et al., *Natur. Genet.* 8:148–154 (1994); Samulski, R. J., et al., *J. Virol* 63:3822–3888 (1989); Kotin, R. M. et al., *Proc. Natl. Acad. Sci. U.S.A.* 87:2211–2215 (1990); Samulski, R. J. et al, *E.M.B.O. J.* 10:3941–3950 (1991); Muzyczka, N., *Curr. Topics. Microbiol. Immunol.* 158: 97–129 (1992)). Recently, AAV was successfully used to deliver a reporter transgene to human hippocampal tissue (Freese, A. et al., *Epilesia* 38:759–766 (1997)).

Transgenes to be used in the viral vector include the full length cDNA encoding $\alpha_2M$ (SEQ ID NO:1), or the anti-LRP-A$\beta$ peptide described above. The construction of AAV-lacZ is described by Kaplitt, et al., and Samulski et al. (Kaplitt, M. G., et al, *Nature Genet.* 8:148–154 (1994); Samulski, R. J., et al., *J. Virol.* 63:3822–3888 (1989)). To insert the transgene into the viral vector, the viral vector is first cut with restriction enzymes. PCR mediated integration is used to create corresponding restriction sites at the 3' and 5' ends of the transgene, and the transgene is ligated with AAV.

The invention also provides a method of combating AD by administering the viral vector carrying an $\alpha_2M$, or an anti-LRP-Aβ peptide transgene and pharmaceutical compositions containing this viral vector.

The gene therapy of the invention can be administered using in vivo or ex vivo strategies. The in vivo approach involves the introduction of the viral vector directly into the tissue of the subject. In vivo methods of administration include direct injection into cerebrospinal fluid, or by stereotactic intracerebral inoculation into the hippocampus. In addition, some viral vectors, such as adenovirus, can be transported in a retrograde manner from the point of injection (Ridoux, V., et al., *Brain Res.* 648:171–175 (1994); Kuo, H., et al., *Brain Res.* 24:31–38 (1995)). Other routes of administration include nasal inhalation (Draghia, R., *Gene Ther.* 2:418–423 (1995)) and injection into the carotid artery after disruption of the blood brain barrier (Doran, S. E., et al., *Neurosurgery* 36:965–970 (1995); Muldoon, L. L., *Am. J. Pathol.* 147:1840–1851 (1995)).

For the ex vivo approach, a suitable cell type, such as fibroblasts myoblasts, or neural progenitor cells, is harvested from a donor and grown in tissue culture. The cells are then transfected, and the cells harvested and implanted in the subject. Ex vivo methods are described, for example, at Raymon, H. K., et al., *Exper. Neurol.* 144:82–91 (1997); Rosenberg, M. B., et al., *Science* 2442:1575–1578 (1988); Suhr, S. T., and Gage, F. H., *Arch. Neurol.* 50:1252–1268 (1993); Tuszynski, M. H., et al., *Exp. Neurol.* 126:1–14 (1994); Ridoux, V. et al., *Neuroreport* 5:801–804 (1994); Buc-Caron, M. H., *Neurobiol. Dis* 2:37–47 (1995); Sabaté, O., et al., *Nat. Genet.* 9:256–260 (1995).

The amount of viral vector carrying a transgene administered to a subject will vary depending upon the age, weight, and condition of the subject. The course of treatment may last from several days to several months or until a cure is effected or a diminution of disease state is achieved, or alternatively may continue for a period of years, for example, when used prophylactically. Optimal dosing schedules can be calculated from measurements of drug accumulation in the body. Persons of ordinary skill can easily determine optimum dosages, dosing methodologies and repetition rates. In general, dosage is from $1 \times 10^4$ to $1 \times 10^{10}$ plaque forming units (pfu), but is preferably $1 \times 10^6$ to $5 \times 10^7$ pfu/kg and may be given once daily, weekly, monthly or yearly.

The therapeutic agents of the invention can be administered alone, or in concert with one another or with other therapeutic agents. For example, a subject may be treated with both the anti-LRP-Aβ molecule and the antisense oligonucleotide of the invention, to provide both a supplement of A2M function, and to block defective A2M function at the same time.

Suitable subjects for carrying out the present invention are typically male or female human subjects, and include both those which have previously been determined to be at risk of developing AD, and those who have been initially diagnosed with AD. The present invention may be employed in combating both familial AD (late onset and early onset) as well as sporadic AD. One preferable group of subjects are those who have been determined to be heterozygous or homozygous for the A2M-2 allele. Procedures for selecting and assessing subjects who are heterozygous or homozygous for A2M-2 are described in Tanzi et al., U.S. Ser. No. 09/148,503, PCT Application No. PCT/US98/18535, and Blacker, D., et al., *Nat. Genet.* 19:357–360 (August 1998), all of which are herein incorporated by reference.

When the therapeutic agents as mentioned above are used as preventive or therapeutic agents for Alzheimer's disease, they may be made into preparations which satisfy the necessary requirements of the particular administering route together with usual carriers. For example, in the case of oral administration, preparations in the form of tablets, capsules, granules, diluted powder, liquid, etc. are prepared.

Pharmaceutical compositions containing the therapeutic agents of the invention, may be prepared in either solid or liquid form. To prepare the pharmaceutical compositions of this invention, one or more of the therapeutic agents is intimately admixed with a pharmaceutical carrier according to conventional pharmaceutical compounding techniques, which carrier may take a wide variety of forms depending on the form of preparation desired for administration, for example, oral or parenteral. By "pharmaceutically acceptable carrier" is meant a non-toxic solid, semisolid or liquid filler, diluent, encapsulating material, or formulation auxiliary of any type. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. In addition to such pharmaceutical carriers, cationic lipids may be included in the formulation to facilitate oligonucleotide uptake. One such composition shown to facilitate uptake is LIPOFECTIN (GIBCO-BRL, Bethesda, Md.).

Because of their ease in administration, tablets and capsules represent the most advantageous oral dosage unit form, in which case solid pharmaceutical carriers are employed. If desired, tablets may be sugar coated or enteric coated by standard techniques. For parenterally injectable compositions, the carrier will usually comprise sterile, pyrogen-free water, or sterile, pyrogen-free physiological saline solution, though other ingredients, for example, for purposes such as aiding solubility or for preservatives, may be included. Parenterally injectable suspensions (for example, for intravenous or intrathecal injection) may also be prepared, in which case appropriate liquid carriers, suspending agents and the like may be employed. See generally *Remington's Pharmaceutical Sciences* (18th ed.) Mack Publishing Co. (1990).

The pharmaceutical compositions of this invention may be administered in a number of ways depending upon whether local or systemic treatment is desired, and upon the area to be treated. Administration may be topical (including ophthalmic, vaginal, rectal, intranasal, transdermal), oral or parenteral, for example, by intravenous drip, subcutaneous, intraperitoneal or intramuscular injection or intrathecal or intraventricular administration. Formulations for topical administration may include transdermal patches, ointments, lotions, creams, gels, drops, suppositories, sprays, liquids and powders. Compositions for oral administration include powders or granules, suspensions or solutions in water or non-aqueous media, capsules, sachets, or tablets. Thickeners, flavorings, diluents, emulsifiers, dispersing aids or binders may be desirable. Compositions for intrathecal or intraventricular administration may include sterile aqueous solutions which may also contain buffers, diluents and other suitable additives. Formulations for parenteral administration may include sterile aqueous solutions which may also contain buffers, diluents and other suitable additives.

When necessary, the pharmaceutical composition may be prepared so that the therapeutic agent passes through the blood-brain barrier. One way to accomplish transport across the blood-brain barrier is to couple or conjugate the therapeutic agent to a secondary molecule (a "carrier"), which is either a peptide or a non-proteinaceous moiety. The carrier is selected such that it is able to penetrate the blood-brain barrier. Examples of suitable carriers are pyridinium, fatty acids, inositol, cholesterol, and glucose derivatives. Alternatively, the carrier can be a compound which enters the brain through a specific transport system in brain endothelial cells, such as transport systems for transferring insulin, or insulin-like growth factors I and II. This combination of therapeutic agent and carrier is called a prodrug. Upon entering the central nervous system, the prodrug may remain intact or the chemical linkage between the carrier and therapeutic agent may be hydrolyzed, thereby separating the carrier from the therapeutic agent. See generally U.S. Pat. No. 5,017,566 to Bodor.

An alternative method for transporting the therapeutic agent across the blood-brain barrier is to encapsulate the carrier in a lipid vesicle such as a microcrystal or liposome. Such lipid vesicles may be single or multi-layered, and encapsulate the therapeutic agent either in the center thereof or between the layers thereof. Such preparations are well known. For example, PCT Application WO 91/04014 of Collins et al. describes a liposome delivery system in which the therapeutic agent is encapsulated within the liposome, and the outside layer of the liposome has added to it molecules that normally are transported across the blood-brain barrier. Such liposomes can target endogenous brain transport systems that transport specific ligands across the blood-brain barrier, including but not limited to, transferring insulin, and insulin-like growth factors I and II. Alternatively, antibodies to brain endothelial cell receptors for such ligands can be added to the outer liposome layer. U.S. Pat. No. 4,704,355 to Bernstein describes methods for coupling antibodies to liposomes.

Another method of formulating the therapeutic agent to pass through the blood-brain barrier is to prepare a pharmaceutical composition as described above, wherein the therapeutic agent is encapsulated in cyclodextrin. Any suitable cyclodextrin which passes through the blood-brain barrier may be employed, including β-cyclodextrin, γ-cyclodextrin, and derivatives thereof. See generally U.S. Pat. No. 5,017,566 to Bodor; U.S. Pat. No. 5,002,935 to Bodor; U.S. Pat. No. 4,983,586 to Bodor.

Another method of passing the therapeutic agent through the blood-brain barrier is to prepare and administer a pharmaceutical composition as described above, with the composition further including a glycerol derivative as described in U.S. Pat. No. 5,153,179 to Eibl.

An alternative method of delivering the therapeutic agent to the brain is to implant a polymeric device containing the agent, which device is able to provide controlled release delivery of the agent to the brain for an extended period after implantation. Examples of such implantable polymeric devices are described in U.S. Pat. No. 5,601,835 to Sabel, and in U.S. Pat. No. 5,846,565, to Brem.

Another aspect of the invention relates to methods of screening for therapeutic agents for AD that can replace or supplement normal $\alpha_2M$ function and activities, and/or suppress defective $\alpha_2M$ function.

The invention provides for a method of screening for therapeutic agents for AD that can suppress the production of RNA encoding $\alpha_2M$-2 variants, and thereby suppress the production of $\alpha_2M$-2 variants. One embodiment of the invention is a method for screening for therapeutic agents by incubating cells that are heterozygous or homozygous for A2M-2, and that express A2M-2, with a test agent, and determining whether the agent increases the ratio of normal to aberrant A2M mRNA. Preferably the cells used are heterozygous for the A2M-2 allele, with the other allele being A2M-1 (A2M-1/2 cells). Examples of cells that may be used for this assay include, but are not limited to, glioma cells, hepatocytes, and hepatoma cell lines. In addition, cells used for the assay may be transformed or transfected to enable them to grow indefinitely in culture. To screen for these agents, the cells carrying are incubated with the test agent, preferably, for a period ranging from 2 hours to 24 hours. The incubation period may be longer or shorter depending on the agent, and suitable incubation periods can be determined by one of ordinary skill in the art. Cells homozygous for A2M-1 are used as a control. Procedures for A2M-2 genotyping are described in Tanzi et al., U.S. Serial No. 09/148,503, PCT Application No. PCT/US98/18535, and Blacker, D., et al., *Nat. Genet.* 19:357–360 (August 1998). After incubation, the ratio of normal to aberrant $\alpha_2M$ mRNA transcripts is determined, and compared to the ratio for cells (with the same genotype as the cells treated with agent) untreated with agent, and for A2M-1/1 cells untreated with agent. An increase in the ratio of normal to aberrant $\alpha_2M$ mRNA transcripts relative to this ratio for cells untreated with the agent would indicate an effective agent. This ratio for A2M-1/2 cells untreated with an agent is typically from 5:1 to 20:1. If the ratio of normal to aberrant $\alpha_2M$ mRNA transcripts approaches the ratio found in A2M-1/1 cells untreated with agent, the agent will be considered effective. Thus, for example, if the ratio in A2M-1/2 cells is 10:1, and the ratio in A2M-1/1 cells is 100:1, a test agent that results in the ratio to 20:1 would be considered effective.

The ratio of normal to aberrant transcripts may be quantitated by S1 nuclease analysis, or by RT PCR on RNA isolated from the glioma cells. Protocols for RNA isolation for cells in culture, and for S1 nuclease analysis is described in "Preparation and Analysis of RNA" in: *Current Protocols in Molecular Biology*, Ausubel, F. M., et al., eds., John Wiley & Sons, Inc., publ., Vol. 1, §4 (Suppl. 37 1997). S1 nuclease analysis is performed using a single-stranded antisense probe encompassing at least exons 17–18 (bp 2057–2284 of SEQ ID NO:1), synthesized from a full length A2M cDNA template (SEQ ID NO:1). Preferably, the probe would encompass exons 17, 18 and part of exon 19. The length of the probe is preferably from 250 bp to 500 bp long, and is more preferably 300 bp long. The probe may be up to 4353 bp (the length of the coding region), however, increasing the length of the probe may decrease the accuracy of the assay. In a preferred embodiment of the invention, the probe is complementary to nucleotides 2024–2323 of SEQ ID NO:1, in another preferred embodiment, the probe is complementary to nucleotides 2057–2384 of SEQ ID NO:1. After the RNA has been hybridized with the probe, and digested with S1 nuclease, samples are run on a polyacrylamide gel with molecular weight markers. Wild type mRNA transcript (A2M-1) should appear as a band corresponding to the length of the probe, for example, 300 bp, A2M-2 variant transcripts should appear as smaller bands. Total normal mRNA to total variant mRNA is compared and the ratio of normal to aberrant determined.

Alternatively, RT PCR may be used to quantitate mRNA transcripts. Protocols for RT PCR are described in "The Polymerase Chain Reaction" in: *Current Protocols in Molecular Biology*, Ausubel, F. M., et al., eds., John Wiley & Sons, Inc., publ., Vol. 2, §15.4 (Suppl. 17 1992). RNA isolated from the treated and control cells is amplified using RT PCR with labeled primers designed to amplify a region including at least exons 17–18 (bp 2057–2284 of SEQ ID NO:1), and preferably exons 17, 18 and part of exon 19. In addition, the primers may designed to target mRNA by synthesizing them so that they bind to the junction of two exons. For example, in a preferred pair of primers, the first primer would hybridize to A2M cDNA encoding the end of exon 16 and beginning of exon 17, and the second primer would hybridize to A2M cDNA encoding the end of exon 18, and beginning of exon 19. The primers may be from 8–50 nucleotides in length, but are preferably 15–30 nucleotides in length, and are more preferably 15 nucleotides in length. The PCR product is then run on a polyacrylamide gel with molecular weight markers. Bands corresponding to wild type mRNA transcripts should correspond to the length of A2M-1 cDNA corresponding to the far ends of the primers used. For example, wild type mRNA amplified by primers designed to amplify the last 5 base pairs of exon 16 to the first 5 base pairs of exon 19 (bp 2052–2289 of SEQ ID NO:1), would be 238 nucleotides. If the primers were designed to amplify a region starting at the beginning of exon 17, including exon 18, and ending after the first 100 nucleotides of exon 19 (bp 2057–2456 of SEQ ID NO:1) the expected fragment length would be 400 nucleotides for normal mRNA. Variant mRNA transcripts will be shorter. Total normal mRNA to total variant mRNA is compared and the ratio of normal to aberrant determined.

Other methods of RNA quantitation that may be used in the invention are well known in the art, and are described in, for example, *PCR Protocols, A Guide to Methods and Applications,* Innis, A., et al., eds., Academic Press, Inc., San Diego, Calif., pub., pp. 60–75 (1990).

Another embodiment of the invention is to screen for nontoxic agents that can activate $\alpha_2M$ through mechanisms other than cleavage of the bait domain. For $\alpha_2M$ tetramers having one or more $\alpha_2M$-2 monomers, protease activation of the bait domain may be impaired. Because activation is required to expose the LRP binding domain, impairment of activation of one or more monomers of a tetramer would result in a decreased ability to bind to LRP. Consequently, these tetramers would be inefficient at clearing $A\beta$ through LRP mediated endocytosis. However, $\alpha_2M$ may be activated through mechanisms other than protease cleavage of the bait domain. For example, agents other than proteases, such as methylamine, activate $\alpha_2M$ through the thiolester site. These agents would be able to activate defective $\alpha_2M$ monomers, exposing the LRP binding domain (and other domains) and potentially allowing for LRP mediated clearance of $A\beta$. In addition, these agents could be used to increase the amount of active wild type $\alpha_2M$ tetramers, to compensate for defective $\alpha_2M$ tetramers. Presently, effective nontoxic agents capable of activating $\alpha_2M$ at sites other than the bait domain are unknown. The invention provides for a method of screening for such agents.

To screen for these agents, $\alpha_2M$ is treated with a test agent, and then tested to determine whether it has undergone a conformational change, or for its ability to bind to LRP. The $\alpha_2M$ used for the assay may be wild type $\alpha_2M$, $\alpha_2M$-2, or $\alpha_2M$ mutants that are missing all, or a portion of the bait domain. However, preferably, wild type $\alpha_2M$ is used. In addition, $\alpha_2M$ used for the assay may be in the form of dimers or tetramers, but is preferably in the form of tetramers. For treatment of $\alpha_2M$ with the test agent, the $\alpha_2M$ is preferably incubated with the test agent for 2–24 hours. However, the incubation period may be longer or shorter according to the agent, and suitable incubation periods can be determined by one of ordinary skill in the art. To determine whether treated $\alpha_2M$ has undergone a conformational change, the $\alpha_2M$ electrophoretic-mobility assay may be used. To determine the ability of treated $\alpha_2M$ to bind to LRP, any method of measuring LRP binding may be used, however, preferred methods include enzyme-linked immunosorbent assays (ELISA), immunoblotting, LRP mediated endocytosis, and LRP mediated degradation.

The $\alpha_2M$ electrophoretic mobility assay can also be used to determine whether treated $\alpha_2M$ has been activated, by determining whether treated $\alpha_2M$ has undergone the conformational change expected for activated $\alpha_2M$. The $\alpha_2M$ electrophoretic-mobility assay consists of analyzing the electrophoretic mobility of $\alpha_2M$ under non-denaturing conditions after incubation with the test agent, or as a control, a protease, or other reagent capable of converting $\alpha_2M$ to the fast form (Barret, A. J., et al., *Biochem. J.* 181:401–418 (1979); Bowen, M. E., and Gettins, P. W., *J. Biol. Chem.* 273:1825–1831 (1998)). $\alpha_2M$ can exist in two forms easily distinguishable by mobility in gel electrophoresis (Barret, A. J., et al., *Biochem. J.* 181: 401–418 (1979)). The difference in mobility is due to the conformational change that $\alpha_2M$ undergoes after activation with a protease or other agent, such as methylamine. This conformational change results in an increase in electrophoretic mobility on poly-acrylamide gels run under non-denaturing conditions (this form is referred to as the "fast form" of $\alpha_2M$) (Barret, A. J., et al., *Biochem. J.* 181:401–418 (1979); Bowen, M. E., and Gettins, P. W., *J. Biol. Chem.* 273:1825–1831 (1998)). This "slow to fast" conversion is used as the basis for an assay for this conformational change, and the two different $\alpha_2M$ conformations are referred to as the slow and fast forms (Bowen, M. E., and Gettins, P. W., *J. Biol. Chem.* 273:1825–1831 (1998)). Conversion from the slow to fast form for $\alpha_2M$ treated with a test agent would indicate that the agent had activated $\alpha_2M$. Where this assay is used to determine the effectiveness of a test agent, the $\alpha_2M$ treated with the agent would preferably be tetrameric.

The $\alpha_2M$ electrophoretic mobility assay and methods of purifying $\alpha_2M$ from serum are described by Barret et al. in Barret, A. J., et al., *Biochem. J.* 181:401–418 (1979), and by Bowen et al. in Bowen, M. E., et al., *Arch. Biochem. Biophys.* 337:191–201 (1997), and in Bowen, M. E., and Gettins, P. W., *J. Biol. Chem.* 273:1825–1831 (1998). After incubation with the test agent, the $\alpha_2M$ sample may be run on polyacrylamide gel under nondenaturing conditions, such as those described in Bowen, M. E., et al., *Arch. Biochem. Biophys.* 337:191–201 (1997). The $\alpha_2M$ sample may be detected by methods well known in the art such as by radiolabelling the protease used, or by Western Blot using anti-$\alpha_2M$ antibodies. Activated and unactivated $\alpha_2M$ may be used as controls for comparison of electrophoretic mobility with the sample being analyzed.

In one embodiment of the invention, ELISA is used to determine the ability of treated $\alpha_2M$ to bind to LRP. ELISA protocols are described in "Immunology" in: *Current Protocols in Molecular Biology,* Ausubel, F. M., et al., eds., John Wiley & Sons, Inc., publ., Vol. 2, §11.2 (Suppl. 15 1991). In this assay, microtiter plate wells coated with an anti-$\alpha_2M$ IgG that recognizes only activated $\alpha_2M$, such as the antibody described by Marynen et al., (Marynen, P., et al., *J. Immunol.* 127: 1782–1786 (1981)), are incubated with the treated $\alpha_2M$, or control molecule. The wells are then incubated with an enzyme-conjugated anti-$\alpha_2M$ IgG and rinsed. Next, the wells are incubated with the substrate for the enzyme conjugate, rinsed, and the amount of $\alpha_2M$ sample bound in the well is determined. Alternatively, microtiter plate wells are coated with anti-LRP IgG and rinsed. The wells are then incubated with LRP and rinsed. This LRP is preferably soluble LRP. Then the wells are incubated with $\alpha_2$M treated with the test agent, untreated $\alpha_2$M, or activated $\alpha_2$M, and rinsed. Next the wells are incubated with enzyme-conjugated anti-$\alpha_2$M IgG, rinsed again, and then incubated with the substrate for the enzyme that is conjugated to the anti-$\alpha_2$M IgG. The amount of $\alpha_2$M sample bound in the well is then determined. In another embodiment, wells coated with LRP are incubated with $\alpha_2$M treated with the test agent, untreated unactivated $\alpha_2$M, or untreated activated $\alpha_2$M, and rinsed. The wells are then incubated with enzyme-conjugated anti-$\alpha_2$M IgG, rinsed, and then treated with the enzyme substrate, and the amount of $\alpha_2$M sample bound is determined. The anti-$\alpha_2$M IgG may be conjugated with, for example, horseradish peroxidase, urease or alkaline phosphatase, but is preferably labeled with a fluorescent label, such as 4-methylumbelliferyl phosphate (MUP). The appropriate substrate is added to the wells, the wells are washed, and then quantitated with a microtitre plate reader.

Alternatively, the ability of $\alpha_2$M treated with the test agent to bind to LRP may be determined by immunoblotting methods. Unlabeled soluble LRP is incubated separately with $\alpha_2$M treated with the test agent, untreated unactivated $\alpha_2$M, and untreated $\alpha_2$M activated by methylamine or trypsin. Samples are then electrophoresed on a 5% SDS-PAGE, under non-reducing conditions, transferred to polyvinyl difluoride nitrocellulose membrane, and probed with anti-$\alpha_2$M IgG and anti-LRP IgG. If the $\alpha_2$M treated with the test agent may be detected by both anti-$\alpha_2$M IgG and anti-LRP IgG it can be concluded that the treated $\alpha$2M can bind A$\beta$. In another method of immunoblotting, an antibody specific for the LRP binding domain of $\alpha_2$M, such as that described by Marynen, et al, (Marynen, P., et al.,*J. Immunol.* 127: 1782–1786 (1981)), is used as the anti-$\alpha_2$M IgG, and the samples are not incubated with LRP. Recognition of the treated $\alpha_2$M by this antibody indicates that $\alpha_2$M has been activated.

In addition, the ability of $\alpha_2$M treated with a test agent to bind to LRP can be determined by its ability to undergo LRP mediated endocytosis using cell culture experiments as described by Kounnas et al. (Kounnas, M. Z., et al., *Cell* 82:331–340 (1995); Kounnas, M. Z., et al., *J. Biol. Chem.* 270:9307–9312 (1995)). Cells expressing LRP, mouse embryo fibroblasts, are incubated for 18 hours with $^{125}$I-A$\beta$ (alternatively, A$\beta$ may be labeled with $^3$H or $^{14}$C) in the presence or absence of with $\alpha_2$M treated with the test agent, untreated unactivated $\alpha_2$M, and untreated $\alpha_2$M activated by methylamine or trypsin, in the presence or absence of RAP (400 nM). RAP is an inhibitor of LRP ligand binding, and is added to determine if endocytosis is LRP mediated. In addition, chloroquine (0.1 mM) is added to inhibit lysosomal degradation of $^{125}$I-A$\beta$.

The amount of radioactive ligand released by treatment with trypsin-EDTA, proteinase K solution defines the surface-bound material, and the amount of radioactivity associated with the cell pellet defines the amount of internalized ligand. Activated $\alpha_2$M/$^{125}$I-A$\beta$ will serve as positive control. Under the conditions described, more than 4–8 fmoles/$10^4$ cells of activated $\alpha_2$M/$^{125}$I-A$\beta$ should be internalized after 18 hours of incubation (Kounnas, M. Z., et al., *Cell* 82:331–340 (1995)). Unactivated $\alpha_2$M/$^{125}$I-A$\beta$ and activated $\alpha_2$M/$^{125}$I-A$\beta$ in the presence of RAP should not be internalized, therefore, no more than 2–4 fmoles/$10^4$ cells should be internalized. If the amount of test agent treated $\alpha_2$M/$^{125}$I-A$\beta$ is greater than 4–8 fmoles/$10^4$ cells, it can be concluded that $\alpha_2$M/$^{125}$I-A$\beta$ has the ability to undergo LRP mediated endocytosis. In addition, unactivated $\alpha_2$M/$^{125}$I-A$\beta$, and activated $\alpha_2$M/$^{125}$I-A$\beta$ in the presence of RAP should not be internalized, therefore no more than 2–4 fmoles/$10^4$ cells should be internalized (Kounnas, M. Z., et al., *Cell* 82:331–340 (1995)). Internalization of the treated $\alpha_2$M/$^{125}$I-A$\beta$ complex will be deemed abolished if treated $\alpha_2$M/$^{125}$I-A$\beta$, in the presence and absence of RAP, and unactivated $\alpha_2$M/$^{125}$I-A$\beta$ show the same amount of radioactivity associated with the cell pellet.

To determine the ability of treated $\alpha_2$M/A$\beta$ complexes to undergo degradation after endocytosis, this cell culture protocol is repeated without chloroquine. The radioactivity appearing in the cell culture medium that is soluble in 10% trichloroacetic acid is taken to represent degraded $^{125}$I-A$\beta$ (Kounnas, M. Z., et al., *Cell* 82:331–340 (1995); Narita, M., et al., *J. Neurochem.* 69:1904–1911 (1997)). Total ligand degradation is corrected for the amount of degradation that occurs in control wells lacking cells. Because free $^{125}$I-A$\beta$ can be degraded in an LRP independent manner, degradation is measured for treated $\alpha_2$M, and untreated $\alpha_2$M complexes with $^{125}$I-A$\beta$, as well as for free $^{125}$I-A$\beta$, in the presence and absence of RAP. Using the same positive and negative controls as above, if RAP does not decrease the amount of TCA soluble radioactivity by at least 30% for the treated $\alpha_2$M/$^{125}$I-A$\beta$ complex, it can be concluded that $^{125}$I-A$\beta$ ligand of treated $\alpha_2$M is not degraded.

It will be readily apparent to those skilled in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLE 1

In view of the link between the inheritance of A2M-2, and the role of $\alpha_2$M in brain, the potential effects of the A2M-2 deletion polymorphism on A2M mRNA and on the $\alpha_2$M protein were investigated. These studies were complicated by the fact the polymorphism does not directly alter the coding sequence of $\alpha_2$M, but consists of an intronic deletion just before the exon 18 splice acceptor site (Matthijs, G., et al., *Nucleic Acids Res.* 19:5102 (1991)). If exon 18 were to be deleted as a result of the A2M-2 polymorphism, this deletion would result in the loss of half of the active center or "bait" region of $\alpha_2$M (specifically, deletion of the last 20 amino acids out of the 39 amino acids forming the bait region), with likely adverse functional consequences for $\alpha_2$M activity. With specific regard to A$\beta$, the peptide does not directly bind to the bait region. However, recognition and cleavage of the bait domain by target proteases is a necessary prerequisite in vivo for activation of $\alpha_2$M via a conformational change in the $\alpha_2$M tetramer. Activation of $\alpha_2$M then results in the presentation of the LRP-binding domains which is essential for binding to LRP (Borth, W., *FASEB J.*6:3345–3353 (1992)). Thus, clearance of $\alpha_2$M ligands (for example, cytokines, growth factors, A$\beta$), would be hampered by deletion of the bait domain (exon 18).

A specific deletion of exon 18 due to the A2M-2 deletion would also result in a frame-shift in the coding region in exon 19, resulting in the synthesis of a truncated $\alpha_2$M monomer. Therefore, one likely consequence of a modification of the bait region is the formation of a defective $\alpha_2$M tetramer (insertion of defective monomer) which could not be activated and undergo subsequent endocytosis via LRP. Experiments with an exon 18 deleted $\alpha_2$M construct expressed in cells indicate that a truncated $\alpha_2$M protein at the bait region can still be secreted and form tetramers with itself. In addition, only human glioma cell lines positive for the A2M-2 allele produced altered A2M message and corresponding truncated $\alpha_2M$ monomers consistent with a deletion of exon 18 followed by termination of the amino acid sequence in exon 19.

Methods and Results

First, the effect of the A2M-2 deletion on RNA splicing and on $\alpha_2M$ complex formation and secretion were investigated. To study the biological effects of the A2M-2 polymorphism in an endogenous system, 15 human glioblastoma cell lines expressing high levels of $\alpha_2M$ were genotyped (Blacker, D., et al., *Nature Genetics* 19:357–360 (1998)). While the highest levels of $\alpha_2M$ would be expected from hepatoma cell lines, glioblastomas were chosen because of their CNS origin. Ten primary glioblastoma cell lines (all derived from different patients) were homozygotes for the A2M-1 (no deletion) allele, while 3 cell lines were A2M-1/2 heterozygotes for the deletion. Two cell lines did not qualify for either of these alleles and were excluded from further studies. At the molecular level, the A2M-2 allele consists of a deletion of 5 bp (ACCAT) in the consensus polypyrimidine tract immediately prior to the consensus 3' AG at the splice acceptor site of exon 18 (Matthijs, G., et al., *Nucleic Acids Res.* 19:5102 (1991)). Given the position of the polymorphism, aberrant A2M RNA splicing might be expected to lead to a deletion at exon 18 since the consensus polypyrimidine tract would be reduced by 3 pyrimidines (to a minimal consensus configuration for exon splicing). Deletion of exon 18 would, in turn, result in termination of the protein due to a stop codon in exon 19. Reverse transcription-PCR (RT-PCR) was employed in attempts to identify aberrant splice products in the vicinity of exon 18 of the A2M gene. An expected 399 bp fragment encompassing exons 17, 18, and 19 was amplified by RT-PCR of RNA isolated from the 13 human glioma cell lines. Agarose gel/ethidium bromide staining was not sensitive enough to reveal aberrant A2M transcripts in any of the cell lines containing the A2M-2 allele. However, using polyacrylamide gels, various $^{33}$P-labeled PCR products ranging in size between 250–290 bp were detected. These products were found exclusively in the A2M-1/2 cell lines (FIG. 1).

Figure 2:
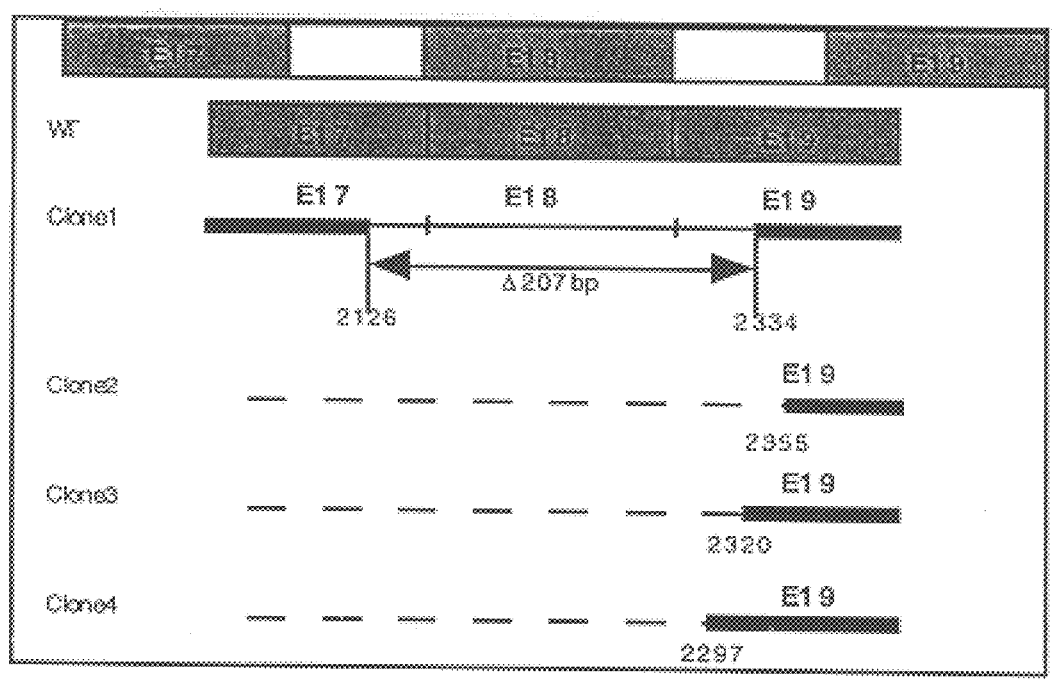
FIG. 2.

Next, these products were cloned into the vector pCR 2.1. Four different clones representing aberrant mRNA transcripts have been identified using this approach (FIG. 2). Sequencing of these clones revealed aberrant splicing events around exon 18 leading to the production of variably sized RNAs in which exon 17 and/or 19 may also be shortened. Clone 1 has a 208 bp deletion (2126–2334) including exon 18 and, interestingly, also 42 and 50 bp of exons 17 and 19, respectively. The protein product resulting from such a deletion would still be in frame with 69 amino acids missing, including most of the bait region. Clones 2, 3, and 4 contain unidentified DNA fragments which continue within exon 19 to bp 2355, 2320, and 2297 respectively. The unknown sequences are most likely intronic sequences that are not accessible in DNA databases. Therefore, aberrant splicing events around exon 18 do not appear to simply result in the precise deletion of exon 18. Rather, they lead to the production of variably sized RNAs in which exons 17 and/or 19 may also be partly deleted.

Figure 3:
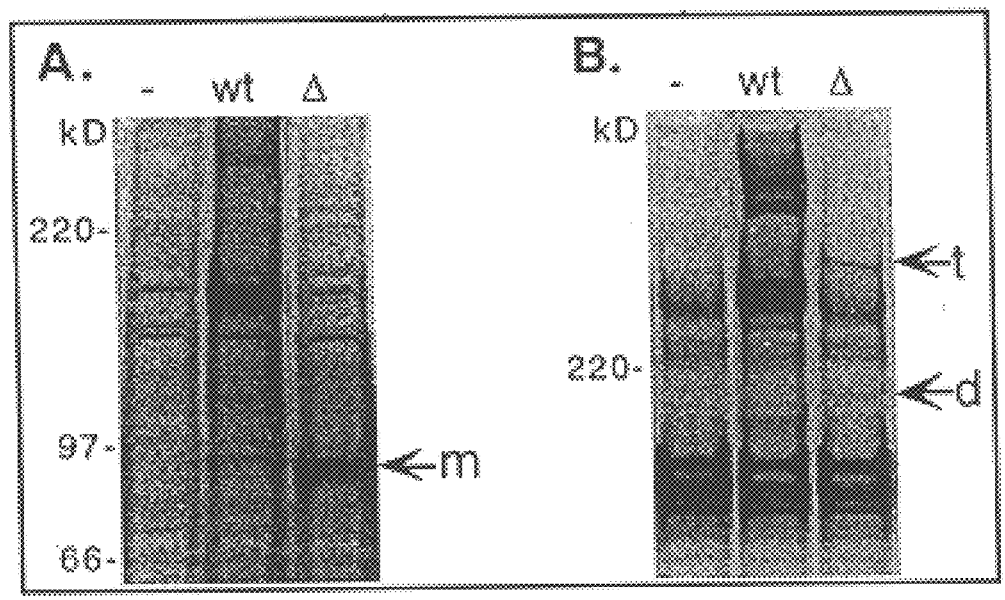
FIG. 3.

Next, experiments designed to detect mutant forms of $\alpha_2M$ protein containing large deletions or truncations were performed. Based on the low level of aberrant mRNA transcripts, the expected amount of mutant proteins could be below detection or not recognized by the antibody used, since the antibody was raised against the holoprotein. Finally, a truncated or grossly altered protein may be targeted by the quality control system in the ER for degradation prior to secretion. These concerns were addressed by producing an A2M cDNA construct in which a stop codon is inserted in the middle of exon 18 and transfecting this construct into chinese hamster ovary (CHO) cells, which do not produce $\alpha_2M$ endogenously. As seen in FIG. 3, both media and extracts from the transfected cells contained truncated and the control full-length $\alpha_2M$ protein products. The gels shown were run under denaturing but non-reducing conditions. Under these conditions, monomers of the truncated protein and monomers and dimers of the full-length protein were detected in the cell lysate. In the media, however, almost all of the truncated protein formed tetramers, and dimers were barely detectable. Wild-type full-length $\alpha_2M$ was also present in the media mainly in the form of tetramers and dimers. Besides demonstrating that the antibody used is able to recognize the N-terminal half of $\alpha_2M$ and that a truncated $\alpha_2M$ protein can be synthesized and secreted by CHO cells, the results of this experiment (FIG. 3) also provided preliminary data indicating that secreted $\alpha_2M$ levels may dramatically decrease as a result of the truncation.

Figure 4:
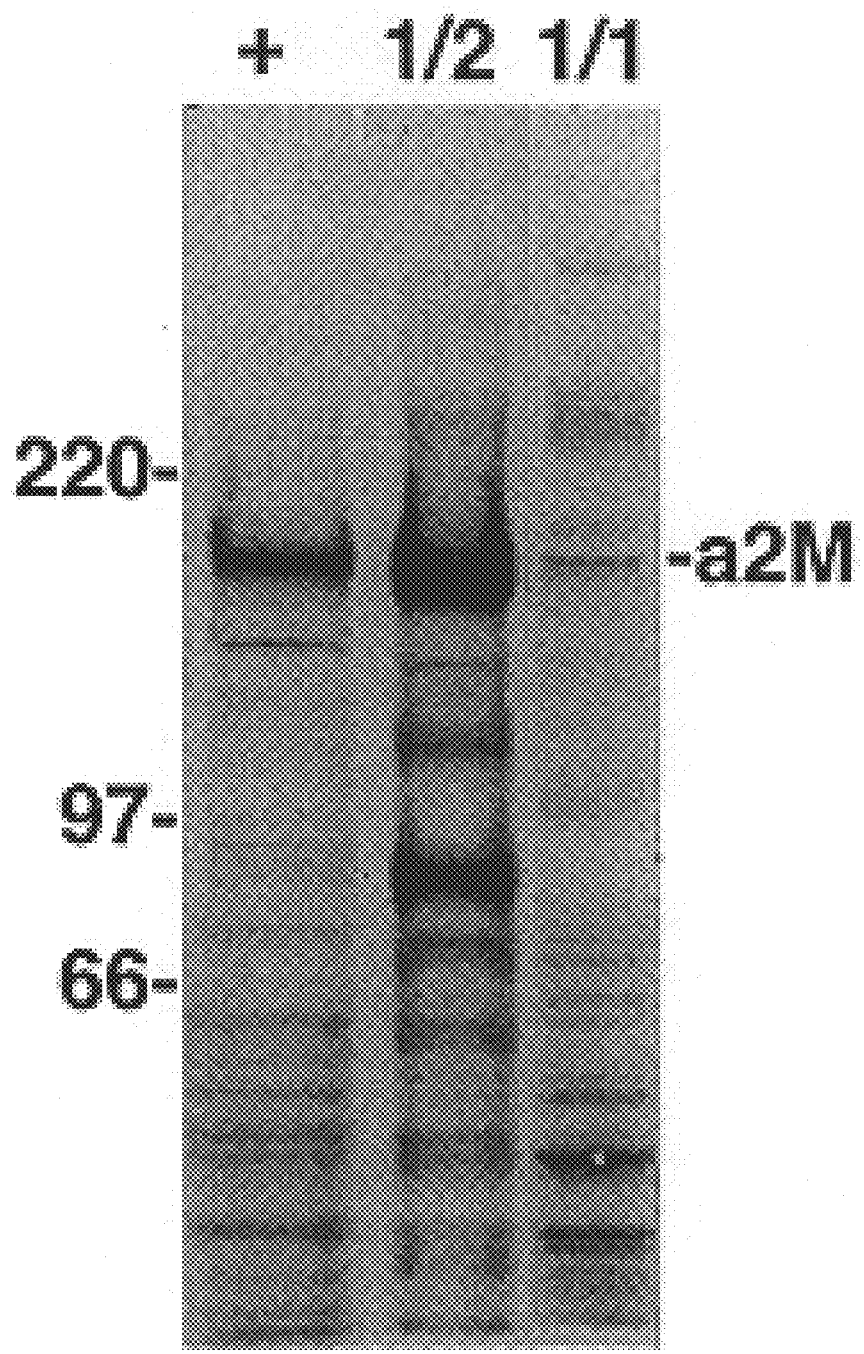
FIG. 4.

Next, the effects of the A2M-2 polymorphism on secretion and tetramer formation of endogenous $\alpha_2M$ were examined. For this purpose, endogenous secreted $\alpha_2M$ was analyzed by Western blot analysis. Glioblastoma cells were cultured overnight in OptiMem (Gibco) serum-free media (as bovine serum contains high levels of $\alpha_2M$), and secreted $\alpha_2M$ was immunoprecipitated with a polyclonal $\alpha_2M$ antibody obtained from Sigma. When the immunoprecipitate was resolved by SDS PAGE, the expected 180 kD monomer was detected in all lines tested, however, smaller aberrant forms of $\alpha_2M$ were detected only in the A2M-2 positive cells. FIG. 4 shows cell lysates from wild-type and A2M-2 deletion-bearing cells. The data revealed protein bands consistent with truncated forms of $\alpha_2M$ exclusively in the A2M-2 deletion-containing cells. The media (data not shown) from A2M-1 and A2M-2 cells contained primarily full-length $\alpha_2M$ monomers, but in the media from the A2M-2 cells small amounts of truncated species could also be observed.

Discussion

A reduced steady-state level of secreted $\alpha_2M$, or the presence of defective tetramers due to dominant negative effects of A2M-2, could result in impaired $\alpha_2M$ function. Partial or total deletion of the sequences coding for the bait region in exons 17 and 18 are likely to modify protease binding, activation, and internalization of potentially defective tetramers containing mutant monomer(s). Therefore, the generation of very low levels of mutant monomers may have an amplified effect as one mutant monomer may potentially inhibit the function of three wild-type monomers in the tetramer (dominant negative effect). Based on these and the linkage between the A2M-2 deletion and AD (Blacker, D., et al., *Nat. Genet.* 19:357–360 (1998)), a critical role for $\alpha_2M$ is indicated in AD neuropathogenesis. The data described herein show that the A2M-2 deletion leads to deleted/truncated forms of $\alpha_2M$ RNA and protein that may have a dominant negative effect on normal $\alpha_2M$.

EXAMPLE 2

To test the A2M-2 antisense oligonucleotides of the invention, and the S1 nuclease assay, A2M-2 antisense oligonucleotides having the nucleotide sequences of nucleotides 35–50, and 20–50 of SEQ ID NO:27 are synthesized using an automatic DNA synthesizer (MilliGen). The oligonucleotides recovered from 20% acrylamide-urea gel, and purified by means of an ethanol precipitating method, and the precipitate is dissolved in water at a concentration of 1 µmol. A2M-2 sense oligonucleotides complementary to each of the antisense nucleotides are used as a positive control. Each of the antisense or sense oligonucleotides (1 µmol) is added to 1 ml cell culture medium. Each 1 ml sample is then incubated with glioma cells heterozygous for the A2M-2 allele, or homozygous for wild type A2M (A2M-1) at 37° C. for 24 hours. The cells are washed with phosphate buffered saline, and homogenized in a denaturing solution containing 4 M guanidine thiocyanate. RNA is extracted using phenol/chloroform extraction and ultracentrifugation. The RNA pellet is then rinsed with 1 ml 75% ethanol/25% 0.1 M sodium acetate, and resuspended in 100 µl water. RNA from each sample is then probed using a 300 bp antisense DNA probe encompassing exons 17 and 18 (nucleotides 2057–2356 of the full length cDNA for $\alpha^2$M (SEQ ID NO:1)) end labeled with $^{32}$P. The probe is hybrized with 15 µg RNA from each sample. The RNA is then precipitated, washed and resuspended with S1 hybridization solution. The samples are then denatured for 10 minutes at 65° C., and hybridized overnight at 30° C. 300 U S1 nuclease buffer in 150 µl S1 nuclease buffer with single-stranded calf thymus DNA is then added to each sample and incubated for 60 minutes at 30° C. The reaction is stopped, the RNA precipitated, washed, and resuspended, and the samples are run on a polyacrylamide gel with molecular weight markers. Wild type transcripts (A2M-1) should appear as 300 bp bands, A2M-2 variant transcripts should appear as smaller bands. Without A2M-2 antisense oligonucleotide treatment, this ratio is expected to be approximately 10:1 wild type to variant mRNA. The ratio of wild type to variant transcripts is determined and compared to the ratio found for A2M mRNA from A2M-1/1 cells.

EXAMPLE 3

To screen for therapeutic agents capable of activating $\alpha_2$M through a site other than the bait domain, unactivated tetrameric $\alpha_2$M (Sigma) (about 1 mg/ml) is incubated with 5, 20, 50 or 100 µg of test agent in Tris/HCl or sodium phospate buffer at 37° C. for 2 hours. Untreated unactivated $\alpha_2$M, and untreated $\alpha_2$M activated with methylamine or trypsin are used as controls.

Microtiter plates are incubated for 2 h at 37° with 50 µl of LRP (10 µg)/well, and then rinsed with deionized water. The plates are then filled with blocking buffer and rinsed. 50 µl of treated $\alpha_2$M, untreated unactivated $\alpha_2$M, or untreated $\alpha_2$M activated with methylamine or trypsin is added to each well and incubated for 2 h at room temperature. After rinsing, 50 µl anti-$\alpha_2$M IgG conjugated with MUP in blocking buffer is added to the wells and incubated for 2 h at room temperature. After rinsing, MUP substrate is added to the wells, and incubated for 1 h at room temperature. The amount of $\alpha_2$M bound is quantitated with a spectrofluorometer with a 365-nm excitation filter and 450 µm emission filter.

EXAMPLE 4

Given the evidence that only a few key interactions are required for $\alpha_2$M binding to LRP and A$\beta$ (as discussed above), a small peptide containing LRP and A$\beta$ binding domains could promote A$\beta$ binding, LRP mediated endocytosis, and finally A$\beta$ degradation. Such a peptide could serve as a substitute for $\alpha_2$M-2 if it is not able to promote A$\beta$ clearance and degradation.

Protein-protein interactions are usually mediated by a few key interactions (Wells, J. A., Proc. Natl. Acad. Sci. USA. 93:1–6 (1996)). The A$\beta$ clearance properties of $\alpha_2$M do not require all the domains of an intact 5804 residue $\alpha_2$M tetramer. A 250-residue fragment of the $\alpha_2$M monomer contains both the A$\beta$ and LRP binding domains (Hughes, S. R., et al., Proc. Natl. Acad. Sci. U.S.A. 95:3275–3280 (1998)). An 11-residue peptide can bind A$\beta$ in vivo and a 27 residue LRP binding consensus sequence exists (Soto, C., et al., Nat. Med. 4:822–826 (1998); Nielsen, K. L., et al., J. Biol. Chem. 271:12909–12912 (1996); Soto, C., et al., Biochem. Biophys. Res. Commun. 226:672–680 (1996)). A peptide containing an A$\beta$ and an LRP binding domain could bind A$\beta$ and target it for LRP mediated endocytosis followed by lysosomal degradation. To achieve this goal, first, a peptide consisting of an 11-residue A$\beta$ binding peptide and a 27 residue LRP binding domain is produced and tested for A$\beta$ binding and clearance properties. If necessary, the binding properties of this anti-LRP-A$\beta$ peptide can be reoptimized using in vivo evolution techniques (Buchholz, F., et al., Nat. Biotechnol. 16:657–662 (1998)).

Methods

Figure 6:
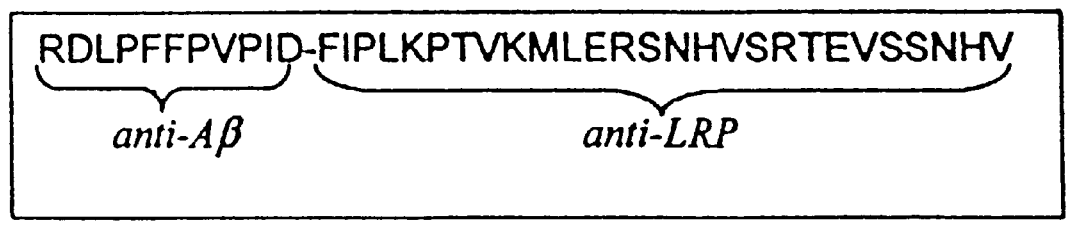
FIG. 6.

FIG. 6 shows the sequence of one possible anti-LRP-A$\beta$ peptide. Using standard solid phase synthesis methods this peptide is synthesized in quantities sufficient to carry out tests to determine function in A$\beta$ clearance. (See "Preparation and Handling of Peptides," in: Current Protocols in Protein Science, Coligan, J. E., et al., eds., John Wiley and Sons, Inc., pub., Vol. 2., Chapter 18 (Suppl. 14 1998)). DNA encoding the fusion peptide is then synthesized. The DNA coding for the 27 residue LRP binding peptide is obtained by PCR amplification of codons 1366 to 1392 of the A2M gene (Nielsen, K. L., et al., J. Biol. Chem. 271:12909–12912 (1996)). To integrate the 11 residue A$\beta$ binding sequence into the LRP binding sequence PCR mediated insertion is used. A 55 nucleotide 5' PCR primer is designed that has 25 nucleotides of homology to the LRP binding sequence and 36 nucleotides corresponding to the 11 residues of the A$\beta$ binding peptide and a start codon. PCR mediated insertion is also used to insert an Xho I and Kpn I restriction enzyme sites at the 5' and 3' ends of the fusion gene, respectively. Cleavage with these enzymes will facilitate cloning of the fusion protein gene into (i) the pBAD/His expression vector (Invitrogen), for arabinose dependent expression of anti-LRP-A$\beta$ in E. coli, and (ii) the pLex9-3H vector for use in the yeast three hybrid system (Tirode, F., et al., J. Biol. Chem. 272:22995–22999 (1997)). The protein product, named anti-LRP-A$\beta$, of the resulting gene should have both A$\beta$ and LRP binding properties.

A$\beta$ Binding. The ability of anti-LRP-A$\beta$ to bind A$\beta$ is first determined by gel-filtration chromatography and immunoblotting. Both of these methods have been used successfully by other investigators to investigate A$\beta$ binding to wild type and variant $\alpha_2$M (Narita, M., et al., J. Neurochem. 69:1904–1911 (1997); Du, Y., et al., J. Neurochem. 69:299–305 (1997)). A$\beta$1-42 is iodinated with $^{125}$I, following the procedure of Narita et al. (Narita, M., et al., J. Neurochem. 69:1904–1911 (1997)). $^{125}$I-A$\beta$ (5 nmol) is incubated separately with anti-LRP-A$\beta$, unactivated $\alpha_2$M, unactivated $\alpha_2$M-2, $\alpha_2$M activated by methylamine or trypsin, or $\alpha_2$M-2 activated by methylamine or trypsin. A ten fold molar excess of A$\beta$ is used and the samples are incubated in 25 mM Tris-HCl, 150 mM NaCl, pH 7.4 for two hours at 37° C. Controls containing only $^{125}$I-A$\beta$ are also incubated. The anti-LRP-A$\beta$/$^{125}$I-A$\beta$, $\alpha_2$M/$^{125}$I-A$\beta$, and $\alpha_2$M-2/$^{125}$I-A$\beta$ complexes are separated from unbound 125I-A$\beta$ using a Superose 6 gel-filtration column (0.7×20 cm) under the control of an FPLC (Pharmacia). 25 MM Tris-HCl, 150 mM NaCl, pH 7.4 are used to equilibrate the column and elute the samples. Using a flow rate of 0.05 ml/minute, 200 μL fractions are collected. Having standardized the column with molecular weight markers ranging from 1000 kD to 4 kD, anti-LRP-Aβ/$^{125}$I-Aβ, α$_2$M/$^{125}$I-Aβ, and α$_2$M-2/$^{125}$I-Aβ fractions are counted in a γ counter to determine the elution profile of $^{125}$I-Aβ. If anti-LRP-Aβ has bound $^{125}$I-Aβ, $^{125}$I-Aβ should be detected by gamma counter at two peaks, one corresponding to the molecular weight of the anti-LRP-Aβ/$^{125}$I-Aβ complex (about 8–9 kD for this anti-LRP-Aβ peptide), and one corresponding to the molecular weight of $^{125}$I-Aβ (4.5 kD).

It is unlikely, but possible, that iodinated Aβ may lead to a false positive or negative binding. Therefore, immunoblotting experiments are undertaken to confirm the results of the gel-filtration chromatography experiment (Narita, M., et al., *J. Neurochem.* 69:1904–1911 (1997); Du, Y., et al., *J. Neurochem.* 69:299–305 (1997)). Unlabeled Aβ is incubated separately with anti-LRP-Aβ, unactivated α$_2$M, unactivated α$_2$M-2, α$_2$M activated by methylamine or trypsin, or α$_2$M-2 activated by methylamine or trypsin, under the same conditions described above. Samples are electrophoresed on a 5% SDS-PAGE, under non-reducing conditions, and transferred to polyvinyl difluoride nitrocellulose membrane (Immobilon-P). These membranes are probed with polyclonal anti-α$_2$M IgG or monoclonal anti-Aβ IgG. Immunoreactive proteins are visualized using ECL and peroxidase conjugated anti-rabbit IgG. Molecular mass markers are used to determine if the immunoreactive proteins from the anti-α$_2$M and anti-Aβ blots for corresponding lanes display the same mobility. If the immunoreactive proteins display the same mobility then it will be concluded that Aβ binds anti-LRP-Aβ.

Endocytosis. The ability of anti-LRP-Aβ/Aβ complexes to undergo LRP mediated endocytosis and subsequent degradation is determined in cell culture experiments. The amount of radioligand that is internalized or degraded by cells has been described previously (Kounnas, M. Z., et al., *Cell* 82:331–340 (1995); Kounnas, M. Z., et al., *J. Biol. Chem.* 270:9307–9312 (1995)). Mouse embryo fibroblasts, which are cells that express LRP, are plated in 12 well plates to a density of 2×10$^5$ cells per well, and grown for 18 hours at 37° C. in 5% CO$_2$. Cells are incubated in 1% Nutridoma (Boehringer Mannheim), penicillin/streptomycin, 1.5% bovine serum albumin for one hour prior to addition of $^{125}$I-Aβ in the presence or absence of anti-LRP-Aβ, unactivated α$_2$M, unactivated α$_2$M-2, α$_2$M activated by methylamine or trypsin, or α$_2$M-2 activated by methylamine or trypsin, in the presence or absence of RAP (400 nM). To assess anti-LRP-Aβ/$^{125}$I-Aβ endocytosis by LRP, chloroquine (0.1 mM) is added at the same time as anti-LRP-Aβ/$^{125}$I-Aβ (4 nM) to inhibit lysosomal degradation of $^{125}$I-Aβ (Kounnas, M. Z., et al., *Cell* 82:331–340 (1995)).

Following 18 hours of incubation with the anti-LRP-Aβ/$^{125}$I-Aβ, cells are washed with phosphate-buffered saline and treated with a trypsin-EDTA, proteinase K solution. Surface-bound material is defined as the amount of radioactive ligand released by this treatment, and the amount of internalized ligand is defined as the amount of radioactivity which remains associated with the cell pellet following the treatment.

Activated α$_2$M/$^{125}$I-Aβ will serve as positive control. Under the conditions described, more than 4–8 fmoles/10$^4$ cells of activated α$_2$M/$^{125}$I-Aβ should be internalized after 18 hours of incubation (Kounnas, M. Z., et al., *Cell* 82:331–340 (1995)). Unactivated α$_2$M/$^{125}$I-Aβ will serve as the negative control, because α$_2$M must be activated by trypsin or methylamine to be recognized by LRP. If the amount of anti-LRP-Aβ/$^{125}$I-Aβ is greater than 2–4 fmoles/10$^4$ cells, it can be concluded that anti-LRP-Aβ/$^{125}$I-Aβ has the ability to undergo LRP mediated endocytosis. Unactivated α$_2$M/$^{125}$I-Aβ, and activated α$_2$M/$^{125}$I-Aβ in the presence of RAP should not be internalized, therefore no more than 2–4 fmoles/10$^4$ cells should be internalized (Kounnas, M. Z., et al., *Cell* 82:331–340 (1995)). Internalization of the anti-LRP-Aβ/$^{125}$I-Aβ complex will be deemed abolished if anti-LRP-Aβ/$^{125}$I-Aβ, in the presence and absence of RAP, and unactivated α$_2$M/$^{125}$I-Aβ show the same amount of radioactivity associated with the cell pellet.

Degradation. The experiment above to test endocytosis is repeated without chloroquine. The radioactivity appearing in the cell culture medium that is soluble in 10% trichloroacetic acid is taken to represent degraded $^{125}$I-Aβ (Kounnas, M. Z., et al., *Cell* 82:331–340 (1995); Narita, M., et al., *J. Neurochem.* 69:1904–1911 (1997)). Total ligand degradation is corrected for the amount of degradation that occurs in control wells lacking cells. Because free $^{125}$I-Aβ can be degraded in an LRP independent manner, degradation is measured for anti-LRP-Aβ and α$_2$M complexes with $^{125}$I-Aβ as well as for free $^{125}$I-Aβ in the presence and absence of RAP. Using the same positive and negative controls as above, if RAP does not decrease the amount of TCA soluble radioactivity by at least 30% for the anti-LRP-Aβ/$^{125}$I-Aβ complex it can be concluded that $^{125}$I-Aβ ligand of anti-LRP-Aβ is not degraded.

The anti-LRP-Aβ peptide may not promote Aβ binding and degradation because of steric constrains. If the anti-LRP-Aβ polypeptide does not promote Aβ binding and degradation another peptide is synthesized with a pentaglycine linker between the Aβ and LRP binding regions to provide the flexibility needed to bind both targets simultaneously. This anti-LRP-Aβ with linker is tested for Aβ binding, and LRP mediated endocytosis and degradation as described above. If this anti-LRP-Aβ does not provide for Aβ and LRP binding, the three hybrid system is used to reoptimize binding, and to screen for anti-LRP-Aβ with the ability to bind both Aβ and LRP.

The use of peptides in therapy is associated with two problems, transport across the blood-brain barrier, and the generation of an immune response. These problems can be minimized by shortening the peptide length. Thus when optimizing the anti-LRP-Aβ peptide, shorter binding domains may be preferred over longer domains, where binding capabilities are equally effective.

Yeast three hybrid system. The yeast three hybrid system is a genetic method to detect ternary protein complex formation (FIG. 7) (Tirode, F., et al., *J. Biol. Chem.* 272:22995–22999 (1997); Osborne, M. A., et al., *Biotechnology* 13:1474–1478 (1995); Zhang, J. and Lautar, S., *Anal. Biochem.* 242:68–72 (1996); Licitra, E. J. and Liu, J. O., *Proc. Natl. Acad. Sci. U.S.A.* 93:12817–12821 (1996)). In the system, yeast growth only occurs when the "bait" recognizes both the "hook" and the "fish" (FIG. 7). In this instance, the "hook" is constructed of the DNA coding for Aβ (Bales, K. R., et al., *Nat. Genet.* 17:264 (1997)), fused to the coding sequence of the LexA DNA binding protein in pLex9-3H, a TRP1 episomal vector (Tirode, F., et al., *J. Biol. Chem.* 272:22995–22999 (1997)). The "fish" is constructed of the coding sequence for the 515 kD extracellular domain of LRP, fused to the B42 activation domain in pVP 16, a LEU2 episomal vector (Tirode, F., et al., *J. Biol. Chem.* 272:22995–22999 (1997)). The "bait" is the DNA coding for anti-LRP-Aβ in the pLex9-3H vector, expression of anti-LRP-Aβ is repressed by methionine. These vectors are transformed into the L40 yeast strain. Transcription of the Leu 2 reporter gene occurs only when the Aβ fused DNA binding domain is brought into proximity to the transcriptional activation domain fused to LRP.

The Aβ/LRP binding fusion peptide should promote reporter gene transcription. The interaction between anti-LRP-Aβ and Aβ and LRP (515 kD) will be considered positive only if reporter gene expression (yeast growth) occurs when Aβ-LexA, LRP(515 kD)-B42, and anti-LRP-Aβ are expressed. It is not likely that expression of Aβ-LexA will cause activation of the reporter transcription since this construct has been used successfully in the past. It is also unlikely that LRP(515 kD)-B42 expression alone will cause reporter transcription, LRP(515 kD) is not known to bind DNA. The interaction of Aβ-LexA and LRP(515 kD)-B42 would cause reporter transcription and the Aβ parent protein APP is known to interact with LRP. However, the interaction between LRP and APP occurs via the Kunitz protease inhibitory domain far removed from the location of Aβ in APP (Kounnas, M. Z., et al., Cell 82:331–340 (1995)). In addition biochemical evidence suggests that LRP does not recognize Aβ (Narita, M., et al., J. Neurochem. 69:1904–1911 (1997)). Transformation of the Aβ-LexA and LRP(515 kD)-B42 containing plasmids into EGY48 and monitoring the growth on media lacking leucine is carried out to insure that Aβ-LexA and LRP(515 kD)-B42 do not interact. As positive controls the DNA sequence encoding the entire α$_2$M monomer and the sequence encoding residues 1202–1451 of α$_2$M are cloned separately into pLex9-3H, in place of anti-LRP-Aβ. The C-terminal fragment of α$_2$M contains the full length Aβ and LRP binding domains (residues 1202–1451 of α$_2$M) and it, along with the monomer, should give rise to reporter gene transcription.

If expression of anti-LRP-Aβ, Aβ-LexA, and LRP(515 kD)-B42 does not activate reporter transcription then each of the binary interactions of anti-LRP-Aβ are tested in a traditional two hybrid screen. That is, concomitant expression of anti-LRP-Aβ-B42 and Aβ-LexA, as well as anti-LRP-Aβ-B-42 and LRP(515 kD)-LexA, is used to assess the ability of anti-LRP-Aβ to interact with Aβ-LexA and LRP (515 kD)-LexA individually. If anti-LRP-Aβ interacts individually with both targets then one or all of the following is carried out: (i) a 5 residue glycine linker is added between the Aβ binding domain and the LRP binding to allow flexibility between the two binding domains, (ii) the Aβ-LexA and LRP(515 kD)-B42 fusion partners are switched to become LRP(515 kD)-LexA and Aβ-B42, and (iii) the polarity of the anti-LRP-Aβ is switched so that the LRP binding domain is N-terminal to the Aβ binding domain. If anti-LRP-Aβ interacts with one or neither of the targets, binding is reoptimized using random mutagenesis and selection by three hybrid screen for binding to both targets. The non-binding region of anti-LRP-Aβ is subjected to protein evolution techniques, error prone PCR and DNA shuffling (Buchholz, F., et al., Nat. Biotechnol. 16:657–662 (1998)), followed by selection of constructs that bind target proteins. This is repeated until target binding is achieved.

Modifications of the above-described modes for carrying out the invention that are obvious to persons of skill in medicine, genetics, molecular biology, biochemistry, pharmacology and/or related fields are intended to be within the scope of the following claims.

All publications and patents mentioned in this specification are indicative of the level of skill of those skilled in the art to which this invention pertains. All publications and patents mentioned are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A method of screening for an agent that increases the ratio of A2M-1 mRNA to A2M-2 mRNA comprising:
   (a) incubating one or more test cells in the presence of a test agent, wherein said test cells are heterozygous or homozygous for the A2M-2 allele; and
   (b) comparing the ratio of A2M-1 mRNA to A2M-2 mRNA in said test cells to the ratio of A2M-1 mRNA to A2M-2 mRNA in one or more control cells, wherein said control cells are untreated with said test agent and said control cells carry the same number of A2M-2 alleles as said test cells; and wherein a ratio of A2M-1 mRNA to A2M-2 mRNA in said test cells significantly higher than the ratio of A2M-1 mRNA to A2M-2 mRNA in said control cells indicates that said test agent is effective.

2. The method of claim 1, wherein a ratio of A2M-1 mRNA to A2M-2 mRNA in said test cells twice said ratio of A2M-1 mRNA to A2M-2 mRNA in said control cells indicates that said test agent is effective.

3. The method of claim 1, wherein said test cells are heterozygous for the A2M-2 allele.

4. The method of claim 1, wherein said test cells are homozygous for the A2M-2 allele.

5. The method of claim 1, wherein said test cells and said control cells are selected from the group consisting of glioma cells, hepatoma cells and hepatocytes.

6. The method of claim 1, wherein comparing the ratio of A2M-1 mRNA to A2M-2 mRNA in said test cells to the ratio of A2M-1 mRNA to A2M-2 mRNA in one or more control cells comprises:
   (a) hybridizing mRNA from said test cells to a probe comprising a polynucleotide sequence complementary to mRNA encoding exon 18 of A2M-1;
   (b) incubating said mRNA from said test cells with S1 nuclease to produce a first digestion product, wherein said first digestion product comprises A2M mRNA fragments hybridized to said probe, and wherein said A2M mRNA fragments are A2M-1 mRNA fragments and/or A2M-2 mRNA fragments;
   (c) hybridizing MRNA from said control cells to said probe;
   (d) incubating said mRNA from said control cells with S1 nuclease to produce a second digestion product, wherein said second digestion product comprises A2M mRNA fragments hybridized to said probe, and wherein said A2M mRNA fragments are A2M-1 mRNA fragments and A2M-2 mRNA fragments;
   (e) separating said A2M mRNA fragments in said first digestion product according to size and separating said A2M mRNA fragments in said second digestion product according to size, wherein said A2M-1 mRNA fragments are larger than said A2M-2 mRNA fragments; and
   (f) quantitating the amount of said A2M-1 mRNA fragments and the amount of said A2M-2 mRNA fragments in said first digestion product and the amount of said A2M-1 mRNA fragments and the amount of said A2M-2 mRNA fragments in said second digestion product;
   (g) comparing the ratio of A2M-1 mRNA to A2M-2 mRNA in said first digestion product to the ratio of A2M-1 mRNA to A2M-2 mRNA in said second digestion product; wherein a ratio of A2M-1 mRNA to A2M-2 mRNA in said first digestion product significantly higher than said ratio of A2M-1 mRNA to A2M-2 mRNA in said second digestion product indicates that said test agent is effective.

7. The method of claim 6, wherein said probe is 250–500 nucleotides in length.

8. The method of claim 7, wherein said probe comprises a polynucleotide sequence complementary to mRNA encoding exons 17 and 18 of A2M.

9. The method of claim 7, wherein said probe comprises a polynucleotide sequence complementary to mRNA encoding exons 17, 18, and 19 of A2M.

10. The method of claim 9, wherein said test cells are heterozygous for the A2M-2 allele.

11. The method of claim 9, wherein said test cells are homozygous for the A2M-2 allele.

12. The method of claim 6, wherein said probe has a sequence complementary to nucleotides 2057–2284 of SEQ ID NO:1.

13. The method of claim 6, wherein said probe has a sequence complementary to nucleotides 2024–2323 of SEQ ID NO:1.

14. The method of claim 6, wherein said probe has a sequence complementary to nucleotides 2057–2384 of SEQ ID NO:1.

15. The method of claim 1, wherein comparing the ratio of A2M-1 mRNA to A2M-2 mRNA in said test cells to the ratio of A2M-1 mRNA to A2M-2 mRNA in one or more control cells comprises:

(a) amplifying the mRNA from said test cells using reverse transcriptase polymerase chain reaction (RT-PCR) to produce a first amplification product comprising A2M DNA fragments, wherein a first primer and a second primer are used in said RT-PCR, wherein said first primer and said second primer, when used in PCR to amplify cDNA encoding A2M-1, amplify a region of said cDNA comprising exon 18, and wherein said A2M DNA fragments are A2M-1 DNA fragments and A2M-2 DNA fragments;

(b) amplifying the mRNA from said control cells using RT-PCR to produce a second amplification product comprising A2M DNA fragments, wherein said first primer and said second primer are used in said RT-PCR, and wherein said A2M DNA fragments are A2M-1 DNA fragments and/or A2M-2 DNA fragments;

(c) separating said A2M DNA fragments in said first amplification product according to size and separating said A2M DNA fragments in said second amplification product according to size, wherein A2M-1 DNA fragments are larger than A2M-2 DNA fragments;

(d) quantitating the amount of A2M-1 DNA fragments and the amount of A2M-2 DNA fragments in said first digestion product and the amount of A2M-1 DNA fragments and the amount of A2M-2 DNA fragments in said second digestion product; and (e) comparing the ratio of A2M-1 DNA fragments to A2M-2 DNA fragments in said first amplification product to the ratio of A2M-1 DNA fragments to A2M-2 DNA fragments in said second amplification product; wherein a ratio of A2M-1 DNA fragments to A2M-2 DNA fragments in said first amplification product significantly higher than said ratio of A2M-1 DNA fragments to A2M-2 DNA fragments in said second amplification product indicates that said test agent is effective.

16. The method of claim 15, wherein said region comprises exons 17 and 18 of A2M.

17. The method of claim 15, wherein said region comprises exons 17, 18, and 19 of A2M.

18. The method of claim 17, wherein said test cells are heterozygous for the A2M-2 allele.

19. The method of claim 17, wherein said test cells are homozygous for the A2M-2 allele.

20. The method of claim 17, wherein said first primer is 8–50 nucleotides in length and said second primer is 8–50 nucleotides in length.

21. The method of claim 15, wherein said region has the sequence of nucleotides 2052–2289 of SEQ ID NO:1.

22. The method of claim 15, wherein said region has the sequence of nucleotides 2052–2289 of SEQ ID NO:1.

23. The method of claim 15, wherein said first primer has a nucleotide sequence complementary to nucleotides 2024–2038 of SEQ ID NO:1, and said second primer has a nucleotide sequence of nucleotides 2309–2323 of SEQ ID NO:1.

24. The method of claim 15, wherein said first primer has a nucleotide sequence of nucleotides 2024–2038 of SEQ ID NO:1, and said second primer has a nucleotide sequence complementary to nucleotides 2309–2323 of SEQ ID NO:1.

* * * * *

SEQUENCE LISTING

```
<160> NUMBER OF SEQ ID NOS: 27

<210> SEQ ID NO 1
<211> LENGTH: 4577
<212> TYPE: DNA
<213> ORGANISM: Homo sapiens
<220> FEATURE:
<221> NAME/KEY: sig_peptide
<222> LOCATION: (44)..(112)
<220> FEATURE:
<221> NAME/KEY: CDS
<222> LOCATION: (44)..(4468)
<220> FEATURE:
<221> NAME/KEY: mat_peptide
<222> LOCATION: (113)..(4468)

<400> SEQUENCE: 1
gctacaatcc atctggtctc ctccagctcc ttctttctgc aac atg ggg aag aac        55
                                              Met Gly Lys Asn
                                                      -20 aaa ctc ctt cat cca agt ctg gtt ctt ctc ctc ttg gtc ctc ctg ccc      103
Lys Leu Leu His Pro Ser Leu Val Leu Leu Leu Leu Val Leu Leu Pro
            -15                 -10                  -5 aca gac gcc tca gtc tct gga aaa ccg cag tat atg gtt ctg gtc ccc      151
Thr Asp Ala Ser Val Ser Gly Lys Pro Gln Tyr Met Val Leu Val Pro
```

```
            -1    1                    5                              10 tcc ctg ctc cac act gag acc act gag aag ggc tgt gtc ctt ctg agc    199
          Ser Leu Leu His Thr Glu Thr Thr Glu Lys Gly Cys Val Leu Leu Ser
                   15                  20                  25 tac ctg aat gag aca gtg act gta agt gct tcc ttg gag tct gtc agg    247
          Tyr Leu Asn Glu Thr Val Thr Val Ser Ala Ser Leu Glu Ser Val Arg
               30                  35                  40                  45 gga aac agg agc ctc ttc act gac ctg gag gcg gag aat gac gta ctc    295
          Gly Asn Arg Ser Leu Phe Thr Asp Leu Glu Ala Glu Asn Asp Val Leu
                            50                  55                  60 cac tgt gtc gcc ttc gct gtc cca aag tct tca tcc aat gag gag gta    343
          His Cys Val Ala Phe Ala Val Pro Lys Ser Ser Ser Asn Glu Glu Val
                       65                  70                  75 atg ttc ctc act gtc caa gtg aaa gga cca acc caa gaa ttt aag aag    391
          Met Phe Leu Thr Val Gln Val Lys Gly Pro Thr Gln Glu Phe Lys Lys
                   80                  85                  90 cgg acc aca gtg atg gtt aag aac gag gac agt ctg gtc ttt gtc cag    439
          Arg Thr Thr Val Met Val Lys Asn Glu Asp Ser Leu Val Phe Val Gln
               95                  100                 105 aca gac aaa tca atc tac aaa cca ggg cag aca gtg aaa ttt cgt gtt    487
          Thr Asp Lys Ser Ile Tyr Lys Pro Gly Gln Thr Val Lys Phe Arg Val
          110                 115                 120                 125 gtc tcc atg gat gaa aac ttt cac ccc ctg aat gag ttg att cca cta    535
          Val Ser Met Asp Glu Asn Phe His Pro Leu Asn Glu Leu Ile Pro Leu
                            130                 135                 140 gta tac att cag gat ccc aaa gga aat cgc atc gca caa tgg cag agt    583
          Val Tyr Ile Gln Asp Pro Lys Gly Asn Arg Ile Ala Gln Trp Gln Ser
                       145                 150                 155 ttc cag tta gag ggt ggc ctc aag caa ttt tct ttt ccc ctc tca tca    631
          Phe Gln Leu Glu Gly Gly Leu Lys Gln Phe Ser Phe Pro Leu Ser Ser
                   160                 165                 170 gag ccc ttc cag ggc tcc tac aag gtg gtg gta cag aag aaa tca ggt    679
          Glu Pro Phe Gln Gly Ser Tyr Lys Val Val Val Gln Lys Lys Ser Gly
               175                 180                 185 gga agg aca gag cac cct ttc acc gtg gag gaa ttt gtt ctt ccc aag    727
          Gly Arg Thr Glu His Pro Phe Thr Val Glu Glu Phe Val Leu Pro Lys
          190                 195                 200                 205 ttt gaa gta caa gta aca gtg cca aag ata atc acc atc ttg gaa gaa    775
          Phe Glu Val Gln Val Thr Val Pro Lys Ile Ile Thr Ile Leu Glu Glu
                            210                 215                 220 gag atg aat gta tca gtg tgt ggc cta tac aca tat ggg aag cct gtc    823
          Glu Met Asn Val Ser Val Cys Gly Leu Tyr Thr Tyr Gly Lys Pro Val
                       225                 230                 235 cct gga cat gtg act gtg agc att tgc aga aag tat agt gac gct tcc    871
          Pro Gly His Val Thr Val Ser Ile Cys Arg Lys Tyr Ser Asp Ala Ser
                   240                 245                 250 gac tgc cac ggt gaa gat tca cag gct ttc tgt gag aaa ttc agt gga    919
          Asp Cys His Gly Glu Asp Ser Gln Ala Phe Cys Glu Lys Phe Ser Gly
               255                 260                 265 cag cta aac agc cat ggc tgc ttc tat cag caa gta aaa acc aag gtc    967
          Gln Leu Asn Ser His Gly Cys Phe Tyr Gln Gln Val Lys Thr Lys Val
          270                 275                 280                 285 ttc cag ctg aag agg aag gag tat gaa atg aaa ctt cac act gag gcc    1015
          Phe Gln Leu Lys Arg Lys Glu Tyr Glu Met Lys Leu His Thr Glu Ala
                            290                 295                 300 cag atc caa gaa gaa gga aca gtg gtg gaa ttg act gga agg cag tcc    1063
          Gln Ile Gln Glu Glu Gly Thr Val Val Glu Leu Thr Gly Arg Gln Ser
                       305                 310                 315 agt gaa atc aca aga acc ata acc aaa ctc tca ttt gtg aaa gtg gac    1111
```

```
Ser Glu Ile Thr Arg Thr Ile Thr Lys Leu Ser Phe Val Lys Val Asp
        320                 325                 330 tca cac ttt cga cag gga att ccc ttc ttt ggg cag gtg cgc cta gta      1159
Ser His Phe Arg Gln Gly Ile Pro Phe Phe Gly Gln Val Arg Leu Val
    335                 340                 345 gat ggg aaa ggc gtc cct ata cca aat aaa gtc ata ttc atc aga gga      1207
Asp Gly Lys Gly Val Pro Ile Pro Asn Lys Val Ile Phe Ile Arg Gly
350                 355                 360                 365 aat gaa gca aac tat tac tcc aat gct acc acg gat gag cat ggc ctt      1255
Asn Glu Ala Asn Tyr Tyr Ser Asn Ala Thr Thr Asp Glu His Gly Leu
                370                 375                 380 gta cag ttc tct atc aac acc acc aac gtt atg ggt acc tct ctt act      1303
Val Gln Phe Ser Ile Asn Thr Thr Asn Val Met Gly Thr Ser Leu Thr
            385                 390                 395 gtt agg gtc aat tac aag gat cgt agt ccc tgt tac ggc tac cag tgg      1351
Val Arg Val Asn Tyr Lys Asp Arg Ser Pro Cys Tyr Gly Tyr Gln Trp
        400                 405                 410 gtg tca gaa gaa cac gaa gag gca cat cac act gct tat ctt gtg ttc      1399
Val Ser Glu Glu His Glu Glu Ala His His Thr Ala Tyr Leu Val Phe
    415                 420                 425 tcc cca agc aag agc ttt gtc cac ctt gag ccc atg tct cat gaa cta      1447
Ser Pro Ser Lys Ser Phe Val His Leu Glu Pro Met Ser His Glu Leu
430                 435                 440                 445 ccc tgt ggc cat act cag aca gtc cag gca cat tat att ctg aat gga      1495
Pro Cys Gly His Thr Gln Thr Val Gln Ala His Tyr Ile Leu Asn Gly
                450                 455                 460 ggc acc ctg ctg ggg ctg aag aag ctc tcc ttt tat tat ctg ata atg      1543
Gly Thr Leu Leu Gly Leu Lys Lys Leu Ser Phe Tyr Tyr Leu Ile Met
            465                 470                 475 gca aag gga ggc att gtc cga act ggg act cat gga ctg ctt gtg aag      1591
Ala Lys Gly Gly Ile Val Arg Thr Gly Thr His Gly Leu Leu Val Lys
        480                 485                 490 cag gaa gac atg aag ggc cat ttt tcc atc tca atc cct gtg aag tca      1639
Gln Glu Asp Met Lys Gly His Phe Ser Ile Ser Ile Pro Val Lys Ser
    495                 500                 505 gac att gct cct gtc gct cgg ttg ctc atc tat gct gtt tta cct acc      1687
Asp Ile Ala Pro Val Ala Arg Leu Leu Ile Tyr Ala Val Leu Pro Thr
510                 515                 520                 525 ggg gac gtg att ggg gat tct gca aaa tat gat gtt gaa aat tgt ctg      1735
Gly Asp Val Ile Gly Asp Ser Ala Lys Tyr Asp Val Glu Asn Cys Leu
                530                 535                 540 gcc aac aag gtg gat ttg agc ttc agc cca tca caa agt ctc cca gcc      1783
Ala Asn Lys Val Asp Leu Ser Phe Ser Pro Ser Gln Ser Leu Pro Ala
            545                 550                 555 tca cac gcc cac ctg cga gtc aca gcg gct cct cag tcc gtc tgc gcc      1831
Ser His Ala His Leu Arg Val Thr Ala Ala Pro Gln Ser Val Cys Ala
        560                 565                 570 ctc cgt gct gtg gac caa agc gtg ctg ctc atg aag cct gat gct gag      1879
Leu Arg Ala Val Asp Gln Ser Val Leu Leu Met Lys Pro Asp Ala Glu
    575                 580                 585 ctc tcg gcg tcc tcg gtt tac aac ctg cta cca gaa aag gac ctc act      1927
Leu Ser Ala Ser Ser Val Tyr Asn Leu Leu Pro Glu Lys Asp Leu Thr
590                 595                 600                 605 ggc ttc cct ggg cct ttg aat gac cag gac gat gaa gac tgc atc aat      1975
Gly Phe Pro Gly Pro Leu Asn Asp Gln Asp Asp Glu Asp Cys Ile Asn
                610                 615                 620 cgt cat aat gtc tat att aat gga atc aca tat act cca gta tca agt      2023
Arg His Asn Val Tyr Ile Asn Gly Ile Thr Tyr Thr Pro Val Ser Ser
            625                 630                 635
```

-continued

| | |
|---|---|
| aca aat gaa aag gat atg tac agc ttc cta gag gac atg ggc tta aag<br>Thr Asn Glu Lys Asp Met Tyr Ser Phe Leu Glu Asp Met Gly Leu Lys<br>640                           645                   650 | 2071 |
| gca ttc acc aac tca aag att cgt aaa ccc aaa atg tgt cca cag ctt<br>Ala Phe Thr Asn Ser Lys Ile Arg Lys Pro Lys Met Cys Pro Gln Leu<br>655                       660                     665 | 2119 |
| caa cag tat gaa atg cat gga cct gaa ggt cta cgt gta ggt ttt tat<br>Gln Gln Tyr Glu Met His Gly Pro Glu Gly Leu Arg Val Gly Phe Tyr<br>670                     675                   680                 685 | 2167 |
| gag tca gat gta atg gga aga ggc cat gca cgc ctg gtg cat gtt gaa<br>Glu Ser Asp Val Met Gly Arg Gly His Ala Arg Leu Val His Val Glu<br>                 690                   695                   700 | 2215 |
| gag cct cac acg gag acc gta cga aag tac ttc cct gag aca tgg atc<br>Glu Pro His Thr Glu Thr Val Arg Lys Tyr Phe Pro Glu Thr Trp Ile<br>705                       710                   715 | 2263 |
| tgg gat ttg gtg gtg gta aac tca gca ggg gtg gct gag gta gga gta<br>Trp Asp Leu Val Val Val Asn Ser Ala Gly Val Ala Glu Val Gly Val<br>720                     725                   730 | 2311 |
| aca gtc cct gac acc atc acc gag tgg aag gca ggg gcc ttc tgc ctg<br>Thr Val Pro Asp Thr Ile Thr Glu Trp Lys Ala Gly Ala Phe Cys Leu<br>735                     740                   745 | 2359 |
| tct gaa gat gct gga ctt ggt atc tct tcc act gcc tct ctc cga gcc<br>Ser Glu Asp Ala Gly Leu Gly Ile Ser Ser Thr Ala Ser Leu Arg Ala<br>750                     755                   760                 765 | 2407 |
| ttc cag ccc ttc ttt gtg gag ctt aca atg cct tac tct gtg att cgt<br>Phe Gln Pro Phe Phe Val Glu Leu Thr Met Pro Tyr Ser Val Ile Arg<br>                 770                   775                   780 | 2455 |
| gga gag gcc ttc aca ctc aag gcc acg gtc cta aac tac ctt ccc aaa<br>Gly Glu Ala Phe Thr Leu Lys Ala Thr Val Leu Asn Tyr Leu Pro Lys<br>                 785                   790                   795 | 2503 |
| tgc atc cgg gtc agt gtg cag ctg gaa gcc tct ccc gcc ttc ctt gct<br>Cys Ile Arg Val Ser Val Gln Leu Glu Ala Ser Pro Ala Phe Leu Ala<br>800                       805                   810 | 2551 |
| gtc cca gtg gag aag gaa caa gcg cct cac tgc atc tgt gca aac ggg<br>Val Pro Val Glu Lys Glu Gln Ala Pro His Cys Ile Cys Ala Asn Gly<br>815                       820                   825 | 2599 |
| cgg caa act gtg tcc tgg gca gta acc cca aag tca tta gga aat gtg<br>Arg Gln Thr Val Ser Trp Ala Val Thr Pro Lys Ser Leu Gly Asn Val<br>830                       835                   840                 845 | 2647 |
| aat ttc act gtg agc gca gag gca cta gag tct caa gag ctg tgt ggg<br>Asn Phe Thr Val Ser Ala Glu Ala Leu Glu Ser Gln Glu Leu Cys Gly<br>                 850                   855                   860 | 2695 |
| act gag gtg cct tca gtt cct gaa cac gga agg aaa gac aca gtc atc<br>Thr Glu Val Pro Ser Val Pro Glu His Gly Arg Lys Asp Thr Val Ile<br>                     865                   870                 875 | 2743 |
| aag cct ctg ttg gtt gaa cct gaa gga cta gag aag gaa aca aca ttc<br>Lys Pro Leu Leu Val Glu Pro Glu Gly Leu Glu Lys Glu Thr Thr Phe<br>880                       885                   890 | 2791 |
| aac tcc cta ctt tgt cca tca ggt ggt gag gtt tct gaa gaa tta tcc<br>Asn Ser Leu Leu Cys Pro Ser Gly Gly Glu Val Ser Glu Glu Leu Ser<br>895                       900                   905 | 2839 |
| ctg aaa ctg cca cca aat gtg gta gaa gaa tct gcc cga gct tct gtc<br>Leu Lys Leu Pro Pro Asn Val Val Glu Glu Ser Ala Arg Ala Ser Val<br>910                       915                   920                 925 | 2887 |
| tca gtt ttg gga gac ata tta ggc tct gcc atg caa aac aca caa aat<br>Ser Val Leu Gly Asp Ile Leu Gly Ser Ala Met Gln Asn Thr Gln Asn<br>                 930                   935                   940 | 2935 |
| ctt ctc cag atg ccc tat ggc tgt gga gag cag aat atg gtc ctc ttt<br>Leu Leu Gln Met Pro Tyr Gly Cys Gly Glu Gln Asn Met Val Leu Phe<br>945                       950                   955 | 2983 |

```
gct cct aac atc tat gta ctg gat tat cta aat gaa aca cag cag ctt      3031
Ala Pro Asn Ile Tyr Val Leu Asp Tyr Leu Asn Glu Thr Gln Gln Leu
        960                 965                 970 act cca gag atc aag tcc aag gcc att ggc tat ctc aac act ggt tac      3079
Thr Pro Glu Ile Lys Ser Lys Ala Ile Gly Tyr Leu Asn Thr Gly Tyr
    975                 980                 985 cag aga cag ttg aac tac aaa cac tat gat ggc tcc tac agc acc ttt      3127
Gln Arg Gln Leu Asn Tyr Lys His Tyr Asp Gly Ser Tyr Ser Thr Phe
990                 995                 1000                1005 ggg gag cga tat ggc agg aac cag ggc aac acc tgg ctc aca gcc ttt      3175
Gly Glu Arg Tyr Gly Arg Asn Gln Gly Asn Thr Trp Leu Thr Ala Phe
                1010                1015                1020 gtt ctg aag act ttt gcc caa gct cga gcc tac atc ttc atc gat gaa      3223
Val Leu Lys Thr Phe Ala Gln Ala Arg Ala Tyr Ile Phe Ile Asp Glu
            1025                1030                1035 gca cac att acc caa gcc ctc ata tgg ctc tcc cag agg cag aag gac      3271
Ala His Ile Thr Gln Ala Leu Ile Trp Leu Ser Gln Arg Gln Lys Asp
        1040                1045                1050 aat ggc tgt ttc agg agc tct ggg tca ctg ctc aac aat gcc ata aag      3319
Asn Gly Cys Phe Arg Ser Ser Gly Ser Leu Leu Asn Asn Ala Ile Lys
    1055                1060                1065 gga gga gta gaa gat gaa gtg acc ctc tcc gcc tat atc acc atc gcc      3367
Gly Gly Val Glu Asp Glu Val Thr Leu Ser Ala Tyr Ile Thr Ile Ala
1070                1075                1080                1085 ctt ctg gag att cct ctc aca gtc act cac cct gtt gtc cgc aat gcc      3415
Leu Leu Glu Ile Pro Leu Thr Val Thr His Pro Val Val Arg Asn Ala
                1090                1095                1100 ctg ttt tgc ctg gag tca gcc tgg aag aca gca caa gaa ggg gac cat      3463
Leu Phe Cys Leu Glu Ser Ala Trp Lys Thr Ala Gln Glu Gly Asp His
            1105                1110                1115 ggc agc cat gta tat acc aaa gca ctg ctg gcc tat gct ttt gcc ctg      3511
Gly Ser His Val Tyr Thr Lys Ala Leu Leu Ala Tyr Ala Phe Ala Leu
        1120                1125                1130 gca ggt aac cag gac aag agg aag gaa gta ctc aag tca ctt aat gag      3559
Ala Gly Asn Gln Asp Lys Arg Lys Glu Val Leu Lys Ser Leu Asn Glu
    1135                1140                1145 gaa gct gtg aag aaa gac aac tct gtc cat tgg gag cgc cct cag aaa      3607
Glu Ala Val Lys Lys Asp Asn Ser Val His Trp Glu Arg Pro Gln Lys
1150                1155                1160                1165 ccc aag gca cca gtg ggg cat ttt tac gaa ccc cag gct ccc tct gct      3655
Pro Lys Ala Pro Val Gly His Phe Tyr Glu Pro Gln Ala Pro Ser Ala
                1170                1175                1180 gag gtg gag atg aca tcc tat gtg ctc ctc gct tat ctc acg gcc cag      3703
Glu Val Glu Met Thr Ser Tyr Val Leu Leu Ala Tyr Leu Thr Ala Gln
            1185                1190                1195 cca gcc cca acc tcg gag gac ctg acc tct gca acc aac atc gtg aag      3751
Pro Ala Pro Thr Ser Glu Asp Leu Thr Ser Ala Thr Asn Ile Val Lys
        1200                1205                1210 tgg atc acg aag cag cag aat gcc cag ggc ggt ttc tcc tcc acc cag      3799
Trp Ile Thr Lys Gln Gln Asn Ala Gln Gly Gly Phe Ser Ser Thr Gln
    1215                1220                1225 gac aca gtg gtg gct ctc cat gct ctg tcc aaa tat gga gcc gcc aca      3847
Asp Thr Val Val Ala Leu His Ala Leu Ser Lys Tyr Gly Ala Ala Thr
1230                1235                1240                1245 ttt acc agg act ggg aag gct gca cag gtg act atc cag tct tca ggg      3895
Phe Thr Arg Thr Gly Lys Ala Ala Gln Val Thr Ile Gln Ser Ser Gly
                1250                1255                1260 aca ttt tcc agc aaa ttc caa gtg gac aac aac aat cgc ctg tta ctg      3943
Thr Phe Ser Ser Lys Phe Gln Val Asp Asn Asn Asn Arg Leu Leu Leu
```

-continued

```
             1265                1270                1275
cag cag gtc tca ttg cca gag ctg cct ggg gaa tac agc atg aaa gtg       3991
Gln Gln Val Ser Leu Pro Glu Leu Pro Gly Glu Tyr Ser Met Lys Val
        1280                1285                1290 aca gga gaa gga tgt gtc tac ctc cag acc tcc ttg aaa tac aat att       4039
Thr Gly Glu Gly Cys Val Tyr Leu Gln Thr Ser Leu Lys Tyr Asn Ile
    1295                1300                1305 ctc cca gaa aag gaa gag ttc ccc ttt gct tta gga gtg cag act ctg       4087
Leu Pro Glu Lys Glu Glu Phe Pro Phe Ala Leu Gly Val Gln Thr Leu
1310                1315                1320                1325 cct caa act tgt gat gaa ccc aaa gcc cac acc agc ttc caa atc tcc       4135
Pro Gln Thr Cys Asp Glu Pro Lys Ala His Thr Ser Phe Gln Ile Ser
            1330                1335                1340 cta agt gtc agt tac aca ggg agc cgc tct gcc tcc aac atg gcg atc       4183
Leu Ser Val Ser Tyr Thr Gly Ser Arg Ser Ala Ser Asn Met Ala Ile
        1345                1350                1355 gtt gat gtg aag atg gtc tct ggc ttc att ccc ctg aag cca aca gtg       4231
Val Asp Val Lys Met Val Ser Gly Phe Ile Pro Leu Lys Pro Thr Val
    1360                1365                1370 aaa atg ctt gaa aga tct aac cat gtg agc cgg aca gaa gtc agc agc       4279
Lys Met Leu Glu Arg Ser Asn His Val Ser Arg Thr Glu Val Ser Ser
1375                1380                1385 aac cat gtc ttg att tac ctt gat aag gtg tca aat cag aca ctg agc       4327
Asn His Val Leu Ile Tyr Leu Asp Lys Val Ser Asn Gln Thr Leu Ser
1390                1395                1400                1405 ttg ttc ttc acg gtt ctg caa gat gtc cca gta aga gat ctc aaa cca       4375
Leu Phe Phe Thr Val Leu Gln Asp Val Pro Val Arg Asp Leu Lys Pro
        1410                1415                1420 gcc ata gtg aaa gtc tat gat tac tac gag acg gat gag ttt gca atc       4423
Ala Ile Val Lys Val Tyr Asp Tyr Tyr Glu Thr Asp Glu Phe Ala Ile
    1425                1430                1435 gct gag tac aat gct cct tgc agc aaa gat ctt gga aat gct tga           4468
Ala Glu Tyr Asn Ala Pro Cys Ser Lys Asp Leu Gly Asn Ala
        1440                1445                1450 agaccacaag gctgaaaagt gctttgctgg agtcctgttc tctgagctcc acagaagaca    4528 cgtgttttg tatctttaaa gacttgatga ataaacactt tttctggtc                 4577
```

<210> SEQ ID NO 2
<211> LENGTH: 1474
<212> TYPE: PRT
<213> ORGANISM: Homo sapiens

<400> SEQUENCE: 2

```
Met Gly Lys Asn Lys Leu Leu His Pro Ser Leu Val Leu Leu Leu
 1               5                  10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110
```

-continued

```
Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
            195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
            275                 280                 285

Lys Phe Ser Gly Gln Leu Asn Ser His Gly Cys Phe Tyr Gln Gln Val
    290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
    355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
            435                 440                 445

Tyr Leu Val Phe Ser Pro Ser Lys Ser Phe Val His Leu Glu Pro Met
    450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
```

-continued

```
                530                 535                 540
Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
                595                 600                 605

Pro Asp Ala Glu Leu Ser Ala Ser Ser Val Tyr Asn Leu Leu Pro Glu
                610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
                675                 680                 685

Cys Pro Gln Leu Gln Gln Tyr Glu Met His Gly Pro Glu Gly Leu Arg
                690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
                740                 745                 750

Glu Val Gly Val Thr Val Pro Asp Thr Ile Thr Glu Trp Lys Ala Gly
                755                 760                 765

Ala Phe Cys Leu Ser Glu Asp Ala Gly Leu Gly Ile Ser Ser Thr Ala
                770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
                835                 840                 845

Cys Ala Asn Gly Arg Gln Thr Val Ser Trp Ala Val Thr Pro Lys Ser
                850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
                915                 920                 925

Glu Glu Leu Ser Leu Lys Leu Pro Pro Asn Val Val Glu Glu Ser Ala
                930                 935                 940

Arg Ala Ser Val Ser Val Leu Gly Asp Ile Leu Gly Ser Ala Met Gln
945                 950                 955                 960
```

-continued

```
Asn Thr Gln Asn Leu Leu Gln Met Pro Tyr Gly Cys Gly Glu Gln Asn
            965                 970                 975
Met Val Leu Phe Ala Pro Asn Ile Tyr Val Leu Asp Tyr Leu Asn Glu
            980                 985                 990
Thr Gln Gln Leu Thr Pro Glu Ile Lys Ser Lys Ala Ile Gly Tyr Leu
            995                1000                1005
Asn Thr Gly Tyr Gln Arg Gln Leu Asn Tyr Lys His Tyr Asp Gly Ser
       1010                1015                1020
Tyr Ser Thr Phe Gly Glu Arg Tyr Gly Arg Asn Gln Gly Asn Thr Trp
025                1030                1035                1040
Leu Thr Ala Phe Val Leu Lys Thr Phe Ala Gln Ala Arg Ala Tyr Ile
            1045                1050                1055
Phe Ile Asp Glu Ala His Ile Thr Gln Ala Leu Ile Trp Leu Ser Gln
            1060                1065                1070
Arg Gln Lys Asp Asn Gly Cys Phe Arg Ser Ser Gly Ser Leu Leu Asn
            1075                1080                1085
Asn Ala Ile Lys Gly Gly Val Glu Asp Glu Val Thr Leu Ser Ala Tyr
            1090                1095                1100
Ile Thr Ile Ala Leu Leu Glu Ile Pro Leu Thr Val Thr His Pro Val
105                 1110                1115                1120
Val Arg Asn Ala Leu Phe Cys Leu Glu Ser Ala Trp Lys Thr Ala Gln
            1125                1130                1135
Glu Gly Asp His Gly Ser His Val Tyr Thr Lys Ala Leu Leu Ala Tyr
            1140                1145                1150
Ala Phe Ala Leu Ala Gly Asn Gln Asp Lys Arg Lys Glu Val Leu Lys
            1155                1160                1165
Ser Leu Asn Glu Glu Ala Val Lys Lys Asp Asn Ser Val His Trp Glu
            1170                1175                1180
Arg Pro Gln Lys Pro Lys Ala Pro Val Gly His Phe Tyr Glu Pro Gln
185                 1190                1195                1200
Ala Pro Ser Ala Glu Val Glu Met Thr Ser Tyr Val Leu Leu Ala Tyr
            1205                1210                1215
Leu Thr Ala Gln Pro Ala Pro Thr Ser Glu Asp Leu Thr Ser Ala Thr
            1220                1225                1230
Asn Ile Val Lys Trp Ile Thr Lys Gln Gln Asn Ala Gln Gly Gly Phe
            1235                1240                1245
Ser Ser Thr Gln Asp Thr Val Val Ala Leu His Ala Leu Ser Lys Tyr
            1250                1255                1260
Gly Ala Ala Thr Phe Thr Arg Thr Gly Lys Ala Ala Gln Val Thr Ile
265                 1270                1275                1280
Gln Ser Ser Gly Thr Phe Ser Ser Lys Phe Gln Val Asp Asn Asn Asn
            1285                1290                1295
Arg Leu Leu Leu Gln Gln Val Ser Leu Pro Glu Leu Pro Gly Glu Tyr
            1300                1305                1310
Ser Met Lys Val Thr Gly Glu Gly Cys Val Tyr Leu Gln Thr Ser Leu
            1315                1320                1325
Lys Tyr Asn Ile Leu Pro Glu Lys Glu Glu Phe Pro Phe Ala Leu Gly
            1330                1335                1340
Val Gln Thr Leu Pro Gln Thr Cys Asp Glu Pro Lys Ala His Thr Ser
345                 1350                1355                1360
Phe Gln Ile Ser Leu Ser Val Ser Tyr Thr Gly Ser Arg Ser Ala Ser
            1365                1370                1375
```

```
Asn Met Ala Ile Val Asp Val Lys Met Val Ser Gly Phe Ile Pro Leu
        1380                1385                1390
Lys Pro Thr Val Lys Met Leu Glu Arg Ser Asn His Val Ser Arg Thr
    1395                1400                1405
Glu Val Ser Ser Asn His Val Leu Ile Tyr Leu Asp Lys Val Ser Asn
1410                1415                1420
Gln Thr Leu Ser Leu Phe Phe Thr Val Leu Gln Asp Val Pro Val Arg
425                 1430                1435                1440
Asp Leu Lys Pro Ala Ile Val Lys Val Tyr Asp Tyr Tyr Glu Thr Asp
            1445                1450                1455
Glu Phe Ala Ile Ala Glu Tyr Asn Ala Pro Cys Ser Lys Asp Leu Gly
        1460                1465                1470
Asn Ala
```

<210> SEQ ID NO 3
<211> LENGTH: 750
<212> TYPE: DNA
<213> ORGANISM: Homo sapiens
<220> FEATURE:
<221> NAME/KEY: CDS
<222> LOCATION: (1)..(750)
<223> OTHER INFORMATION: A /LRP Binding Domain

<400> SEQUENCE: 3

```
tcg gag gac ctg acc tct gca acc aac atc gtg aag tgg atc acg aag      48
Ser Glu Asp Leu Thr Ser Ala Thr Asn Ile Val Lys Trp Ile Thr Lys
1               5                   10                  15 cag cag aat gcc cag ggc ggt ttc tcc tcc acc cag gac aca gtg gtg      96
Gln Gln Asn Ala Gln Gly Gly Phe Ser Ser Thr Gln Asp Thr Val Val
            20                  25                  30 gct ctc cat gct ctg tcc aaa tat gga gcc gcc aca ttt acc agg act     144
Ala Leu His Ala Leu Ser Lys Tyr Gly Ala Ala Thr Phe Thr Arg Thr
        35                  40                  45 ggg aag gct gca cag gtg act atc cag tct tca ggg aca ttt tcc agc     192
Gly Lys Ala Ala Gln Val Thr Ile Gln Ser Ser Gly Thr Phe Ser Ser
    50                  55                  60 aaa ttc caa gtg gac aac aac aat cgc ctg tta ctg cag cag gtc tca     240
Lys Phe Gln Val Asp Asn Asn Asn Arg Leu Leu Leu Gln Gln Val Ser
65                  70                  75                  80 ttg cca gag ctg cct ggg gaa tac agc atg aaa gtg aca gga gaa gga     288
Leu Pro Glu Leu Pro Gly Glu Tyr Ser Met Lys Val Thr Gly Glu Gly
                85                  90                  95 tgt gtc tac ctc cag acc tcc ttg aaa tac aat att ctc cca gaa aag     336
Cys Val Tyr Leu Gln Thr Ser Leu Lys Tyr Asn Ile Leu Pro Glu Lys
            100                 105                 110 gaa gag ttc ccc ttt gct tta gga gtg cag act ctg cct caa act tgt     384
Glu Glu Phe Pro Phe Ala Leu Gly Val Gln Thr Leu Pro Gln Thr Cys
        115                 120                 125 gat gaa ccc aaa gcc cac acc agc ttc caa atc tcc cta agt gtc agt     432
Asp Glu Pro Lys Ala His Thr Ser Phe Gln Ile Ser Leu Ser Val Ser
    130                 135                 140 tac aca ggg agc cgc tct gcc tcc aac atg gcg atc gtt gat gtg aag     480
Tyr Thr Gly Ser Arg Ser Ala Ser Asn Met Ala Ile Val Asp Val Lys
145                 150                 155                 160 atg gtc tct ggc ttc att ccc ctg aag cca aca gtg aaa atg ctt gaa     528
Met Val Ser Gly Phe Ile Pro Leu Lys Pro Thr Val Lys Met Leu Glu
                165                 170                 175 aga tct aac cat gtg agc cgg aca gaa gtc agc agc aac cat gtc ttg     576
Arg Ser Asn His Val Ser Arg Thr Glu Val Ser Ser Asn His Val Leu
            180                 185                 190
```

```
att tac ctt gat aag gtg tca aat cag aca ctg agc ttg ttc ttc acg        624
Ile Tyr Leu Asp Lys Val Ser Asn Gln Thr Leu Ser Leu Phe Phe Thr
        195                 200                 205 gtt ctg caa gat gtc cca gta aga gat ctc aaa cca gcc ata gtg aaa        672
Val Leu Gln Asp Val Pro Val Arg Asp Leu Lys Pro Ala Ile Val Lys
    210                 215                 220 gtc tat gat tac tac gag acg gat gag ttt gca atc gct gag tac aat        720
Val Tyr Asp Tyr Tyr Glu Thr Asp Glu Phe Ala Ile Ala Glu Tyr Asn
225                 230                 235                 240 gct cct tgc agc aaa gat ctt gga aat gct                                750
Ala Pro Cys Ser Lys Asp Leu Gly Asn Ala
                245                 250

<210> SEQ ID NO 4
<211> LENGTH: 250
<212> TYPE: PRT
<213> ORGANISM: Homo sapiens

<400> SEQUENCE: 4

Ser Glu Asp Leu Thr Ser Ala Thr Asn Ile Val Lys Trp Ile Thr Lys
 1               5                  10                  15

Gln Gln Asn Ala Gln Gly Gly Phe Ser Ser Thr Gln Asp Thr Val Val
            20                  25                  30

Ala Leu His Ala Leu Ser Lys Tyr Gly Ala Ala Thr Phe Thr Arg Thr
        35                  40                  45

Gly Lys Ala Ala Gln Val Thr Ile Gln Ser Ser Gly Thr Phe Ser Ser
    50                  55                  60

Lys Phe Gln Val Asp Asn Asn Asn Arg Leu Leu Leu Gln Gln Val Ser
65                  70                  75                  80

Leu Pro Glu Leu Pro Gly Glu Tyr Ser Met Lys Val Thr Gly Glu Gly
                85                  90                  95

Cys Val Tyr Leu Gln Thr Ser Leu Lys Tyr Asn Ile Leu Pro Glu Lys
            100                 105                 110

Glu Glu Phe Pro Phe Ala Leu Gly Val Gln Thr Leu Pro Gln Thr Cys
        115                 120                 125

Asp Glu Pro Lys Ala His Thr Ser Phe Gln Ile Ser Leu Ser Val Ser
    130                 135                 140

Tyr Thr Gly Ser Arg Ser Ala Ser Asn Met Ala Ile Val Asp Val Lys
145                 150                 155                 160

Met Val Ser Gly Phe Ile Pro Leu Lys Pro Thr Val Lys Met Leu Glu
                165                 170                 175

Arg Ser Asn His Val Ser Arg Thr Glu Val Ser Ser Asn His Val Leu
            180                 185                 190

Ile Tyr Leu Asp Lys Val Ser Asn Gln Thr Leu Ser Leu Phe Phe Thr
        195                 200                 205

Val Leu Gln Asp Val Pro Val Arg Asp Leu Lys Pro Ala Ile Val Lys
    210                 215                 220

Val Tyr Asp Tyr Tyr Glu Thr Asp Glu Phe Ala Ile Ala Glu Tyr Asn
225                 230                 235                 240

Ala Pro Cys Ser Lys Asp Leu Gly Asn Ala
                245                 250

<210> SEQ ID NO 5
<211> LENGTH: 333
<212> TYPE: DNA
<213> ORGANISM: Homo sapiens
<220> FEATURE:
```

```
<221> NAME/KEY: CDS
<222> LOCATION: (1)..(333)
<223> OTHER INFORMATION: A Binding Domain

<400> SEQUENCE: 5 tcg gag gac ctg acc tct gca acc aac atc gtg aag tgg atc acg aag      48
Ser Glu Asp Leu Thr Ser Ala Thr Asn Ile Val Lys Trp Ile Thr Lys
  1               5                  10                  15 cag cag aat gcc cag ggc ggt ttc tcc tcc acc cag gac aca gtg gtg      96
Gln Gln Asn Ala Gln Gly Gly Phe Ser Ser Thr Gln Asp Thr Val Val
             20                  25                  30 gct ctc cat gct ctg tcc aaa tat gga gcc gcc aca ttt acc agg act     144
Ala Leu His Ala Leu Ser Lys Tyr Gly Ala Ala Thr Phe Thr Arg Thr
         35                  40                  45 ggg aag gct gca cag gtg act atc cag tct tca ggg aca ttt tcc agc     192
Gly Lys Ala Ala Gln Val Thr Ile Gln Ser Ser Gly Thr Phe Ser Ser
     50                  55                  60 aaa ttc caa gtg gac aac aac aat cgc ctg tta ctg cag cag gtc tca     240
Lys Phe Gln Val Asp Asn Asn Asn Arg Leu Leu Leu Gln Gln Val Ser
 65                  70                  75                  80 ttg cca gag ctg cct ggg gaa tac agc atg aaa gtg aca gga gaa gga     288
Leu Pro Glu Leu Pro Gly Glu Tyr Ser Met Lys Val Thr Gly Glu Gly
                 85                  90                  95 tgt gtc tac ctc cag acc tcc ttg aaa tac aat att ctc cca gaa         333
Cys Val Tyr Leu Gln Thr Ser Leu Lys Tyr Asn Ile Leu Pro Glu
            100                 105                 110

<210> SEQ ID NO 6
<211> LENGTH: 111
<212> TYPE: PRT
<213> ORGANISM: Homo sapiens

<400> SEQUENCE: 6

Ser Glu Asp Leu Thr Ser Ala Thr Asn Ile Val Lys Trp Ile Thr Lys
  1               5                  10                  15

Gln Gln Asn Ala Gln Gly Gly Phe Ser Ser Thr Gln Asp Thr Val Val
             20                  25                  30

Ala Leu His Ala Leu Ser Lys Tyr Gly Ala Ala Thr Phe Thr Arg Thr
         35                  40                  45

Gly Lys Ala Ala Gln Val Thr Ile Gln Ser Ser Gly Thr Phe Ser Ser
     50                  55                  60

Lys Phe Gln Val Asp Asn Asn Asn Arg Leu Leu Leu Gln Gln Val Ser
 65                  70                  75                  80

Leu Pro Glu Leu Pro Gly Glu Tyr Ser Met Lys Val Thr Gly Glu Gly
                 85                  90                  95

Cys Val Tyr Leu Gln Thr Ser Leu Lys Tyr Asn Ile Leu Pro Glu
            100                 105                 110

<210> SEQ ID NO 7
<211> LENGTH: 417
<212> TYPE: DNA
<213> ORGANISM: Homo sapiens
<220> FEATURE:
<221> NAME/KEY: CDS
<222> LOCATION: (1)..(417)
<223> OTHER INFORMATION: LRP Binding Domain

<400> SEQUENCE: 7 aag gaa gag ttc ccc ttt gct tta gga gtg cag act ctg cct caa act      48
Lys Glu Glu Phe Pro Phe Ala Leu Gly Val Gln Thr Leu Pro Gln Thr
  1               5                  10                  15
```

```
tgt gat gaa ccc aaa gcc cac acc agc ttc caa atc tcc cta agt gtc      96
Cys Asp Glu Pro Lys Ala His Thr Ser Phe Gln Ile Ser Leu Ser Val
         20                  25                  30 agt tac aca ggg agc cgc tct gcc tcc aac atg gcg atc gtt gat gtg     144
Ser Tyr Thr Gly Ser Arg Ser Ala Ser Asn Met Ala Ile Val Asp Val
         35                  40                  45 aag atg gtc tct ggc ttc att ccc ctg aag cca aca gtg aaa atg ctt     192
Lys Met Val Ser Gly Phe Ile Pro Leu Lys Pro Thr Val Lys Met Leu
 50                  55                  60 gaa aga tct aac cat gtg agc cgg aca gaa gtc agc agc aac cat gtc     240
Glu Arg Ser Asn His Val Ser Arg Thr Glu Val Ser Ser Asn His Val
 65                  70                  75                  80 ttg att tac ctt gat aag gtg tca aat cag aca ctg agc ttg ttc ttc     288
Leu Ile Tyr Leu Asp Lys Val Ser Asn Gln Thr Leu Ser Leu Phe Phe
                 85                  90                  95 acg gtt ctg caa gat gtc cca gta aga gat ctc aaa cca gcc ata gtg     336
Thr Val Leu Gln Asp Val Pro Val Arg Asp Leu Lys Pro Ala Ile Val
            100                 105                 110 aaa gtc tat gat tac tac gag acg gat gag ttt gca atc gct gag tac     384
Lys Val Tyr Asp Tyr Tyr Glu Thr Asp Glu Phe Ala Ile Ala Glu Tyr
            115                 120                 125 aat gct cct tgc agc aaa gat ctt gga aat gct                         417
Asn Ala Pro Cys Ser Lys Asp Leu Gly Asn Ala
        130                 135
```

<210> SEQ ID NO 8
<211> LENGTH: 139
<212> TYPE: PRT
<213> ORGANISM: Homo sapiens

<400> SEQUENCE: 8

```
Lys Glu Glu Phe Pro Phe Ala Leu Gly Val Gln Thr Leu Pro Gln Thr
 1               5                  10                  15

Cys Asp Glu Pro Lys Ala His Thr Ser Phe Gln Ile Ser Leu Ser Val
             20                  25                  30

Ser Tyr Thr Gly Ser Arg Ser Ala Ser Asn Met Ala Ile Val Asp Val
         35                  40                  45

Lys Met Val Ser Gly Phe Ile Pro Leu Lys Pro Thr Val Lys Met Leu
 50                  55                  60

Glu Arg Ser Asn His Val Ser Arg Thr Glu Val Ser Ser Asn His Val
 65                  70                  75                  80

Leu Ile Tyr Leu Asp Lys Val Ser Asn Gln Thr Leu Ser Leu Phe Phe
                 85                  90                  95

Thr Val Leu Gln Asp Val Pro Val Arg Asp Leu Lys Pro Ala Ile Val
            100                 105                 110

Lys Val Tyr Asp Tyr Tyr Glu Thr Asp Glu Phe Ala Ile Ala Glu Tyr
            115                 120                 125

Asn Ala Pro Cys Ser Lys Asp Leu Gly Asn Ala
        130                 135
```

<210> SEQ ID NO 9
<211> LENGTH: 81
<212> TYPE: DNA
<213> ORGANISM: Homo sapiens
<220> FEATURE:
<221> NAME/KEY: CDS
<222> LOCATION: (1)..(81)
<223> OTHER INFORMATION: Consensus LRP Binding Domain

<400> SEQUENCE: 9

```
ttc att ccc ctg aag cca aca gtg aaa atg ctt gaa aga tct aac cat       48
Phe Ile Pro Leu Lys Pro Thr Val Lys Met Leu Glu Arg Ser Asn His
 1               5                  10                  15 gtg agc cgg aca gaa gtc agc agc aac cat gtc                           81
Val Ser Arg Thr Glu Val Ser Ser Asn His Val
         20                  25

<210> SEQ ID NO 10
<211> LENGTH: 27
<212> TYPE: PRT
<213> ORGANISM: Homo sapiens

<400> SEQUENCE: 10

Phe Ile Pro Leu Lys Pro Thr Val Lys Met Leu Glu Arg Ser Asn His
 1               5                  10                  15

Val Ser Arg Thr Glu Val Ser Ser Asn His Val
         20                  25

<210> SEQ ID NO 11
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION: A  Fibril Inhibitor

<400> SEQUENCE: 11 cgc gat ctg cca ttc ttc cca gtc cca att gat                           33
Arg Asp Leu Pro Phe Phe Pro Val Pro Ile Asp
 1               5                  10

<210> SEQ ID NO 12
<211> LENGTH: 11
<212> TYPE: PRT
<213> ORGANISM: Homo sapiens

<400> SEQUENCE: 12

Arg Asp Leu Pro Phe Phe Pro Val Pro Ile Asp
 1               5                  10

<210> SEQ ID NO 13
<211> LENGTH: 114
<212> TYPE: DNA
<213> ORGANISM: Homo sapiens
<220> FEATURE:
<221> NAME/KEY: CDS
<222> LOCATION: (1)..(114)
<223> OTHER INFORMATION: A  Fibril Inhibitor

<400> SEQUENCE: 13 cgc gat ctg cca ttc ttc cca gtc cca att gat ttc att ccc ctg aag       48
Arg Asp Leu Pro Phe Phe Pro Val Pro Ile Asp Phe Ile Pro Leu Lys
 1               5                  10                  15 cca aca gtg aaa atg ctt gaa aga tct aac cat gtg agc cgg aca gaa       96
Pro Thr Val Lys Met Leu Glu Arg Ser Asn His Val Ser Arg Thr Glu
             20                  25                  30 gtc agc agc aac cat gtc                                              114
Val Ser Ser Asn His Val
             35

<210> SEQ ID NO 14
<211> LENGTH: 38
<212> TYPE: PRT
<213> ORGANISM: Homo sapiens
```

<400> SEQUENCE: 14

Arg Asp Leu Pro Phe Phe Pro Val Pro Ile Asp Phe Ile Pro Leu Lys
1               5                   10                  15

Pro Thr Val Lys Met Leu Glu Arg Ser Asn His Val Ser Arg Thr Glu
            20                  25                  30

Val Ser Ser Asn His Val
        35

<210> SEQ ID NO 15
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 15 cgc gat ctg cca ttc ttc cca gtc gat                                27
Arg Asp Leu Pro Phe Phe Pro Val Asp
1               5

<210> SEQ ID NO 16
<211> LENGTH: 9
<212> TYPE: PRT
<213> ORGANISM: Homo sapiens

<400> SEQUENCE: 16

Arg Asp Leu Pro Phe Phe Pro Val Asp
1               5

<210> SEQ ID NO 17
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 17 ctg cca ttc ttc cca gtc gat                                        21
Leu Pro Phe Phe Pro Val Asp
1               5

<210> SEQ ID NO 18
<211> LENGTH: 7
<212> TYPE: PRT
<213> ORGANISM: Homo sapiens

<400> SEQUENCE: 18

Leu Pro Phe Phe Pro Val Asp
1               5

<210> SEQ ID NO 19
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 19 ctg cca ttc ttc gtc gat                                            18
Leu Pro Phe Phe Val Asp
1               5

```
<210> SEQ ID NO 20
<211> LENGTH: 6
<212> TYPE: PRT
<213> ORGANISM: Homo sapiens

<400> SEQUENCE: 20

Leu Pro Phe Phe Val Asp
  1               5

<210> SEQ ID NO 21
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 21 ctg cca ttc ttc gat                                             15
Leu Pro Phe Phe Asp
  1               5

<210> SEQ ID NO 22
<211> LENGTH: 5
<212> TYPE: PRT
<213> ORGANISM: Homo sapiens

<400> SEQUENCE: 22

Leu Pro Phe Phe Asp
  1               5

<210> SEQ ID NO 23
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 23 ctg cca ttc ttc                                                 12
Leu Pro Phe Phe
  1

<210> SEQ ID NO 24
<211> LENGTH: 4
<212> TYPE: PRT
<213> ORGANISM: Homo sapiens

<400> SEQUENCE: 24

Leu Pro Phe Phe
  1

<210> SEQ ID NO 25
<211> LENGTH: 9
<212> TYPE: DNA
<213> ORGANISM: Homo sapiens
<220> FEATURE:
<221> NAME/KEY: CDS
<222> LOCATION: (1)..(9)

<400> SEQUENCE: 25 cca ttc ttc                                                      9
Pro Phe Phe
  1

<210> SEQ ID NO 26
```

-continued

```
<211> LENGTH: 3
<212> TYPE: PRT
<213> ORGANISM: Homo sapiens

<400> SEQUENCE: 26

Pro Phe Phe
  1

<210> SEQ ID NO 27
<211> LENGTH: 50
<212> TYPE: DNA
<213> ORGANISM: Homo sapiens
<220> FEATURE:
<223> OTHER INFORMATION: Noncoding-antisense DNA

<400> SEQUENCE: 27
catgcaccag gcgtgcatgg cctcttccca ttacatctga ctctgagtga        50
```